US008138330B2

(12) United States Patent
Leuck et al.

(10) Patent No.: US 8,138,330 B2
(45) Date of Patent: Mar. 20, 2012

(54) PROCESS FOR THE SYNTHESIS OF OLIGONUCLEOTIDES

(75) Inventors: Michael Leuck, Hamburg (DE); Andreas Wolter, Hamburg (DE); Alfred Stumpe, Hamburg (DE)

(73) Assignee: Sigma-Aldrich Co. LLC, St. Louis, MO (US)

( * ) Notice: Subject to any disclaimer, the term of this patent is extended or adjusted under 35 U.S.C. 154(b) by 736 days.

(21) Appl. No.: 11/853,662

(22) Filed: Sep. 11, 2007

(65) Prior Publication Data
US 2008/0064867 A1 Mar. 13, 2008

Related U.S. Application Data

(60) Provisional application No. 60/825,175, filed on Sep. 11, 2006.

(51) Int. Cl.
C07H 21/02 (2006.01)
C07H 21/04 (2006.01)
(52) U.S. Cl. .................................................. 536/25.31
(58) Field of Classification Search .................... None
See application file for complete search history.

(56) References Cited

U.S. PATENT DOCUMENTS

| 4,415,732 | A |   | 11/1983 | Caruthers et al. |         |
|-----------|---|---|---------|------------------|---------|
| 4,458,066 | A |   | 7/1984  | Caruthers et al. |         |
| 4,500,707 | A |   | 2/1985  | Caruthers et al. |         |
| 4,668,777 | A |   | 5/1987  | Caruthers et al. |         |
| 4,973,679 | A |   | 11/1990 | Caruthers et al. |         |
| 5,132,418 | A |   | 7/1992  | Caruthers et al. |         |
| RE34,069  | E |   | 9/1992  | Koster et al.    |         |
| 5,519,126 | A | * | 5/1996  | Hecht            | 536/24.3 |
| 6,222,030 | B1|   | 4/2001  | Dellinger et al. |         |
| 6,609,195 | B2|   | 8/2003  | Dover            |         |
| 6,887,990 | B1| * | 5/2005  | Bhan et al.      | 536/25.31 |
| 6,989,442 | B2| * | 1/2006  | Vargeese         | 536/25.31 |

OTHER PUBLICATIONS

Griffin et al., "The Synthesis of Oligonucleotides-IV Preparation of Dinucleoside Phosphates from 2,5'-Protected Ribonucleoside Derivatives".*
Greene et al., "Protective groups in Organic Synthesis", published 1999 by John Wiley and Sons, chapter 2, Protection for the Hydroxylgroup, Including 1,2-and 1,3=Diols, pp. 17-244.*
Chattopadhyaya et al., "Chemical Synthesis of a Tridecanucleoside dodecaphosphate sequence of SV40 DNA" Nucleic Acids Research (1980) vol. 8 No. 8, pp. 2039-2053.*
Zegelaar-Jaarsveld, "Iodonium Ion-Assisted Synthesis of Tetrameric Fragments Corresponding to the Cell Wall Phenolic Glycolipids of *Mycobacterium kansasii* serovars II and IV" Tetrahedron (1996) vol. 52 No. 10, pp. 3575-3592.*
Kamimura et al., "Protection of Imide Group of Uracil Moiety by Means of 2,2,2-trichloro-tert-butyloxycarbonyl chloride: A selective synthesis of 2'-O-methyluridine" Chemistry Letters (1982) pp. 965-968.*

Cook et al., "Use of Chloroacetic Anhydride for the Protection of Nucleoside Hydroxyl Groups" Journal of Organic Chemistry (1970) vol. 35 No. 6, pp. 1940-1943.*
Protective Groups in Organic Synthesis, Third Edition, by Theodora Greene and Peter Wuts, published 1999 by John Wiley and Sons, Inc, pp. 160-165.*
Griffin et al., "The Synthesis of Oligonucleotides-IV Preparation of Dinucleoside Phosphates from 2,5'-Protected Ribonucleoside Derivatives" Tetrahedron (1968) vol. 24 pp. 639-662.*
Beaucage et al., "Advances in the Synthesisof Oligonucleotides by the Phosphoramidite Approach"; Tetrahedron; 1992; pp. 2223-2311; vol. 48; No. 12.
Beaucage et al., "The Synthesis of Modified Oligonucleotides by the Phosphoramidite Approach and Their Applications"; Tetrahedron; 1993; pp. 6123-6194; vol. 49; No. 28.
Bergmann et al., "The 2-Dansylethoxycarbonyl (=2{[5(Dimethylamino)naphthalen-1-yl]sulfonyl}ethoxycarbonyl; Dnseoc) Group for Protection of the 5'-Hydroxy Function in Oligodeoxyribonucleotide Synthesis"; Helvetica Chimica Acta; 1994; pp. 203-215; vol. 77.
Bergmann et al., "Allyl as Internucleotide Protecting Group in DNA Synthesis to be Cleaved off by Ammonia"; Tetrahedron; 1995; pp. 6971-6976; vol. 51, No. 25.
Fearon et al.; "Investigation of the 'n-1' impurity in phosphorothioate oligodeoxynucleotides synthesized by the solid-phase beta-cyanoethyl phosphoramidite method using stepwise sulfurization"; Nucleic Acids Research; 1995; pp. 2754-2761; vol. 23; No. 14.
Gryaznov et al., "Selective O-phosphitilation with nucleoside phoshoramidite reagents"; 1992; Nucleic Acids Research; pp. 1879-1882; vol. 20; No. 8.
Honda et al., "Synthesis of Oligoribonucleotides by Use of S,S-Diphenyl N-Monomethoxytrityl Ribonucleoside 3'-Phosphorodithioates"; Tetrahedron; 1984; pp. 153-163; vol. 40; No. 1.
Iwai et al., "5-Levulinyl and 2'tetrahydrofuranyl protection for the synthesis of oligoribonucleotides by the phosphoramidite approach"; Nucleic Acids Research; 1988; pp. 9443-9456; vol. 18; No. 20.

(Continued)

*Primary Examiner* — Eric S Olson
(74) *Attorney, Agent, or Firm* — Polsinelli Shughart PC

(57) ABSTRACT

The present invention discloses novel methods for the synthesis of oligonucleotides with nucleoside phosphoramidites on solid supports. The methods comprise the stepwise chain assembly of oligonucleotides on supports with 5'-acyl phosphoramidites. The synthesis cycles consist of a front end deprotection step which is conducted with a solution of a primary amine or a phenolate, a phosphoramidite coupling step with a 5'-acyl nucleoside phosphoramidite in the presence of an activator, a phosphite oxidation step and an optional capping step. The novel methods improve the quality of synthetic oligonucleotides due to the irreversibility of the front end deprotection step, which prevents the formation of deletion sequences, and due to the avoidance of acidic reagents in the synthesis cycles, which prevent the formation of depurination side products. The invention further discloses novel nucleoside phosphoramidite compositions wherein the phosphoramidites carry acyl front end protective groups which are cleavable with primary amines or phenolates. The invention is applicable to the synthesis of oligodeoxyribonucleotides, oligoribonucleotides and oligonucleotides with modifications in their sugar or phosphate groups.

23 Claims, 6 Drawing Sheets

OTHER PUBLICATIONS

Kamaike et al., "Oligonucleotide Synthesis by the Use of a 2-(Levulinyloxymethyl)-5-nitrobenzoyl Group as the Novel Base-labile Protecting Group for the 5'Hydroxyl Groups of Ribonucleoside and 2'-Deoxyribonucleoside 3'- Phosphoramidites"; Tetrahedron Letters; 1997; pp. 6857-6860; vol. 38; No. 39.

Katoaoka et al., "Ethyl(methyl)dioxirane as an Efficient Reagent for the Oxidation of Nucleoside Phosphites into Phosphates under Nonbasic Anhydrous Conditions"; Organic Letters; 2001; pp. 815-818; vol. 3; No. 6.

Kawahara et al., "Unprecedented Mild Acid-Catalyzed Desilylation of the 2'-O-tert-Butyldimethylsilyl Group from Chemically Synthesized Oligoribonucleotide Intermediates via Neighboring Group participation of the Internucleotidic Phosphate Residue"; Journal of the American Chemical Society; 1996; pp. 9461-9468; vol. 118; No. 40.

Kumar et al., "Improvements in Oligodeoxyribonucleotide Synthesis: Methyl N,N-Dialkylphosphoramidite Dimer Units for Solid Support Phosphite Methodogy"; Journal of Organic Chemistry; 1984; pp. 4905-4912; vol. 49.

Lehmann et al., "Solid-phase synthesis of oligoribonucleotides using 9-fluorenylmethoxycarbonyl (Fmoc) for 5-40 -hydroxyl protection"; Nucleic Acids Research; 1989; pp. 2379-2390; vol. 17; No. 7.

Lloyd et al., "Some observations relating to the use of 1-aryl-4-alkoxypiperidin-4-yl groups for the protection of the 2'-hydroxy functions in the chemical synthesis of oligoribonucleotides"; Journal of Chemical Society Perkin Transactions 1; 2000; pp. 165-176.

Manoharan et al.; "Allyl Group as a Protecting Group for Internucleotide Phosphate and Thiophosphate Linkages in Oligoncleotide Synthesis: Facile Oxidation and Deprotection Conditions"; Organic Letters; 2000; pp. 243-246; vol. 2, No. 3.

Matysiak et al., "Acetals as New 2'-O-Protecting Functions for the Synthesis of Oligoribonucleotides: Synthesis of Uridine Building Blocks and Evaluation of Their Relative Acid Stability"; Helvetica Chimica Acta; 1998; pp. 1545-1566; vol. 81.

McBride et al., "An Investigation of Several Deoxynucleoside Phoshoramidites Useful for Synthesizing Deoxyolignucleotides", Tetrahedron Letters; 1983; pp. 245-248; vol. 24, No. 3.

Micklefield; "Backbone Modification of Nucleic Acids: Synthesis, Structure and Therapeutic Applications"; Current Medicinal Chemistry; 2001; pp. 1157-1179; vol. 8.

Munch et al., "The (2-Cyano-1-Phenyl) Ethoxycarbonyl (CPEOC) Group—A New Protecting Group for Oligoribonucleotide Synthesis"; Nucleosides and Nucleotides; 1997; pp. 801-808; vol. 16; Nos. 5 and 6.

Norman et al.; "The Protection of 2'-Hydroxy Functions in Oligoribocleotide Synthesis"; Tetrahedron Letters; 1984; pp. 3015-3018; vol. 25; No. 28.

Ohtsuka et al., "Studies on transfer ribonucleic acids and related compounds. XLV. Block condensation of ribooligonucleotides containing 2'-O-tetrahydrofuranyl-5'-O-dimethoxytritylnucleosides"; Nucleic Acids Research; 1983; pp. 1325-1335; vol. 11; No. 5.

Ono et al.; "The synthesis of blocked triplet-phosphoramidites and their use in mutagenesis"; Nucleic Acid Research; 1995; pp. 4677-4682; vol. 23; No. 22.

Palom et al., "An Acid-Labile Linker for Solid-Phase Oligoribonucleotide Synthesis Using Fmoc Group for 5'Hydroxyl Protection"; Tetrahedron Letters; 1993; pp. 2195-2198; vol. 34; No. 13.

Rao et al.; "Use of the 1-(2-Fluorophenyl)-4-methoxypiperidin-4-yl (Fpmp) Protecting Group in the Solid-Phase Synthesis of Oligo- and Poly-ribonucleotides"; Journal of the Chemical Society-Perkin Transactions 1; 1993; pp. 43-55.

Reese et al., "4-Methoxytetrahydropyran-4-yl A Symmetrical Alternative to the Tetrahydropyranyl Protecting Group"; Tetrahedron; 1970; pp. 1023-1030; vol. 26.

Robles et al., "Solid-Phase synthesis of a nucleopeptide from the linking site of adenovirus-2 nucleoprotein, -Ser (p5'CATCAT)-Gly-Asp-. Convergent versus stepwise strategy" Nucleic Acids Research; 1995; pp. 4151-4161; vol. 23; No. 20.

Sandstrom et al., "Chemical Synthesis of a Pentaribonucleoside Tetraphosphate Constituting the 3'-Acceptor Stem Sequence of E. coli tRNA Ile Using 2'-O-(3-Methoxy-1,5-dicarbomethoxypentan-3-yl)-ribonucleoside Building Blocks. Application of a New Achiral and Acid-labile 2'-Hydroxyl Protecting Group in tRNA Synthesis"; Acta Chemica Scandinavica B; 1985; pp. 273-290; vol. 39.

Scaringe et al., "Novel RNA Synthesis Method Using 5'-O-Silyl-2'-O-orthester Protecting Groups"; Journal of the American Chemical Society; 1998; pp. 11820-11821; vol. 120.

Seio et al., "Synthesis of pentathymidylate using a 4-monomethoxytritylthio (MMTrS) group as a 5'-hydroxyl protecting group: toward oligonucleotide synthesis without acid treatment"; Tetrahedron Letters; 2001; pp. 8657-8660; vol. 42.

Sekine et al., "Synthesis of Short Oligoribonucleotides Bearing a 3'- or 5'- Terminal Phosphate by use of 4, 4',4"-Tris(4,5-dichlorophthalimido)trityl as a New 5'-Hydroxyl Protection Group", Journal of American Chemical Society; 1986; pp. 4581-4586; vol. 108.

Sekine et al., "Proton-Block Strategy for the Synthesis of Oligodeoxynucleotides without Base Protection, Capping Reaction, and P-N Bond Cleavage Reaction"; Journal of Organic Chemistry; 2003; pp. 5478-5492; vol. 68.

Seliger et al., "The P-Phenylazophenyloxycarbonyl Protecting Group: Selective Deblocking and Oligonucleotide Synthesis Avoiding Acid Steps"; Nucleosides & Nucleotides; 1985; pp. 153-155; vol. 4, No. 1 and 2.

Sierzchala et al., "Solid-Phase Oligodeoxynucleotide Synthesis: A Two-Step Cycle Using Peroxy Anion Deprotection"; Journal of American Chemical Society; 2003; pp. 13427-13441; vol. 125.

Sinha et al.; "beta-Cyanoethyl N, N-Dialkylamino/N-Morpholinomonochloro Phosphoamidites, New Phosphitylating Agents Facilitating Ease of Deprotection and Work-Up of Synthesized Oligonucleotides"; Tetrahedron Letters; 1983; pp. 5843-5846; vol. 24; No. 52.

Song et al.; "A Short, Novel, and Cheaper Procedure for Oligonucleotide Synthesis Using Automated Solid Phase Synthesizer"; Nucleosides, Nucleotides & Nucleic Acids; 2003; pp. 629-633; vol. 22; Nos. 5-8.

Temsamani et al.; "Sequence identity of the n-1 product of a synthetic oligonucleotide"; Nucleic Acids Research; 1995; pp. 1841-1844; vol. 23; No. 11.

Tsukamoto et al.; "Strategies Useful for the Chemical Synthesis of Oligonucleotides and Related Compounds"; Frontiers in Organic Chemistry; 2005; pp. 3-38; vol. 1.

* cited by examiner

PROCESS FOR THE SYNTHESIS OF OLIGONUCLEOTIDES

CROSS REFERENCE TO RELATED APPLICATIONS

This application is a non-provisional application of U.S. Patent Application Ser. No. 60/825,175, filed on Sep. 11, 2006, which is hereby incorporated by reference in its entirety.

FIELD OF THE INVENTION

The present invention relates to the field of nucleotide chemistry. More specifically, the invention relates to improved methods and compositions in the field of oligonucleotide synthesis. Oligonucleotides synthesized using the methods of the invention are useful as research reagents and as diagnostic reagents, and in therapeutics.

BACKGROUND OF THE INVENTION

The enormous increase in demand for synthetic oligonucleotides, fueled by the advances in DNA technology over the last decades, has been accelerated by recent progress in sequencing and decoding whole genomes, particularly the human genome. A number of methods in molecular biology and DNA based diagnostics to amplify, detect, analyze and quantify nucleic acids are dependent on chemically synthesized oligonucleotides. For instance, oligonucleotides are widely used as primers in PCR and in sequencing, and as probes in homogeneous assays or as components of microarrays. Synthetic oligonucleotides are also increasingly used in therapeutics as active pharmaceutical ingredients. For instance, oligonucleotides are used as antisense reagents with the aim to block the expression of certain proteins, as transcription factor inhibitors to block the translation of genetic information into messenger RNA, as aptamers to selectively inhibit proteins, as siRNA reagents to destroy the messenger RNA of a specific target, or as snRNA reagents to interfere in several aspects of the regulation of protein expression. Synthetic oligonucleotides are also used to store information in approaches towards molecular computing and in brand protection strategies.

A variety of methods have been developed for the chemical synthesis of oligonucleotides. The most prominent and in a commercial context almost exclusively used method is the automated solid phase synthesis using phosphoramidite chemistry, as disclosed by Caruthers et al. U.S. Pat. Nos. 4,415,732; 4,458,066; 4,500,707; 4,668,777; 4,973,679; and 5,132,418, and Köster et al. U.S. Pat. No. Re. 34,069, and described by McBride et al. (1983) Tetrahedron Letters 24:245-248 and Sinha et al. (1983) Tetrahedron Letters 24:5843-5846. The nucleoside phosphoramidite mediated synthesis of oligonucleotides has been reviewed by Beaucage et al. (1992) Tetrahedron 48:2223-2311; (1993) Tetrahedron 49:6123-6194, and Tsukamoto et al. (2005) Frontiers in Organic Chemistry 1:3-40. In this method nucleotides are sequentially attached to a solid support in a predetermined order via their nucleoside phosphoramidite derivatives. Each attachment is conducted as a series of reaction steps, collectively called a synthesis cycle, which are performed in an automated synthesis machine, i.e. a synthesizer, which delivers the required reactants to the solid support in a pre-programmed manner. In the most common version of the phosphoramidite mediated synthesis of oligonucleotides phosphoramidites (1) are employed.

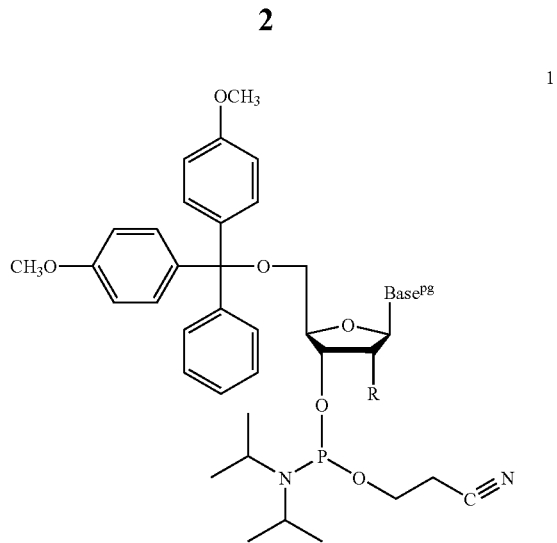

In (1) the 5'-hydroxyl function of the nucleoside is protected with a dimethoxytrityl (DMT)-protective group, which constitutes the front end protective group in the synthesis of oligonucleotides on a solid support. $Base^{pg}$ represents a nucleobase wherein the exocyclic amino group is protected with a base-labile protective group, e.g. $Base^{pg}$ represents N6-benzoyladenine, N4-acetylcytosine, N2-isobutyrylguanine or thymine, and R represents either a hydrogen atom, a protected hydroxyl group, an alkoxy group, e.g. R represents a methoxy group or a 2-methoxyethoxy group, or a fluorine atom. The synthesis cycle for the attachment of a nucleotide to the support via a phosphoramidite (1) includes the following reactions:

1. Front end deprotection/Detritylation
   Treatment of the solid support with a solution of a strong protic acid in an unpolar solvent, e.g. trichloroacetic acid in dichloromethane or dichloroacetic acid in toluene, to remove the DMT protective group in order to generate an unprotected hydroxyl group on the support.

2. Phosphoramidite coupling
   Treatment of the support with a mixture of (1) and an activator in acetonitrile to covalently bind the nucleotide of the phosphoramidite to the support. 1H-Tetrazole, 4,5-dicyanoimidazole, 5-ethylthio-1H-tetrazole and 5-(3,5-bis(trifluoromethyl)phenyl)-1H-tetrazole are commonly employed activators. The resultant product is a nucleoside phosphite triester.

3. Phosphite oxidation
   Treatment of the support with an oxidizing solution, preferably a solution of iodine, a mild base and water in a dipolar aprotic solvent, e.g. a 0.1 M iodine solution in pyridine/water/THF, to oxidize the phosphite triester to a phosphate triester. The application of a thioating reagent, e.g. 3H-1,2-benzodithiole-3-one 1,1-dioxide ('Beaucage reagent') or phenylacetyl disulfide in the phosphite oxidation steps results in the formation of respective thiophosphate triesters.

4. Capping
   Treatment with a capping reagent which blocks unreacted functional groups on the support in order to prevent their participation in further coupling reactions. Most commonly a mixture of acetic anhydride with a catalyst in a dipolar aprotic solvent is employed, optionally supplemented by a mild base, e.g. a solution of acetic anhydride, N-methylimidazole and pyridine 1/1/1, v/v, in THF. Capping may also be performed before the oxidation step in the synthesis cycle. The capping reaction can be omitted in case of high coupling yields.

For small synthesis scales, i.e. scales of 1 μmol or less, the detritylation, oxidation and capping reactions can be performed in less than one minute. The time required for the coupling reaction depends on the type of phosphoramidite, on the activator employed, and the concentrations of phosphoramidite and activator. The coupling time may range from less than one minute for DNA phosphoramidites to several minutes for RNA phosphoramidites. E.g. appr. 5 minutes coupling time are required for RNA phosphoramidite couplings wherein the 2'-protective group is tert-butyldimethylsilyl and a 0.25 M solution of 5-(3,5-bis(trifluoromethyl)phenyl)-1H-tetrazole is applied as the activator.

The solid support of the synthesis typically consists of a derivatized inorganic or organic polymer, e.g. derivatized controlled pore glass (CPG) or polystyrene, with a linker to the first nucleoside, which is cleavable with base. After the completion of the desired number of synthesis cycles the linker is cleaved with base, typically an aqueous solutions of ammonia or methylamine, and the released oligonucleotide is separated from the support and further processed. Such processing includes the removal of the nucleobase and phosphate protective groups with base, which may be performed simultaneously with the cleavage of the linker to the support, the removal of protective groups on the 2'-hydroxy function of ribonucleosides, and the purification of the oligonucleotide by precipitation, desalting and/or chromatography.

The above method has been extensively applied in research laboratories as well as for the custom synthesis of oligonucleotides in commercial laboratories, or at larger scales, e.g. at scales of 1 mol or more, for the synthesis of therapeutic oligonucleotides. The method has, however, inherent weaknesses, which are based on the properties of the DMT protective group.

The cleavage of the DMT-group with acids is a reversible reaction and the primary cleavage product, i.e. the DMT-cation, can therefore reattach itself to the hydroxyl group on the support resulting in incomplete detritylations. Any non-deprotected hydroxyl groups cannot participate in the following phosphoramidite coupling reaction, but are most likely detritylated in the following synthesis cycle. As a result, a deletion sequence is built on the support, i.e. an oligonucleotide wherein one or more of the nucleotide units in the middle of the chain are omitted. Such a deletion sequence is cleaved from the solid support at the end of the synthesis and further processed together with the desired full-length product oligonucleotide. Most deletion sequences have very similar properties as the desired oligonucleotide products, because they differ from the product only in one missing nucleotide unit. They are therefore difficult to remove from the product through conventional purification techniques. Crude (unpurified) oligonucleotide synthesis products typically have deletion sequences as prominent impurities. Deletion sequences are particularly visible as 'n−1' signals in anion-exchange chromatograms. The side product representing the 'n−1' signal of an oligonucleotide synthesis has been analyzed by Fearon et al. (1995) Nucleic Acids Res. 23:2754-2761, and by Temsamani et al. (1995) Nucleic Acids Res. 23:1841-1844, and has been shown to consist of mixtures of all possible deletion sequences of the respective full-length product sequences.

The main strategy applied today to drive the deprotection of the DMT-group to completion is the removal of the DMT-cation from the reaction equilibrium. On solid supports this is accomplished through multiple replacements of the reaction solution with fresh reagent solution, often through permanent washing of the support with fresh detritylating reagent during the reaction. Detritylation efficiencies in excess of 99% are often achieved through this technique, but relatively large volumes of the aggressive and harmful reagent solutions are consumed. Also, although the detritylation is nearly complete, a small fraction of the DMT-groups always remains undetritylated in every synthesis cycle, giving rise to an accumulating pool of deletion sequences, which then become impurities in the crude oligonucleotide synthesis product.

Another drawback of the method is the repeated exposition of the growing oligonucleotide chain to strong protic acid. Protic acids cause side reactions, in particular depurinations, which result in chain scission during the deprotection with base at the end of the synthesis. Although the current detritylating reagents are optimized with respect to high detritylation efficiency versus low depurination rates the side reaction still takes place in each cycle. In particular, purines, which are introduced in the early synthesis cycles, have multiple exposures to the acidic reagent and are partially depurinated at the end of the synthesis.

Another drawback of the use of the DMT group for front-end protection is the inherent susceptibility of this group to partial cleavage during the phosphoramidite coupling reaction. The coupling reaction is performed in the presence of an excess of slightly acidic activators, which partially cleave the DMT-group of the coupling product on the support. The resulting cleavage products can participate in further coupling reactions which in turn leads to the formation of sequences with inserted additional nucleosides, i.e. longer oligonucleotides.

All of the above drawbacks become more severe with increasing chain length of the synthesized oligonucleotide. Deletions sequences and sequences with additional inserted nucleosides accumulate to a larger extend in longer sequences than in shorter sequences and are also more difficult to remove from longer sequences than from shorter sequences. The consumption of harmful and environmentally undesired solvents and acidic reagents is linearly related to the number of synthesis cycles in the preparation of an oligonucleotide. The exposure time of a given nucleotide unit of the growing oligonucleotide to acid also relates linearly to the number of synthesis cycles. The total exposure of the growing chain to acid, as determined by adding the number of exposed nucleotide units in the growing chain at each synthesis cycle to an exposure sum, however, increases in a much stronger than linear manner with increased cycle number and may pose a limit to the length of oligonucleotides, which can be synthesized in practical terms with the method described above.

Several attempts were described to utilize alternative front-end protective groups instead of the DMT-group in a phosphoramidite mediated solid phase synthesis. In one approach a silyl group, in particular the bis(trimethylsilyloxy)cycloundecanoxysilyl group, is applied, as described by Scaringe et al. (1998) J. Am. Chem. Soc. 120:11820-11821 for phosphoramidites with methyl phosphate protective groups in the synthesis of RNA oligonucleotides. The silyl groups are removed with the highly toxic hydrofluoride-triethylamine complex or similar hydrofluoride reagents and are not compatible with the common β-cyanoethyl phosphate protective group. In another approach the monomethoxytritylthio group is applied instead of the DMT-group, as described by Seio et al. (2001) Tetrahedron Letters 42:8657-8660 in the synthesis of the 5-mer $dT_5$. The monomethoxytritylthio group is removed under oxidative conditions with a solution of 0.1 M iodine in acetonitrile/pyridine/water (10/9/1, v/v) and allows simultaneous deprotection and oxidation within a synthesis cycle. A demonstration of the usefulness of this approach was limited to the synthesis of a single, short sequence dT$_5$, which was obtained in a relatively low yield. In another approach the 2-(levulinyloxymethyl)-5-nitrobenzoyl group is applied instead of the DMT-group, as described by Kamaike et al. (1997) Tetrahedron Letters 38:6857-6860 in the synthesis of an RNA 8-mer. The 2-(levulinyloxymethyl)-5-nitrobenzoyl group is removed on the support in a two-step procedure consisting of a treatment with a solution of hydrazine hydrate for 15 minutes followed by a treatment with a solution of imidazole for 5 minutes. The rather long deprotection time, the need for two different deprotection reagents and the carcinogenic nature of the first reagent are drawbacks of this method.

In some known methods alternative front end protective groups to the DMT-group are applied in the phosphoramidite method, which are cleaved under basic conditions. In one example the 2-dansylethoxycarbonyl group was applied instead of the DMT-group for deoxyribonucleoside phosphoramidites with p-nitrophenylethyl phosphate protective groups as described by Bergmann et al. (1994) Helv. Chim. Acta 77:203-215 for the synthesis of homopolymers of dA, dC, dG and dT with a length up to 10 nucleotide units. The 2-dansylethoxycarbonyl group is cleaved with a 0.1 M solution of DBU in acetonitrile within 140 sec., presumably through a β-elimination mechanism. In another example the (2-cyano-1-phenyl)ethoxycarbonyl group was applied instead of the DMT-group for ribonucleoside phosphoramidites with p-nitrophenylethyl phosphate protective groups as described by Münch et al. (1997) Nucleosides & Nucleotides 16:801-808. The (2-cyano-1-phenyl) ethoxycarbonyl group is cleaved with a 0.1 M solution of DBU in acetonitrile within 20 sec., presumably through a β-elimination mechanism. The highly reactive 1-phenylacrylonitrile is formed as a by-product in this approach, which may react with nucleobases. In another approach the p-phenylazophenyloxycarbonyl group is applied instead of the DMT-group for deoxyribonucleoside phosphoramidites with methyl phosphate protective groups as described by Seliger et al. (1985) Nucleosides & Nucleotides 4:153-155 for the synthesis of short poly-dt sequences. The p-phenylazophenyloxycarbonyl group is removed through a two-step reaction sequence, which involves treatment with a mixture of 2-cyanoethanol, triethylamine and water 1/1/1, v/v, for 1 minute, followed by a treatment with a mixture of DBU and pyridine 1/1, v/v, for 1 minute. The proposed mechanism of cleavage involves a transesterification to generate the respective β-cyanoethoxycarbonyl compounds followed by β-elimination. A rather low yield of poly-dT sequences with lengths up to 9-nucleotides was obtained. In another approach substituted aryloxycarbonyl groups, preferable 3-trifluoromethylphenyloxycarbonyl groups, were applied instead of the DMT-group for deoxyribonucleoside phosphoramidites with β-cyanoethyl phosphate protective groups as described by Sierzchala et al. (2003) J. Am. Chem. Soc. 125:13427-13441; U.S. Pat. No. 6,222,030. The 5'-aryloxycarbonyl groups are removed with a buffered solution of lithium hydroxide, hydrogen peroxide and m-chloroperbenzoic acid in a solvent cocktail containing 2-amino-2-methyl-1-propanol and water at pH 9-10 in this method. The cleavage of the 5'-protective groups is presumably accomplished with peroxyanions formed in the deprotection solution, which act as strong nucleophiles. In this approach the phosphite oxidation reaction of the synthesis cycle is carried out at the same time as the front end deprotection reaction, because the peroxy anions also represent mild oxidizing agents. The method has also been applied in the simultaneous synthesis of a multitude of oligonucleotides on flat surfaces, i.e. in the synthesis of microarrays. The deprotection solution containing peroxyanions is, however, not stable and needs to be freshly prepared every day. In another approach the DMT group was replaced by the 9-fluorenylmethyloxycarbonyl (Fmoc) group for ribonucleoside phosphoramidites with β-cyanoethyl phosphate protective groups as described by Lehmann et al. (1989) Nucleic Acids Res. 17:2379-2390. The Fmoc group is cleaved with a 0.1 M solution of DBU in acetonitrile in this approach, presumably via a β-elimination mechanism. In this approach the highly reactive dibenzofulvene is generated as a by-product, which may lead to reactions with nucleobases or may polymerize and cause clogging of solvent lines or filters on a synthesizer. Also, the stepwise coupling yields were limited to 96% in the described synthesis, which is not high enough for the synthesis of long oligonucleotides.

In all of the methods cited above wherein alternative front end protective groups to the DMT-group are cleaved under basic conditions the respective protective groups represent alkyloxycarbonyl- or aryloxycarbonyl groups. Also, in all of these methods the mechanism of cleavage for the respective protective group is either cleavage via β-elimination or cleavage with strong nucleophiles. In the present invention other alternative protective groups to the DMT-group are disclosed, which represent acyl groups, and which are cleaved with organic bases like primary amines or phenolates. Furthermore, the present invention discloses phosphoramidites for the solid phase synthesis of oligonucleotides wherein the front end protective group is a base labile protective group, which is an acyl group, and which is cleaved with an organic base like a primary or secondary amine. Also, the present invention discloses methods for the synthesis of oligonucleotides, which are based on the application of the above phosphoramidites in the phosphoramidite-mediated synthesis of oligonucleotides on solid supports.

SUMMARY OF THE INVENTION

Among the various aspects of the present invention is the provision of a method for the solid phase synthesis of oligonucleotides utilizing nucleoside phosphoramidites having base labile, front end protective groups. In particular, a base labile, front end protective group comprises an acyl group. Each synthesis cycle of the method comprise cleaving the front end protective group from the nucleoside immobilized on the solid support with a reagent comprising an organic base. The organic base may be a primary amine, a secondary amine, or a mixture thereof. Each synthesis cycle also comprises the coupling of an acyl protected nucleoside phosphoramidite with the free hydroxyl group of the unprotected nucleoside immobilized on the solid support.

Another aspect of the present invention encompasses a nucleoside phosphoramidite comprising an acyl front end protective group and a phosphoramidite. The acyl front end protective group of the nucleoside phosphoramidite is cleavable with an organic base in 10 minutes or less at room temperature. The organic base may be a primary amine, a secondary amine, or a mixture thereof.

Other aspects and features of the invention are described in more detail herein.

DETAILED DESCRIPTION OF THE INVENTION

Figure 1A:
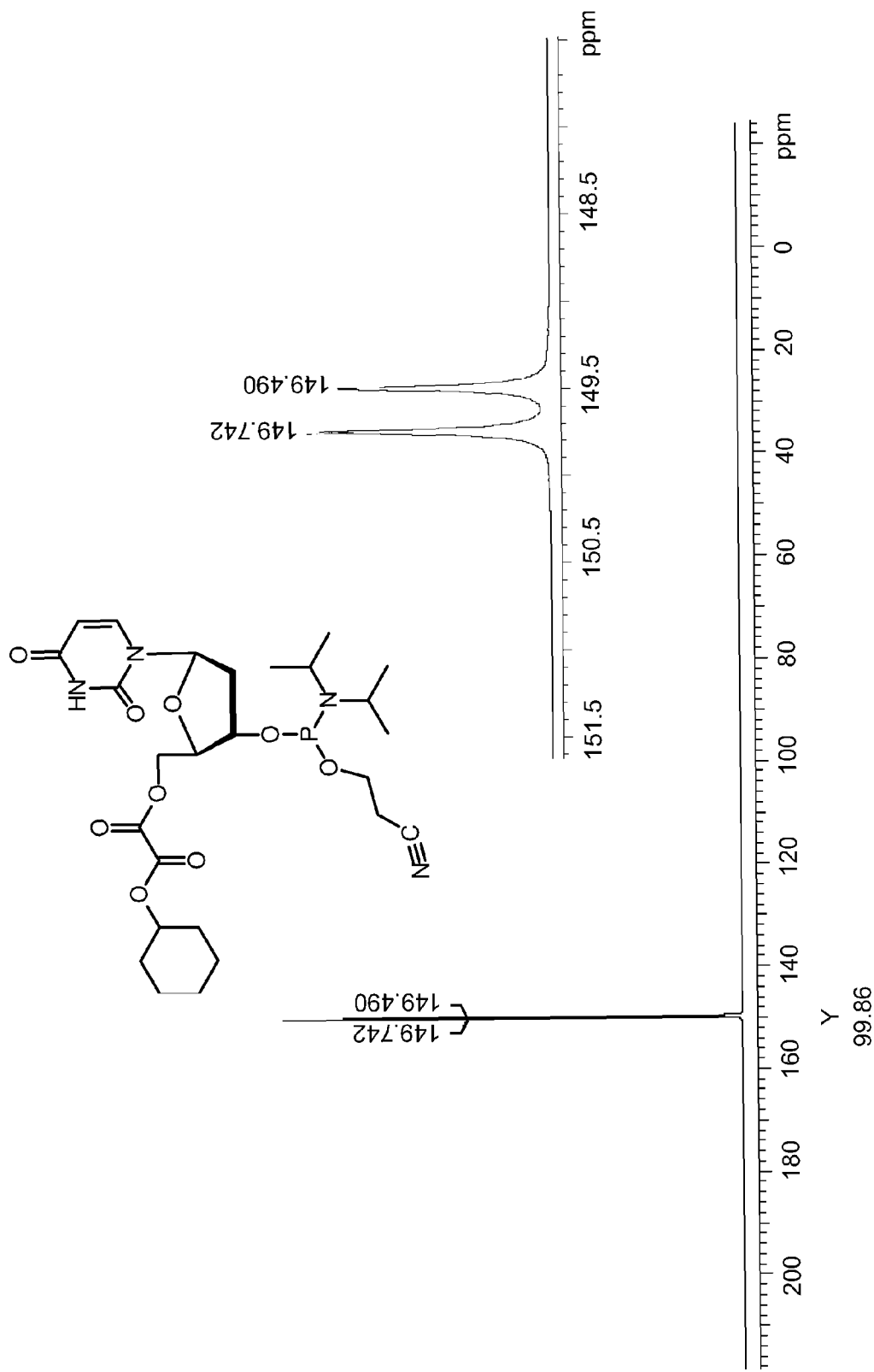
FIG. 1 displays the $^{31}$P-NMR spectra of 5'-acyl phosphoramidites. Panel A presents that of CyOX-dT-β-cyanoethylamidite (10). Panel B presents that of PSNp-dT-β-cyanoethyl-amidite (11). Inserts are included which display expansions of the spectra for the main signals in order to demonstrate the absence of P(III)-impurities.

Various terms are used herein to refer to aspects of the present invention. To aid in the clarification of the description of the components of the invention, the following descriptions are provided. It is to be noted that the term "a" or "an" entity refers to one or more of that entity; for example, an oligonucleotide refers to one or more oligonucleotides. As such, the terms "a" or "an", "one or more" and "at least one" are used interchangeably herein.

The term "oligonucleotide" as used herein refers to a single stranded chain of either deoxyribonucleotides, e.g. the nucleotides of deoxyadenosine, deoxycytidine, deoxyguanosine and thymidine, or ribonucleotides, e.g. the nucleotides of adenosine, cytidine, guanosine and uridine, or chemical modifications thereof, such as e.g. nucleotides with a 2'O-4'C-methylene bridge in their sugar portion, which are the constituting nucleotides of locked nucleic acids (LNA). The modifications include, but are not limited to, those that provide other chemical groups that incorporate additional charge, polarizability, hydrogen bonding, electrostatic interaction, and functionality to the individual nucleotides or their corresponding bases or to the oligonucleotides as a whole. Such modifications include, but are not limited to, modified bases, 2'-position sugar modifications, 5-position pyrimidine modifications, 8-position purine modifications, modifications at cytosine exocyclic amines, methylations, bases that can be part of unusual base-pairing combinations such as the isobases isocytidine and isoguanosine and the other modifications known to those skilled in the art. The modifications further include attached labels and reporter molecules, such as fluorescent dyes, biotin, minor groove binders and the like that are known to those skilled in the art. In addition, the modifications include modified backbones of the oligonucleotides, examples being phosphorothioate DNA, methylphosphonate DNA and other modifications known to those skilled in the art as reviewed by Micklefield (2001) Current Medicinal Chemistry 8:1157-1179. Oligonucleotides, as referred to in this invention can consist of any combinations of the nucleotides and their modifications described above and can have either a few, e.g. up to 6, or many, e.g. 6 to several hundred or more, nucleotides incorporated in their chain.

The term "nucleobase" as used herein refers to the heterocyclic moiety of a nucleoside, e.g. adenine in adenosine, cytosine in cytidine, guanine in guanosine and uracil in uridine. The term nucleobase is not restricted to the most abundant heterocyclic moieties in natural nucleic acids, but includes heterocyclic moieties of nucleosides which occur rarely in nature or are not present in nature, such as, e.g. 5-methylcytosine in 5-methylcytidine, hypoxanthine in inosine, uracil in pseudouridine and the like that are known to those skilled in the art. The concept of nucleobases is not limited to ribonucleosides and deoxyribonucleosides, but includes, without being limited to, 2'-O-alkyl nucleosides, nucleotides with a 2'O-4'C-methylene bridge in their sugar portion (LNA nucleosides), 2'-deoxy-2'-fluoro nucleosides and the like.

The term "nucleobase protective group" as used herein refers to a protective group applied to a functional group of a nucleobase, in particular to exocyclic amino groups or lactam groups of the respective heterocyclic moieties. The concept of nucleobase protective groups applies to, but is not limited to protective groups on the N6-amino groups of adenine moieties, on the N4-amino group of cytosine moieties, on the N2-amino groups and N1/O6-lactam groups of guanine moieties, and on the N3/O4-lactam groups of uracil and thymine moieties. Nucleobase protective groups are used in order to prevent side reactions at nucleobases during the synthesis of oligonucleotides and are typically removed at the end of the oligonucleotide synthesis. Nucleobase protective groups as used herein can be either base-labile or acid labile or can be protective groups which are removed with other reagents than bases or acids.

The term "nucleoside phosphoramidite" as used herein refers to a compound of either formula (2) or formula (3)

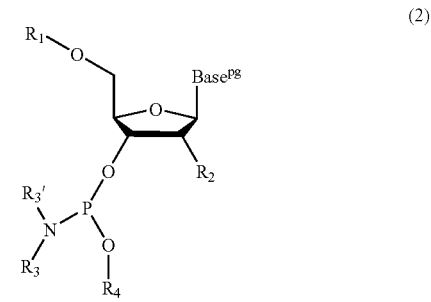

(2)

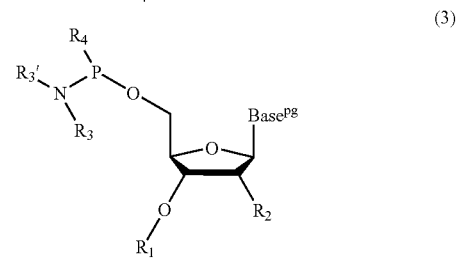

(3)

wherein $Base^{pg}$ denotes a nucleobase with an optional nucleobase protective group $R_1$ denotes a protective group $R_2$ denotes a hydrogen atom, a protected hydroxy group, an alkoxy group or a fluorine atom; the respective nucleoside phosporamidites are deoxyribonucleoside phosphoramidites, ribonucleoside phosphoramidites, 2'-O-alkyl ribonucleoside phosphoramidites and 2'-deoxy-2'-fluoro ribonucleoside phosphoramidites $R_3$ and $R_3'$ denote alkyl groups, including, but not limited to methyl, ethyl, isopropyl and higher alkyl; R3 and $R_3'$ may together form a cyclic alkylene group having from two to up to twenty carbons which may or may not have additional alkyl substituents attached to it and which may contain up to 3 heteroatoms selected from N, O and S included in the cyclic alkylene group; preferably, $R_3$ and $R_3'$ denote isopropyl groups $R_4$ denotes a phosphorus protective group, e.g. a β-cyanoethyl group, a methyl group, a benzyl group, an allyl group, a 2-(p-nitrophenyl)-1-ethyl group, a 4-methylthio-1-butyl group, a 2-(N-acetyl) amino-1-ethyl group, a 2-naphthylcarbamoyloxy-1-ethyl group or any other phosphorus protective group known to those skilled in the art; preferably $R_4$ denotes a β-cyanoethyl group The term "synthesis cycle" as used herein refers to a series of reaction steps which are conducted in short succession in the phosphoramidite mediated solid phase synthesis of oligonucleotides in order to attach one nucleotide to the solid support. An oligonucleotide synthesis comprises several similar synthesis cycles with different phosphoramidites, which results in the assembly of the oligonucleotide chain on the support. A synthesis cycle consists of:

1. A "front-end deprotection reaction"
   which, as used herein, refers to the removal of a front end protective group on the solid support to liberate a nucleoside hydroxyl group on the support. In the phosphoramidite mediated synthesis of oligonucleotides with phosphoramidites (2) or (3) the front end protective group is the group $R_1$, in an oligonucleotide synthesis with phosphoramidite (1) the front end protective group is a DMT-group which is cleaved with protic acids.

2. A "phosphoramidite coupling reaction"
   which, as used herein, refers to the reaction of a phosphoramidite (2) or (3) with a hydroxyl group on the solid support in the presence of an activator like 1H-tetrazole, 4,5-dicyanoimidazole, 5-ethylthio-1H-tetrazole and 5-(3,5-bis(trifluoromethyl)phenyl)-1H-tetrazole or another activator known to those skilled in the art. The resultant reaction product is a phosphite triester which is attached to the solid support.

3. A "phosphite oxidation reaction"
   which, as used herein, refers to the oxidation of the phosphite triester reaction product obtained in a phosphoramidite coupling reaction to a phosphate triester. A phosphite oxidation reaction can be performed with a variety of oxidants including iodine/water, peroxides such as tert.-butylhydroperoxide, cumol hydroperoxide, 2-butanone peroxide or bis(trimethylsilyl) peroxide, (1S)-(+)-(10-camphorsulfonyl)oxaziridine and other oxidants known to those skilled in the art. Preferably, phosphite oxidation reactions are conducted with solutions of iodine and water in a mixture of an aprotic solvent with a mild base like pyridine or 2,6-lutidine.

4. A capping reaction
   with a reagent that reacts with residual hydroxyl groups on the solid support after the phosphoramidite coupling reaction and thereby blocks these hydroxyl groups from future reactions. The capping reaction reduces the generation of deletion sequences resulting from incomplete phosphoramidite coupling reactions. In case of very high yields of phosphoramidite coupling reactions the capping reaction has very little influence on the quality of the oligonucleotide product and is therefore sometimes omitted. The capping reaction can also be performed before the phosphite oxidation reaction. Reagents applied in capping reactions include, but are not limited to acetic anhydride in the presence of a nucleophilic catalyst like N-methylimidazole and non-nucleoside phosphoramidites such as β-cyanoethyl-diisopopylamino-methoxyethoxyethoxyphosphane in the presence of an activator as in nucleoside phosphoramidite coupling reactions. A great variety of non-nucleoside phosphoramidites is suitable as capping reagent in conjunction with an activator.

In some instances two of the reaction steps of a synthesis cycle can be performed simultaneously, which is within the scope of the present invention. For example, the front end deprotection reaction and the phosphite oxidation reaction can be performed simultaneously if the deprotection reagent applied in the front end deprotection reaction constitutes an oxidant, as described by Sierzchala et al. (2003) J. Am. Chem. Soc. 125:13427-13441, or the phosphite oxidation reaction can be performed simultaneously with the capping reaction, as described by Song et al. (2003) Nucleosides, Nucleotides & Nucleic Acids 22:629-633; U.S. Pat. No. 6,609,195 B1.

The term "acyl group" as used herein refers to a group of formula (4) which comprises a carbonyl group and an attached substituent R wherein R is attached to the carbonyl group via a carbon atom. Examples for R include alkyl-, alkylcarbonyl and alkoxycarbonyl-groups wherein the alkyl substituents contain from 1 up to 20 carbon atoms and may be straight chain or branched chain alkyl groups including cycloalkyl groups with or without heteroatoms in the cycloalkyl moieties, and wherein the alkyl substituents also contain optional non-carbon substituents like halogen atoms and optional functional groups like cyano-, carbalkoxy-, alkoxy-, protected hydroxy-groups or other functional groups known to those skilled in the art, and wherein the alkyl substituents also contain optional ether groups. Other examples of acyl groups in the spirit of the present invention are aryl-, arylcarbonyl-, or aryloxycarbonyl-groups wherein the aryl substituents are derived from benzene or from condensed hydrocarbon ring systems including, but not limited to naphthalene, anthracene, phenanthrene, pyrene, or wherein the aryl substituents are derived from heterocycles with one or more heteroatoms in the ring system and are either single ring systems or condensed ring systems including, but not limited to pyrrole, imidazole, triazole, pyridine, furane, quinoline, isoquinoline, carbazole other heterocycles known to those skilled in the art, and wherein the aryl substituents contain optional substituents or functional groups attached to their respective ring system like alkyl-, halogenoalky-, aryl-, halogeno-, nitro, alkyloxycarbonyl-, aryloxycarbonyl, cyano-substituents or other substituents or functional groups known to those skilled in the art. Acyl groups as used herein are not limited to the examples given above and include groups with other substituents R, for instance alkenyl- and alkinyl-groups, and are solely limited by way of the attachment of the substituent R to the carbonyl group of the acyl group, which occurs via a carbon atom.

(4)

The terms "primary amine" and "secondary amine" as used herein refer to an amine R—$NH_2$ or R,R'—NH respectively, wherein R and R' represent alkyl groups with 1 to 20 carbon atoms. The alkyl groups may be straight chain or branched chain alkyl groups or cycloalkyl groups with or without heteroatoms in the cycloalkyl moiety. The alkyl groups may contain optional non-carbon substituents like halogen substituents and optional functional groups like cyano-, carboxamide-, alkoxy-, protected hydroxy-groups or other functional groups known to those skilled in the art, and may also contain optional ether groups. The alkyl groups may also contain additional amino groups which may be primary, secondary or tertiary amino groups. Examples of primary amines as used herein include, but are not limited to n-butylamine, tert.-butylamine, n-hexylamine, 2-methoxyethylamine, ethylene diamine, 2-(N,N-diethylamino)ethylamine, cyclohexylamine and the like. Examples of secondary amines as used herein include, but are not limited to diethylamine, di-n-propylamine, 1,2-dimethylethylene diamine and the like. The alkyl groups R and R' in secondary amines may or may not be identical.

The term "solid support" as used herein refers to a polymer, that is insoluble in the media employed in the reaction steps performed to synthesize oligonucleotides, and is derivatized to comprise hydroxyl groups. The polymer can be an inorganic polymer, including, but not limited to silica, alumina and controlled pore glass (CPG), or an organic polymer, including, but not limited to polystyrene, polyacrylamide, polymethacrylate, polyvinylalcohol, or other synthetic polymers, carbohydrates such as cellulose and starch or other polymeric carbohydrates, or other organic polymers and any copolymers, composite materials or combination of the above inorganic or organic materials. The hydroxy groups of a solid support may be unprotected or protected, e.g. with a DMT-protective group, or with another hydroxyl group protective group. During oligonucleotide synthesis a solid support is treated with various reagents in several synthesis cycles to achieve the stepwise elongation of a growing oligonucleotide chain with individual nucleotide units. The nucleoside unit at the end of the chain which is directly linked to the solid support is termed "the first nucleoside" as used herein. The first nucleoside is bound to the solid support via a linker moiety, i.e. a diradical with covalent bonds to both the polymer of the solid support and the nucleoside. The linker stays intact during the synthesis cycles performed to assemble the oligonucleotide chain and is cleaved after the chain assembly to liberate the oligonucleotide from the support.

The term "acidic reagent" as used herein refers to an acidic solution. Acidic solutions in this context may be aqueous solutions with a pH of less than 7, e.g. the solution of a protic acid in water or a buffer solution with a pH of less than 7, or non-aqueous solutions, e.g. the solution of an acid in an organic solvent. Examples of acidic reagents include, but are not limited to diluted mineral acids, e.g. 0.01 M hydrochloric acid in water or 0.01 M sulfuric acid in water, mixtures of carboxylic acids with water, e.g. 80% acetic acid in water or 40% formic acid in water, aqueous citrate buffers, e.g. citrate buffer pH 3, aqueous acetate buffer, e.g. acetate buffer pH 4, solutions of dichloroacetic acid in organic solvents, e.g. 3% dichloroacetic acid in dichloromethane or toluene, solutions of acetic acid in dichloromethane, e.g. 10% acetic acid in dichloromethane, and the like.

The term "acid labile linker" as used herein refers to a linker moiety which is susceptible to cleavage with an acidic reagent.

The term "2'-protective group" as used herein refers to a protective group applied to the 2'-hydroxy group of ribonucleosides. In particular, the term 2'-protective group refers to the protective group $R_2$ for nucleoside phosphoramidites in formulae (2) and (3). The cleavage of 2'-protective groups is orthogonal to the cleavage of front end protective groups in an oligonucleotide synthesis, i.e. they stay intact during the synthesis cycles on the solid support and are collectively removed after the chain assembly. Preferably, the 2'-protective groups are removed simultaneously with the cleavage of the linker to the support and with the removal of nucleobase protective groups.

The extension of an oligonucleotide chain during a phosphoramidite mediated synthesis on a solid support is typically pursued in the 3' to 5' direction with phosphoramidites (2). During synthesis with (2) the front end protective group is removed from the 5'-position and the subsequent coupling occurs between a support-bound 5'-hydroxy group and a 3'-phosphoramidite group of (2). The extension of the oligonucleotide chain may alternatively be pursued in the 5' to 3' direction with phosphoramidites (3). During synthesis with (3) the front end protective group is removed from the 3'-position and the subsequent coupling occurs between a support-bound 3'-hydroxy group and a 5'-phosphoramidite group of (3). The latter approach is exemplified in the synthesis of oligodeoxynucleotides with 3'-DMT protected deoxynucleoside 5'-phosphoramidites, as described by e.g. Robles et al. (1995) Nucleic Acids Res. 23:4151-61 (1995). The synthesis cycles for the chain elongation in 3' to 5' direction and the chain elongation in 5' to 3' direction are nevertheless very similar, if not identical for a given type of employed phosphoramidites. Any feature of the present invention described in this disclosure for the chain elongation in 3' to 5' direction is therefore directly applicable to chain elongation in 5' to 3' direction and chain elongation in 5' to 3' direction is consequently well within the breath and scope of the invention.

Phosphoramidites which are applied in the coupling step of an oligonucleotide synthesis cycle are typically monomer phosphoramidites, i.e. they contain one nucleoside unit as displayed in formulae (2) and (3). It has nevertheless been demonstrated that suitably constructed dimer phosphoramidites, i.e. phosphoramidites derived from dinucleotides as described by Kumar et al. (1984) J. Org. Chem. 49:4905-12, or trimeric phosphoramidites, i.e. phosphoramidites derived from trinucleotides as described by Ono et al., Nucleic Acids Res. 23, 4677-82 (1995), can be applied successfully in a phosphoramidite mediated synthesis of oligonucleotides on a solid support. The synthesis cycles for monomeric, dimeric, trimeric and possibly higher oligomeric phosphoramidites are nevertheless very similar to each other, if not identical, provided the type of employed phosphoramidite as defined through the nature of the groups $R_1$, $R_2$, $R_3$, $R_3'$ and $R_4$ in (2) and (3) is identical. Any feature of the present invention described in this disclosure for the use of monomeric phosphoramidites is therefore directly applicable to the use of dimeric, trimeric or higher oligomeric phosphoramidites in the synthesis of oligonucleotides on solid supports. The application of dimeric, trimeric or higher oligomeric phosphoramidites in the synthesis of oligonucleotides on solid supports is consequently well within the breath and scope of the invention.

The present invention discloses novel nucleoside phosphoramidites which are useful for the synthesis of oligonucleotides. The novel phosphoramidites of the invention are represented by formulae (2) and (3) wherein $R_1$ denotes an acyl group as defined above. The novel phosphoramidites are further characterized therein that the acyl group $R_1$ is cleavable in a synthesis cycle of the phosphoramidite mediated synthesis of oligonucleotides on solid supports with an organic base such as a primary amine, a secondary amine, or a mixture thereof.

In a preferred embodiment of the invention the nucleobase protective groups, if present, are cleavable after the assembly of the respective oligonucleotides with an acidic reagent. In another embodiment of the invention one or more of the nucleobase protective groups is cleavable under neither acidic nor basic conditions, e.g. cleavable with fluoride salts or hydrofluoric acid complexes. In yet another embodiment of the invention one or more of the nucleobase protective groups are cleavable after the assembly of the respective oligonucleotides with aqueous ammonia or an aqueous solution of methylamine, and wherein the nucleobase protective group is stable to the conditions of the front end deprotection step with amines.

In some embodiments of the phosphoramidite synthesis method protective groups for the nucleobases are not required, as demonstrated by Gryaznov et al. (1992) Nucleic Acids Res. 20:1879-82, and by Sekine et al. (2003) J. Org. Chem. 68:5478-92. In particular, in a regular phosphoramidite based oligonucleotide synthesis the guanine base does not need to be protected, see Gryaznov et al. In one embodiment of the present invention the guanine nucleobase therefore does not carry a nucleobase protective group or carries a nucleobase protective group which is either completely or partially removed under the conditions of the front end deprotection step with amines. For instance, phosphoramidites represented by formulae (2) and (3) wherein $R_1$ denotes an acyl group, base denotes guanine and pg denotes an acyl group including, but not limited to isobutyryl, acetyl or 4-(tert.-butylphenoxy)acetyl, are well within the scope of the present invention.

In a preferred embodiment of the invention, $R_3$ and $R_3'$ in formulae (2) and (3) represent diisopropylamino groups. In a particularly preferred embodiment of the invention $R_3$ and $R_3'$ in formulae (2) and (3) represent diisopropylamino groups, $R_4$ represents a β-cyanoethyl group and $R_2$ represents a hydrogen atom. In another particularly preferred embodiment of the invention $R_3$ and $R_3'$ in formulae (2) and (3) represent diisopropylamino groups, $R_4$ represents a β-cyanoethyl group and $R_2$ represents a protected hydroxy group wherein the protective group is cleavable after the assembly of the respective oligonucleotides with an acidic reagent.

The present invention also discloses methods for the synthesis of oligonucleotides wherein phosphoramidites as described above for several embodiments of the invention are applied in the synthesis cycles of the phosphoramidite mediated synthesis of oligonucleotides on solid supports. The methods are characterized therein that the acyl front end protective group applied in the phosphoramidites of the invention is removed during the front end deprotection step of a synthesis cycle by treatment of the solid support with an organic base, either a primary amine, a secondary amine, or a mixtures thereof.

Currently, the phosphoramidite mediated synthesis of oligonucleotides on solid supports is predominantly performed with phosphoramidites of general formula (1). In this method the dimethoxytrityl (DMT) group is applied as the front end protective group. The DMT group has, nevertheless, inherent disadvantages. For instance, the cleavage of the DMT group is reversible. The cleavage product is the DMT cation which may reattach to the hydroxyl group on the solid support thus rendering the deprotection reaction incomplete. Incomplete deprotections in every synthesis cycle result in the generation of a pool of deletion sequences with one or a few missing nucleotide units which accumulate in the course of the oligonucleotide chain assembly. Such deletion sequences are produced even if the deprotection yield is high. For instance, a deprotection yield of 99.5% in each synthesis cycle results in the generation of appr. 9% deletion sequences with one missing nucleotide unit (n−1 product) for a 20-mer oligonucleotide and of appr. 22% deletion sequences with one or two missing nucleotide units for a 50-mer oligonucleotide. The use of the phosphoramidites of the invention can overcome the above limitation of the DMT-group, because the cleavage of the front end protective group is irreversible for the applied acyl groups. The cleavage products obtained in the deprotection reaction of acyl groups with primary amines or secondary amines as deprotection reagents are primary or secondary amides, which can not reattach to the liberated hydroxyl groups during the deprotection reaction. Due to the reversibility of the cleavage of DMT group the deprotection yield can be increased by the removal of the DMT-cation from the reaction equilibrium. This strategy is currently extensively applied in the solid phase synthesis of oligonucleotides through the replacement of the reaction solution with fresh reagent solution, often through permanent washing of the support with reagent solution during the deprotection. As a consequence relatively large volumes of the reagent solution, in most cases solutions of either dichloroacetic acid or trichloroacetic acid in dichloromethane or toluene, are employed and subsequently discharged as halogenated chemical waste. Large consumption of deprotection reagents can be avoided through the application of the phosphoramidites of the invention, because removal of the cleavage products is not necessary in case of acyl groups.

Another drawback of the DMT-group is its mode of cleavage, which requires that the solid support is treated with a strong protic acid in every synthesis cycle. Strong protic acids cause side reactions in the synthesis of oligonucleotides, in particular depurination reactions. Depurinations are one of the main side reactions in the synthesis of oligodeoxynucleotides. The phosphoramidites and methods of the present invention overcome this limitation of the DMT-group, because repeated treatments of the growing oligonucleotide chains on the solid support are avoided. Depurinations are a particularly severe problem in the synthesis of long oligonucleotides, because the probability of a depurination increases in a much higher than linear manner with increasing chain length. The methods of the present invention therefore appear particularly suitable for the synthesis of relatively long oligonucleotides.

Another drawback of the DMT-group is its partial cleavage during phosphoramidite coupling reactions. Phosphoramidite coupling reactions are performed in the presence of slightly acidic activators, most commonly with activators having pKa values of appr. 3.5-5.3, which promotes the partial cleavage of the DMT-group in this reaction. The liberated hydroxy group of the resultant cleavage product can participate in further coupling reactions. As a consequence, insertion sequences are formed which contain addition nucleotides. Insertion sequences accumulate over the course of the chain assembly to a pool of oligonucleotide impurities with inserted nucleosides at each possible position (n+-mer' sequences). The formation of insertion sequences is facilitated through longer reaction times in phosphoramidite couplings, e.g. in couplings of ribonucleoside phosphoramidites with 2'-tert.-butyldimethylsilyl protection, and through the use of activators with higher acidity, e.g. through the use of 5-ethylthio-1H-tetrazole (pKa 4.1) compared to the use of 4,5-dicyanoimidazole (pKa 5.2). Even with very low levels of detritylation side reactions the formation of insertion sequences is problematic, because they accumulate over the course of the oligonucleotide chain reaction. For instance, an average of 0.1% detritylation in each phosphoramidite coupling reaction will result in the formation of appr. 5% 'n+-mer' sequences during the assembly of a 50-mer sequence. The problem of premature deprotection during coupling reactions is completely avoided through the methods of the present invention.

Preferably, the removal of acyl groups in the front end deprotection reaction of a synthesis cycle is conducted in not more than 10 minutes at room temperature. Even more preferred, the removal of acyl groups is conducted in not more than 1 minute at room temperature. In this disclosure examples are provided wherein the deprotection is complete in the desired time range. The deprotection reagents of the examples are particularly easy to prepare and comprise inexpensive components, such as industrial primary amines like n-butylamine, n-hexylamine, 2-methoxyethylamine or 2-(N,N-diethylamino)ethylamine and acetonitrile.

In preferred embodiments of the methods of the invention the nucleobase protective groups and the linker applied to attach the first nucleoside to the support are cleaved with an acidic reagent. In this method the oligonucleotide synthesis product is treated with an acidic reagent at the end of the chain assembly of the oligonucleotide on the support. The removal of the nucleobase protective groups and the cleavage of the acid labile linker can be performed simultaneously under suitable deprotection conditions, i.e. conditions under which the nucleobase protective groups are removed as well as the linker is cleaved. Acid labile protective groups for nucleobases have been described e.g. by Honda et al. (1984) Tetrahedron 40:153-163 and Sekine et al. (1986) J. Am. Chem. Soc. 108:4581-4586, who used monomethoxytrityl (MMT)- and DMT-groups to protect the exocyclic amino groups of adenines, cytosines and guanines. Acid labile linkers in the context of solid supported oligonucleotide synthesis have been described e.g. by Palom et al. (1993) Tetrahedron Letters 34:2195-2198.

In other preferred embodiments of the methods of the invention the 2'-protective group of phosphoramidites derived from ribonucleosides is an acid labile protective group. In this method the oligonucleotide synthesis product is treated with an acidic reagent after the chain assembly of the oligonucleotide on the support. The removal of the 2'-protective groups and the nucleobase protective groups and the cleavage of the linker of the first nucleoside to the support can be conducted simultaneously if acid labile nucleobase protective groups and an acid labile linker are employed. The application of acid labile 2'-protective groups in the synthesis of oligoribonucleotides has been extensively described. Representative examples are the application of the 4-methoxytetrahydropyranyl group by Reese et al. (1970) Tetrahedron 26:1023-1030 and Norman et al. (1984) Tetrahedron Letters 25:3015-3018, the application of the tetrahydrofuranyl group by Ohtsuka et al. (1983) Nucleic Acids Res. 11:1325-1335 and by Iwai et al (1988) Nucleic Acids Res. 16:9443-9456, the application of the 3-methoxy-1,5-dicarbomethoxypentan-3-yl group by Sandström et al. (1985) Acta Chem. Scand. B39:273-290, the application of the 1-(2-fluorophenyl)-4-methoxypiperidine-4-yl- group and the related 1-(4-chlorophenyl)-4-ethoxypiperidine-4-yl group by Rao et al. (1993) J. Chem. Soc. Perkin Trans. 1 43-55 and by Llyod et al. (2000) J. Chem. Soc. Perkin Trans. 1 165-176, and the application of the bis(2-acetoxyethoxy)methyl group by Scaringe et al. (1998) J. Am. Chem. Soc. 120:11820-11821.

The present invention is further described by way of specific examples as discussed and enclosed hereafter. The examples are offered for illustrative purposes only and are not intended to limit the invention in any manner.

The synthesis of a variety of 5'-acyl protected thymidine derivatives (6a-g) is illustrated in Scheme 1 and in Example 1. The acyl groups include the trichloroacetyl group in TCA-dT-Si (6a), the ethoxydicarbonyl group in EtOX-dT-Si (6b), the benzyloxydicarbonyl group in BnOX-dT-Si (6c), the cyclohexyloxydicarbonyl group in CyOX-dT-Si (6d), the phenoxydicarbonyl group in PhOX-dT-Si (6e), the 2-(4-nitrophenoxycarbonyl)-benzoyl group in PSNp-dT-Si (6f), and the 2-(2-cyanophenoxycarbonyl)-benzoyl group in PSCp-dT-Si (6g). A common precursor, i.e. O3'-tert.-butyldimethylsilyl-thymidine (5) was employed in all syntheses. For the derivatives (6a-e) the acyl groups were introduced via their respective acid chlorides. In case of the oxalylester derivatives (6c-e) the respective oxalyl ester acid chlorides were prepared from the corresponding alcohol or phenol and oxalylchloride. In case of the ortho-substituted benzoyl groups PSNp and PSCp in the derivatives (6f-g) the groups were introduced via a two-step reaction sequence which involved the synthesis of the 5'-phthalic acid ester derivative of (5) as an intermediate and the introduction of the 4-nitrophenylester or 2-cyanophenylester moieties with either the respective phenols and a condensing reagent, e.g. N,N'-dicyclohexylcarbodiimide in the presence of DMAP, or with active esters of the respective phenols, in particular the trifluoroacetates 4-nitrophenyltrifluoroacetate or 2-cyanophenyltrifluoroacetate, respectively. The derivatives (6a-g) were obtained in 59-86% yield and had purities of 98% or better by analytical RP-HPLC.

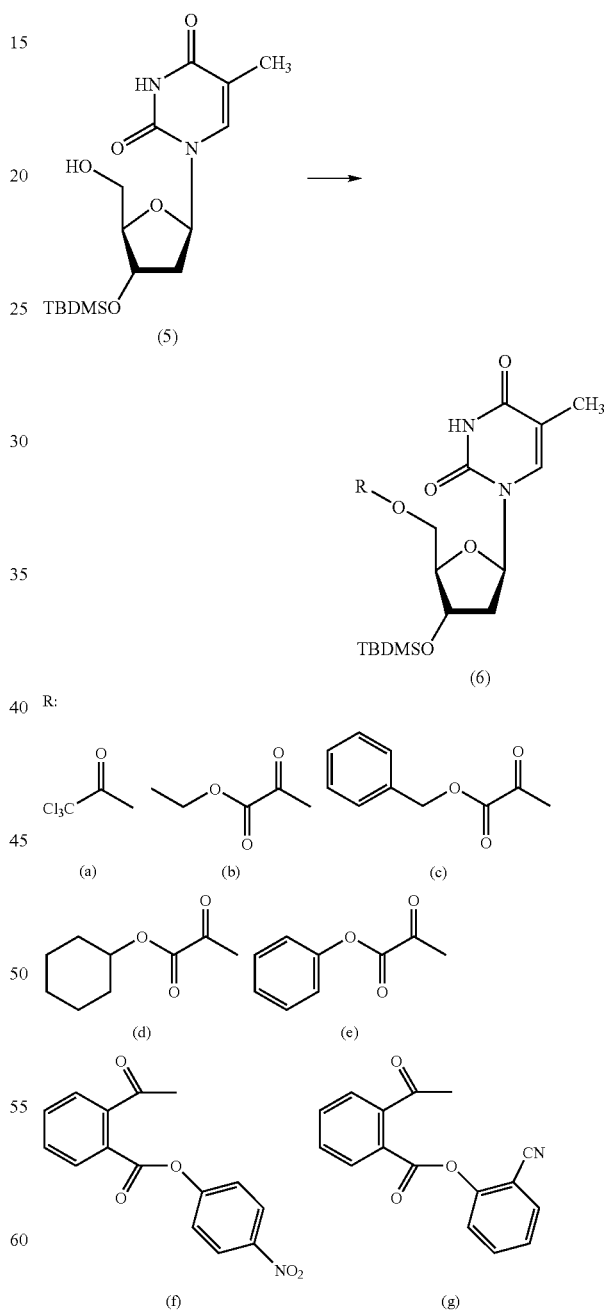

The cleavage of the 5'-acyl groups of the thymidine derivatives (6a-g) with certain primary amines including n-butylamine and 2-(N,N-diethylamino)ethylamine (DEAEA) as deprotection reagents is complete in less than 10 minutes in various solvents. In acetonitrile, the cleavage is complete within 4 minute for 10% solutions, v/v, of the above amines. The investigation of the cleavage reaction with and without additives is described in Example 2. The cleavage is generally faster in acetonitrile than in DMF, THF or dichloromethane. It is accelerated by the presence of small quantities of methanol (2.5-10%, v/v) in the deprotection reaction. The cleavage is also faster with higher concentrations of the respective amines (20% vs. 10%, v/v). In the case of the trichloroacetyl derivative (6a) a nucleosidic side product is formed during the cleavage with n-butylamine. The side product forms to a considerable extent (appr. 20%) when acetonitrile is used as the reaction solvent, but is not observed when dichloromethane is used as the reaction solvent. The side product is, once formed, stable towards the deprotection reagent. In the case of the oxalylester derivatives (6b-e) the respective oxalyl nucleoside monoester monoamide can be observed to some extent in the reaction mixture at the beginning of the cleavage reaction. The monoester monoamide is nevertheless rapidly converted to the final deprotection product (5). Quantitative conversion of (6) to (5) occurs for all oxalylester derivatives. The cleavage of the cyclohexyloxydicarbonyl derivative CyOx-dT-Si (6e) is complete in a 10% n-butylamine solution in acetonitrile, v/v, or in a 10% solution of the amine DEAEA in acetonitrile, v/v, in less than 1 minute at room temperature.

The 2-(4-nitrophenoxycarbonyl)-benzoyl group PSNp and the 2-(2-cyanophenoxycarbonyl)-benzoyl group PSCp of the 5'-acyl thymidine derivatives (6f) and (6g) are designed for a cleavage reaction which occurs with primary amines via to a two-step reaction mechanism. The principle of the cleavage reaction is illustrated in Scheme 2 wherein PSNp is used as an example. In a first reaction step the ortho-p-nitrophenolate ester moiety of the PSNp-group as in (6f) is rapidly converted to an ortho-alkylamido moiety as in (7). The resulting 2-alkylamidobenzoyl group is cleaved in a second reaction step via an intramolecular reaction to provide the respective phthalic acid imide as in (8) and the respective nucleoside with a free hydroxyl group, i.e. (5) in Scheme 2. Likely, the second step in the mechanism is accelerated compared to other reactions of amides with ester linkages due to the neighbor group effect of the ortho-alkylamido group. The putative mechanism is illustrated in Scheme 2.

Scheme 2

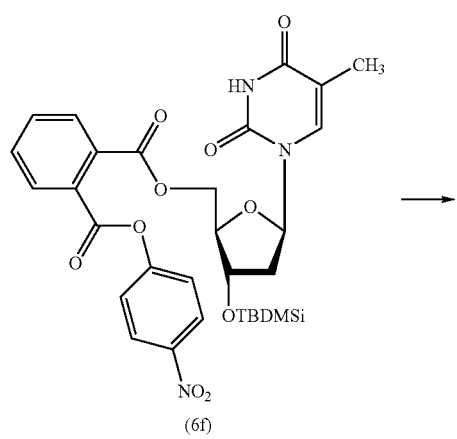

(6f)

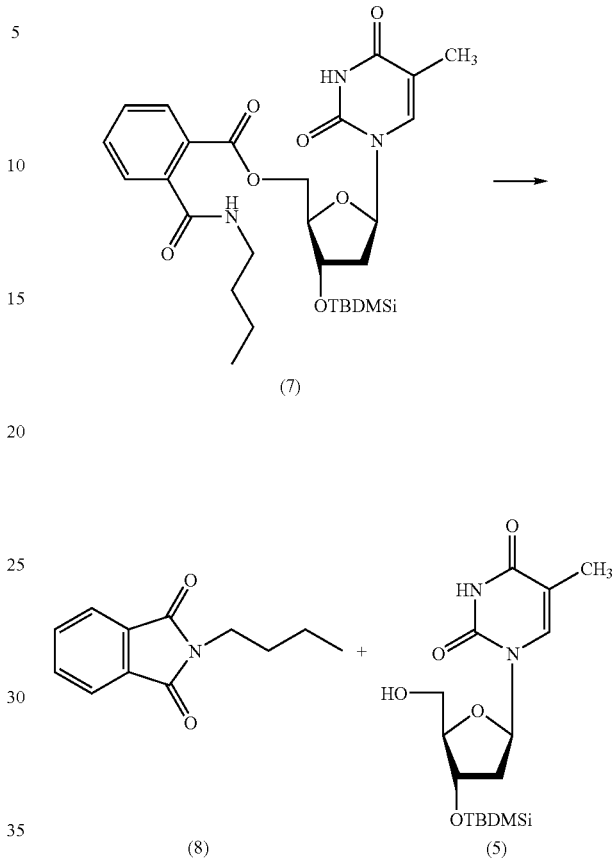

During cleavage of the PSNp-group with DEAEA another neighbor group effect is to be considered, which is illustrated for the cleavage of the PSNp-group in Scheme 3. In Scheme 3, the intermediate ortho-alkylamidobenzoyl derivative (9) carries an alkylamido group wherein the alkyl substituent is diethylaminoethyl, which contains a tertiary amino group. The tertiary amino group is in close proximity to the amide group and is likely participating in the intramolecular reaction resulting in the formation of the respective phthalic acid amide and is expected to further accelerate the cleavage of the PSNp-group. The cleavage of the PSNp group of (6f) is indeed much faster with DEAEA than with n-butylamine. Whereas the cleavage with 10% n-butylamine in acetonitrile, v/v, is appr. 25% complete in 30 seconds (75% intermediate (7) is formed in this time interval), the cleavage with 10% DEAEA in acetonitrile, v/v, is quantitative within this time interval. The mechanism illustrated in Schemes 2 and 3 for the PSNp group is not restricted to this particular group. A similar acceleration of the cleavage reaction was observed for other 2-phenoxycarbonylbenzoyl groups, in particular the 2-(2-cyanophenoxycarbonyl)-benzoyl group (PSCp-group) and the 2-(3,5-bis(trifluoromethyl)-phenoxy)-benzoyl group, when DEAEA was applied as cleaving agent compared to the cleavage reaction with monofunctional amines.

Scheme 3

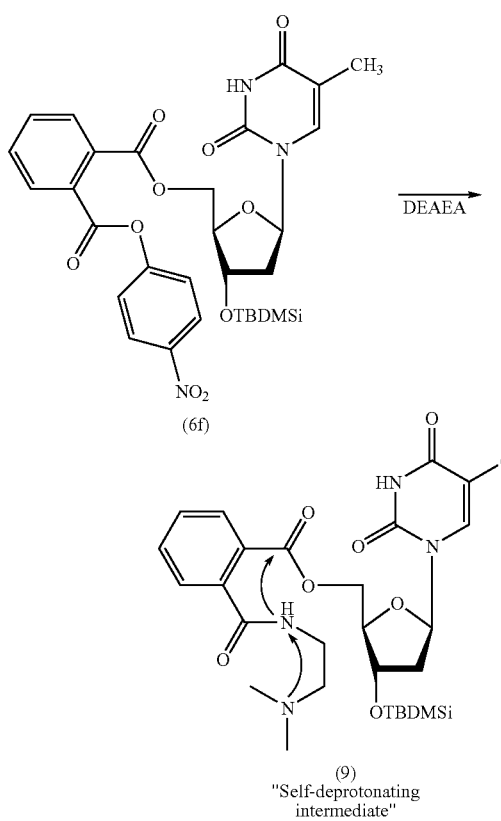

(6f)

(9) "Self-deprotonating intermediate"

Figure 1B:
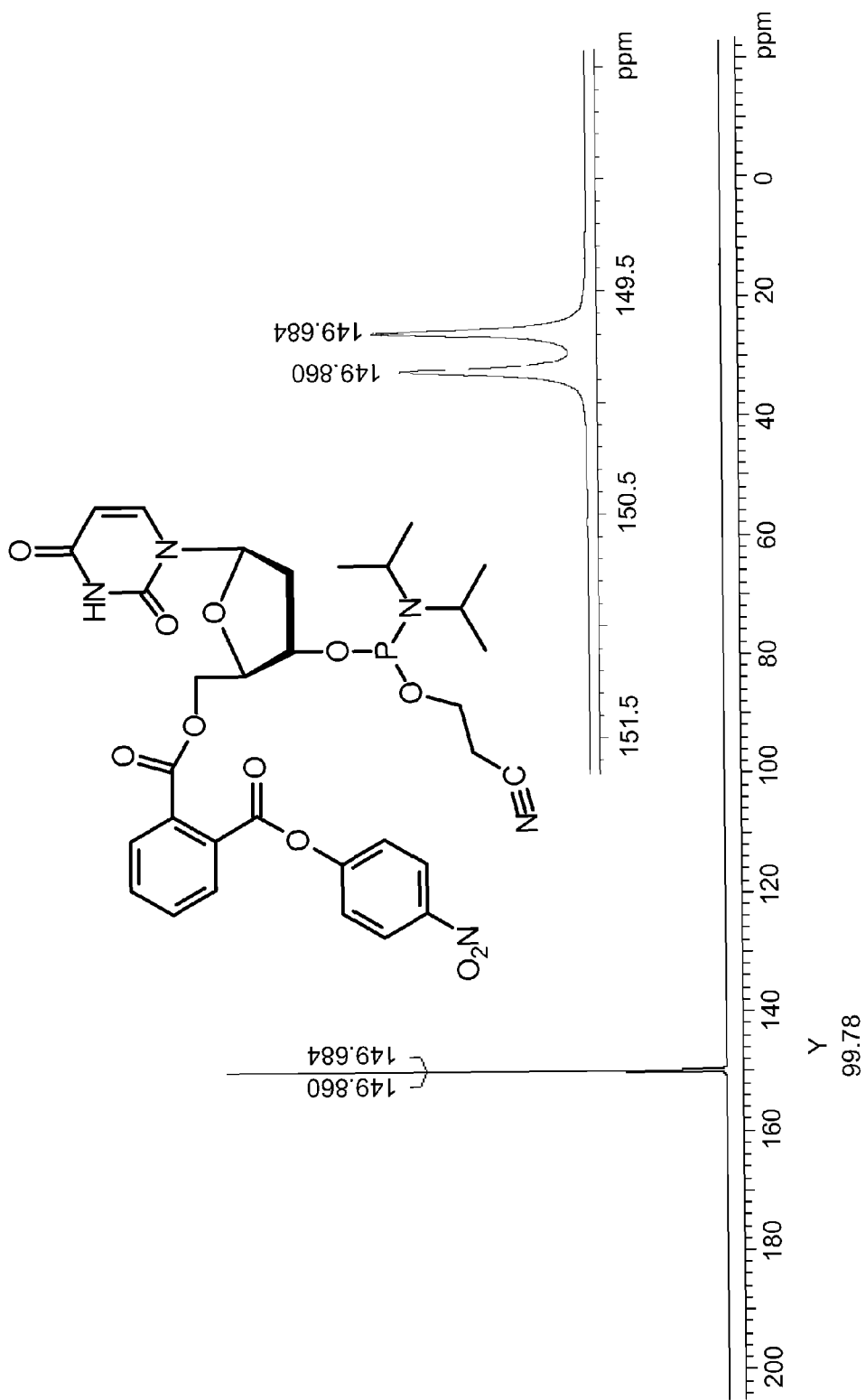

Phosphoramidites derived from nucleosides protected with 5'-acyl groups as in (6a-g) can be prepared through the removal of the 3'-TBDMS group with standard desilylation procedures and subsequent phosphoramidation as illustrated for the synthesis of phosphoramidites with β-cyanoethyl phosphate protective groups, CyOX-dT-amidite (10), PSNp-dT-amidite (11), and PSCp-dT-amidite (12) in Examples 3, 4 and 5. Phosphoramidites with alternative phosphate protective groups can also be prepared as illustrated in Example 6 for the synthesis of CyOX-dT-amidite (13) which carries an allyl phosphate protective group in its amidite moiety. The amidites (10), (11), (12) and (13) were obtained in high purity. The $^{31}$P-NMR spectra of (10) and (11) are provided in FIG. 1.

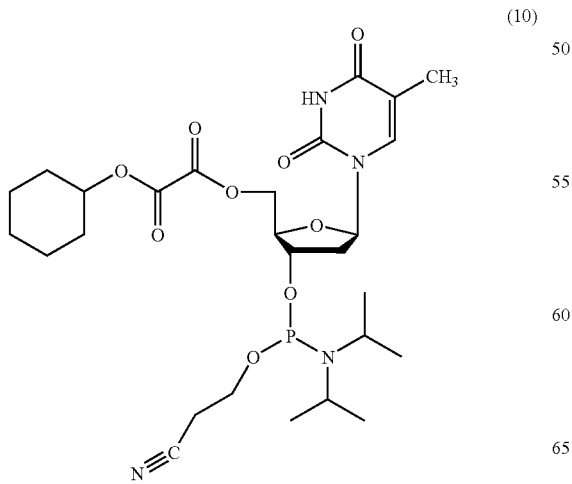

(10)

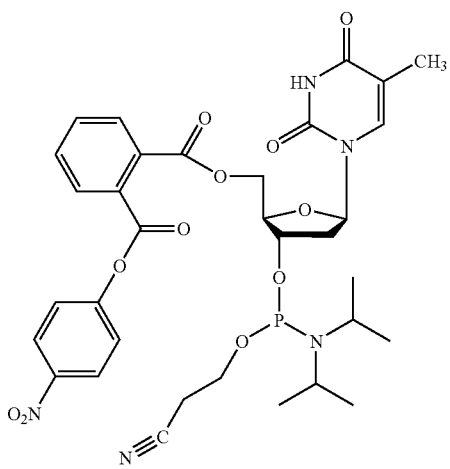

(11)

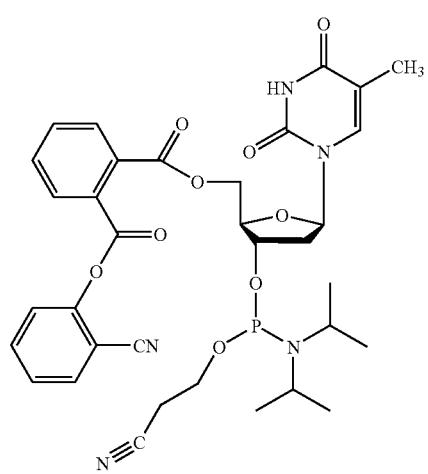

(12)

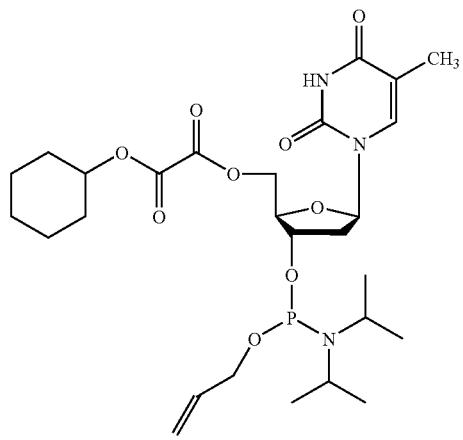

(13)

The present invention is not limited to phosphoramidites with β-cyanoethyl and allyl phosphate protective groups. Other phosphate protective groups for phosphoramidites known to those skilled in the art, e.g. methyl-, benzyl-, p-nitrophenyl-1-ethyl-, 4-methylthio-1-butyl-, 2-(N-acetyl) amino-1-ethyl or 2-naphthylcarbamoyloxy-1-ethyl are also within the scope of the invention.

The oxalyl ester acyl protective groups and the 2-phenoxycarbonylbenzoyl protective groups of the thymidine derivatives (6b-g) are stable against the reagents employed in the coupling and oxidation steps of synthesis cycles in the phosphoramidite mediated synthesis of oligonucleotides on solid supports as illustrated for CyOX-dT-Si (6d) and PSNp-dT-Si (6f) in Table 1. (6f) is susceptible to slow cleavage in Cap B solution (component B of the capping reagent commonly applied in oligonucleotide synthesis with 5'-DMT protected phosphoramidites, NMI/pyridine/THF 1/1/8, v/v) and decomposes completely within 22 hours in a capping reagent composed of Cap A and Cap B reagents 1/1, v/v (Cap A=component A of the capping reagent commonly applied in oligonucleotide synthesis with 5'-DMT protected phosphoramidites, acetic anhydride/THF 1/9, v/v). (6d) is somehow less susceptible to deterioration in the above capping reagents, but is also degraded in a mixture of Cap A and Cap B reagents 1/1, v/v (23% decomposition in 22 hours). Consequently, the standard capping reagents commonly employed in synthesis cycles with 5'-DMT protected phosphoramidites (1) are not suitable for synthesis cycles with 5'-acyl phosphoramidites carrying oxalylester protective groups or 2-phenoxycarbonylbenzoy protective groups with similar reactivity as the PSNp- or PSCp-groups.

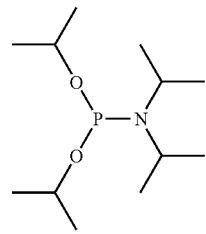

(14)

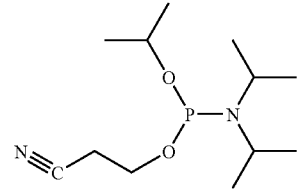

(15)

TABLE 1

|  | Purity | | | | |
| --- | --- | --- | --- | --- | --- |
|  | CyOX-dT-Si (6d) | | PSNp-dT-Si (6f) | | |
| Reagent | 6 hours | 22 hours | 6 hours | 22 hours | Result |
| 0.25M activator 42[1)] | 100.00 | 100.00 | 100.00 | 98.61 | (6d) and (6f) stable |
| 0.25M activator 42, DIPA[2)] | 95.70 | 100.00 | 98.96 | 98.50 | (6d) and (6f) stable |
| Cap A | 99.22 | 99.63 | 99.33 | 99.34 | (6d) and (6f) stable |
| Cap B | 98.47 | 98.44 | 94.37 | 86.48 | (6d) stable, (6f) slow decomposition |
| Cap A/Cap B 1/1, v/v | 86.48 | 76.66 | 30.63 | 4.79 | (6d) and (6f) decomposition |
| 0.02 M I$_2$ in THF/H$_2$O/pyridine | 99.00 | 98.08 | 99.66 | 99.64 | (6d) and (6f) stable |
|  | 100.00 | 100.00 | 100.00 | 99.83 | (6d) and (6f) stable |

[1)]Activator 42 = 5-(3,5-Bis(trifluoromethyl)phenyl)-1H-tetrazole
[2)]DIPA = Diisopropylamine Oxalylester acyl groups and the PSNp- and PSCp-group are nevertheless stable against phosphoramidite coupling conditions. Non-nucleosidic phosphoramidites such as bis(diisopropyloxy)diisopropylaminophosphane (14) or 2-cyanoethoxydiisopropylamino-isopropyloxyphosphane (15), or other non-nucleosidic phosphoramidites can therefore be applied as capping reagents in synthesis cycles with the respective 5'-acyl phosphoramidites. Capping reactions with non-nucleosidic phosphoramidites can be favorably performed directly after the coupling reaction of the nucleoside phosphoramidite. At this point of the chain elongation cycle the solid support is immersed in a solution containing an activator and the solution is completely dry due to the presence of excess nucleoside phosphoramidite from the preceding coupling reaction, which reacts with spurious water. The addition of a non-nucleosidic phosphoramidite such as (14) or (15) to this solution, with or without additional activator solution, results in very efficient capping in less than 1 minute reaction time. It is not necessary to apply a washing step between the coupling and the capping reaction in this case.

In one embodiment of the present invention an acid labile linker is applied for the attachment of the first nucleoside to the solid support. Preferably, the linkage is completely stable during the reaction steps of the synthesis cycles and completely cleaved under conditions employed to remove nucleobase protective groups and 2'-protective groups after the chain assembly on the solid support. The preparation of a suitable support with an acid labile linker (19) is illustrated in Scheme 4 and in Example 7. The commercially available monovinylether of 1,4-butanediol (16) is treated with p-nitrophenylchloroformate in pyridine to prepare the p-nitrophenylester (17). (17) is condensed with CyOX-dT in the presence of camphorsulfonic acid (CSA) to prepare the acetaldehyde acetal (18). (18) is attached to amino-functionalized CPG through the reaction of its active ester group, i.e. the p-nitrophenylester group, with the amino groups on the support. (19) comprises an acetacetal linker. Acetacetals are suitably acid labile for their application as protective groups in ribonucleosides as demonstrated by Matysiak et al. (1998) Helv. Chim. Acta 81:1545-1566 in the application of acetacetals as 2'-protective groups in ribonucleosides. The release of thymidine from the solid support (19) can be achieved with acidic buffers, e.g. citrate buffers of pH 2-3. Removal of the CyOX 5'-protective group from (19) through a brief treatment of the support with 20% n-butylamine in acetonitrile, v/v, followed by washing of the support with acetonitrile and incubation in citrate buffer pH3 results in the release of thymidine as the sole UV-active product. The release of thymidine is complete within 48 hours at 37° C. in the above buffer. Support (19) is completely stable to a solution of 0.25 M 4,5-dicyanoimidazole at room temperature. Released thymidine can not be detected after the incubation of the support in this activator solution for 24 hours at room temperature. Oligonucleotides are therefore not prematurely released from the support during the phosphoramidite coupling reactions in the synthesis cycles.

The synthesis of oligonucleotides with 5'-acyl phosphoramidites can also be performed on supports with linkers that are cleaved under neither acidic nor basic conditions, for instance supports with linkers that are cleaved with fluoride salts such as tetrabutylammoniumfluoride (TBAF), e.g. a 1 M solution of TBAF in THF, or with pyridinium hydrofluoride complex or triethylamine hydrofluoride complex. For example, the synthesis can be performed with support (20), which comprises a disiloxide linker. The synthesis of the respective oligonucleotide on support (20) is conducted in the same manner as with support (19) after a brief treatment with 3% trichloroacetic acid in dichloromethane to remove the 5'-DMT group from the support. The synthesis product is cleaved from the support after the chain assembly with e.g.

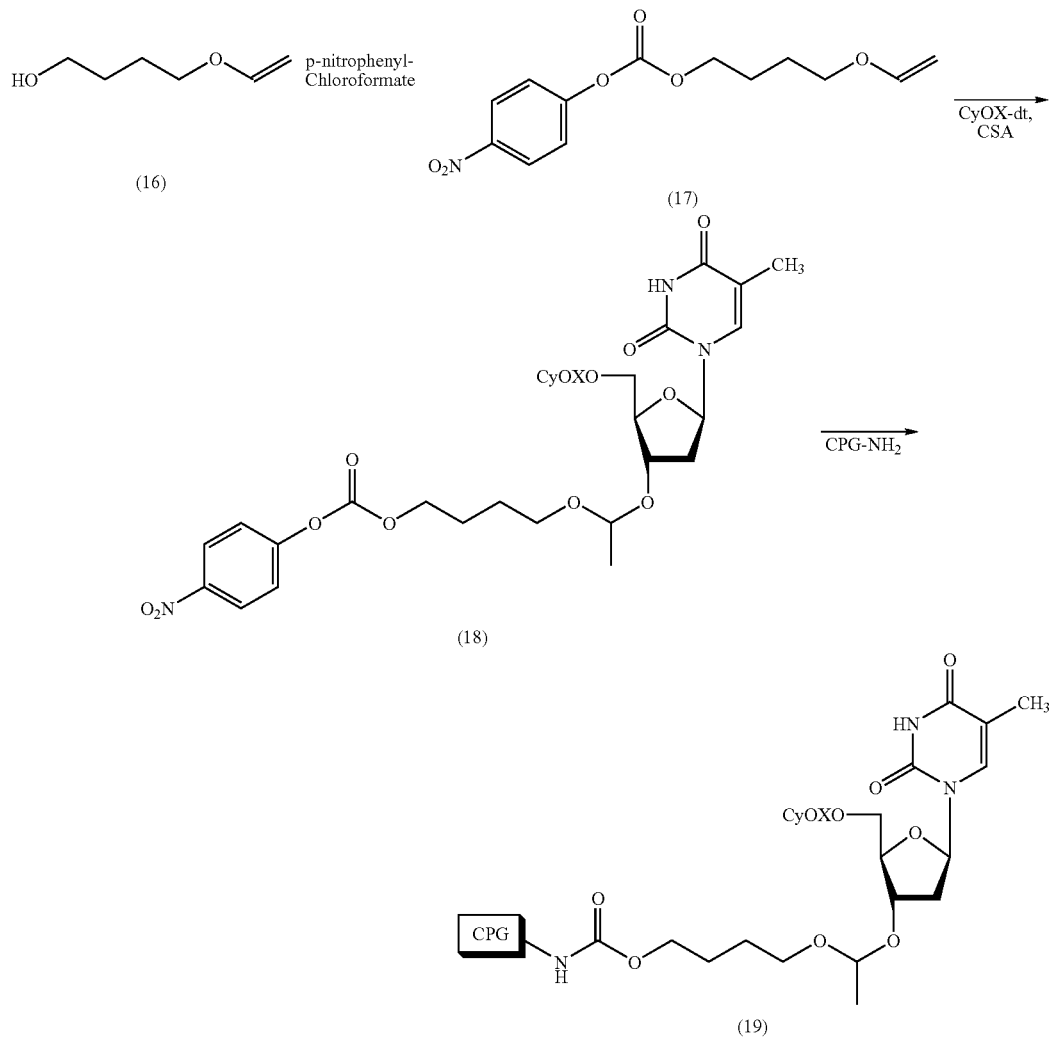

Figure 2A:
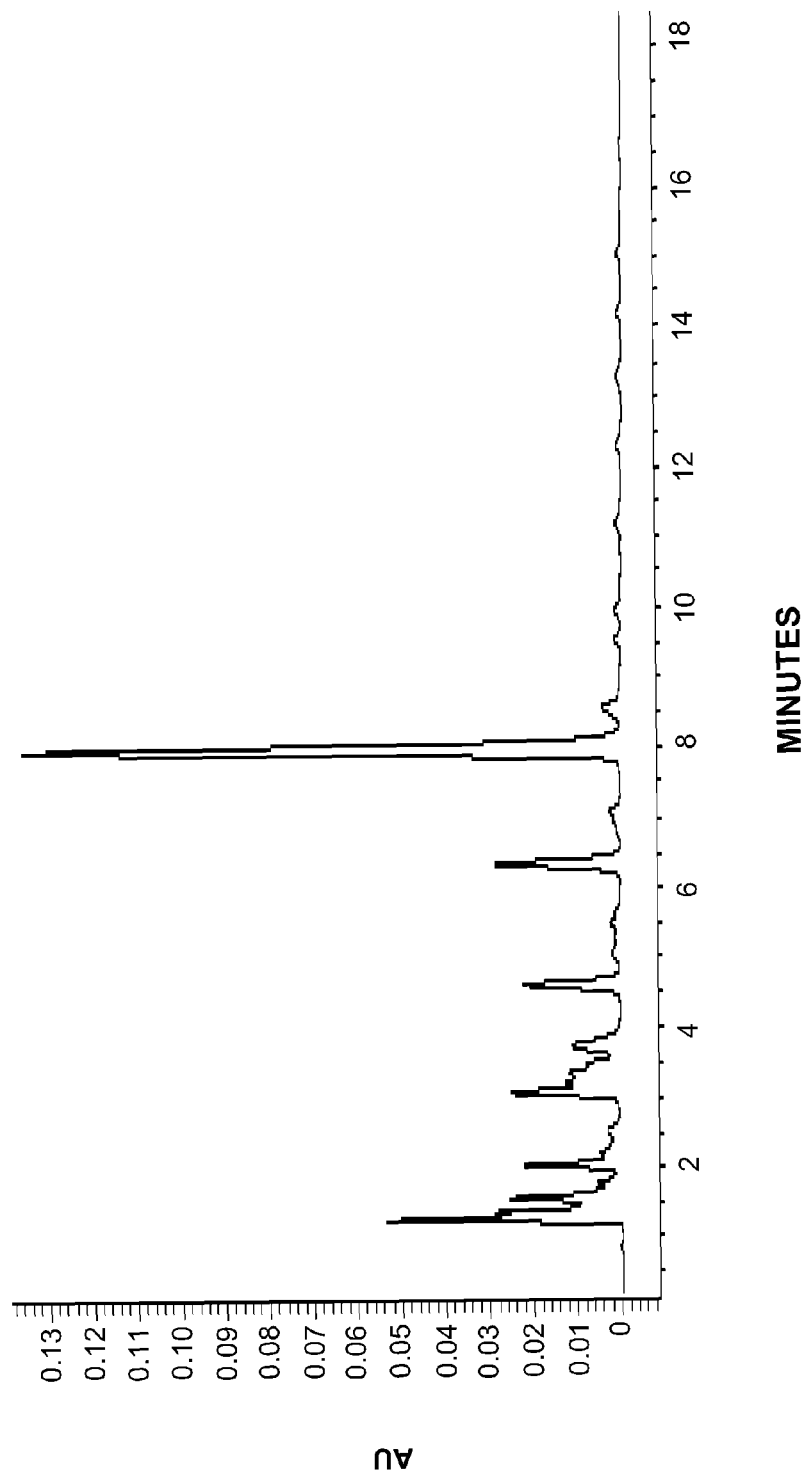
FIG. 2 displays anion-exchange HPLC chromatograms of the oligonucleotide $dT_{10}$, prepared through solid phase synthesis on a support with an acid labile linker (19). Panel A displays the olidonucleotide prepared with CyOX-dT-β-cyanoethyl-amidite (10). Panel B displays the olidonucleotide prepared with PSCp-dT-β-cyanoethyl-amidite (12).
Figure 2B:
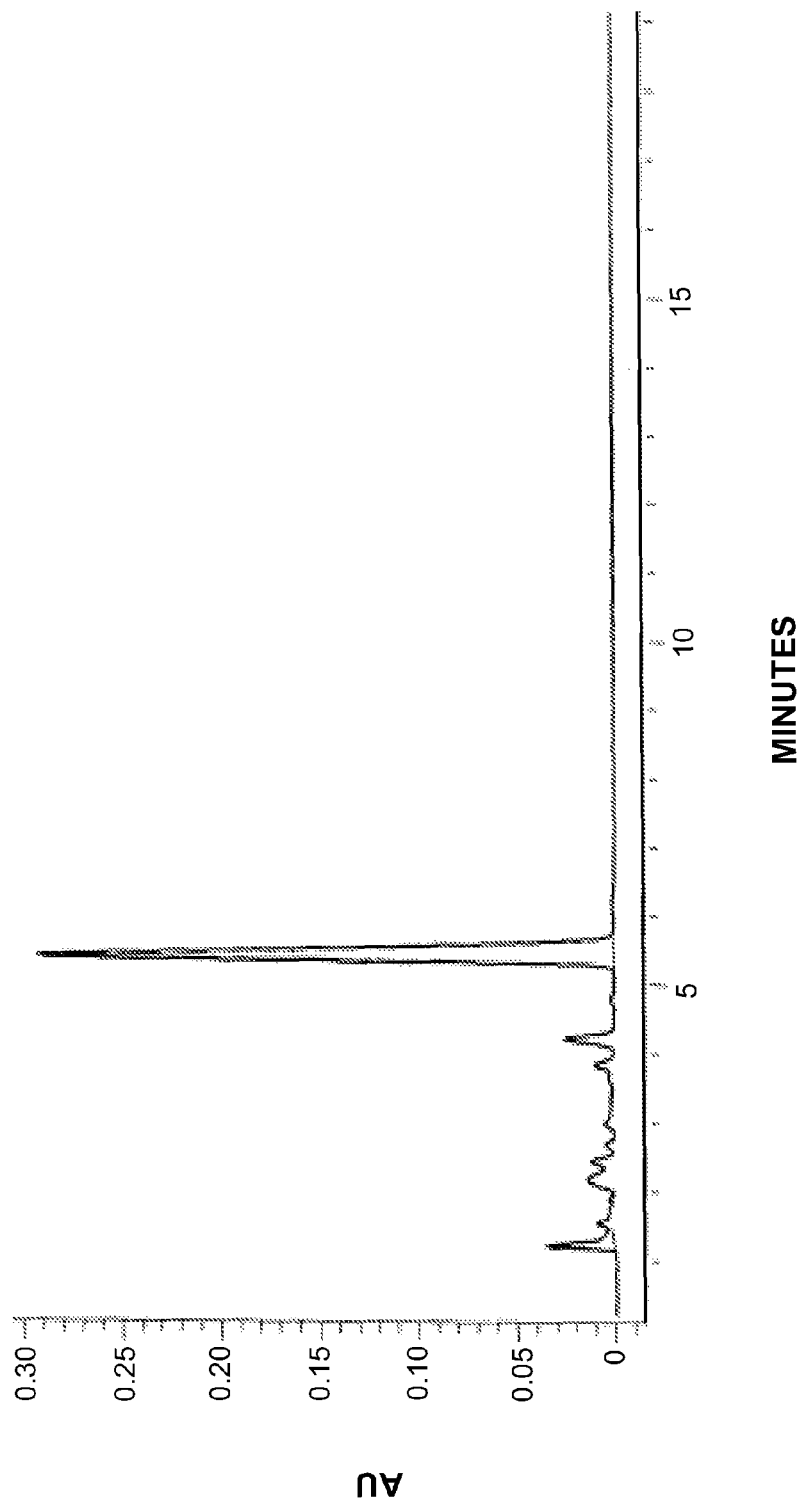
Figure 3A:
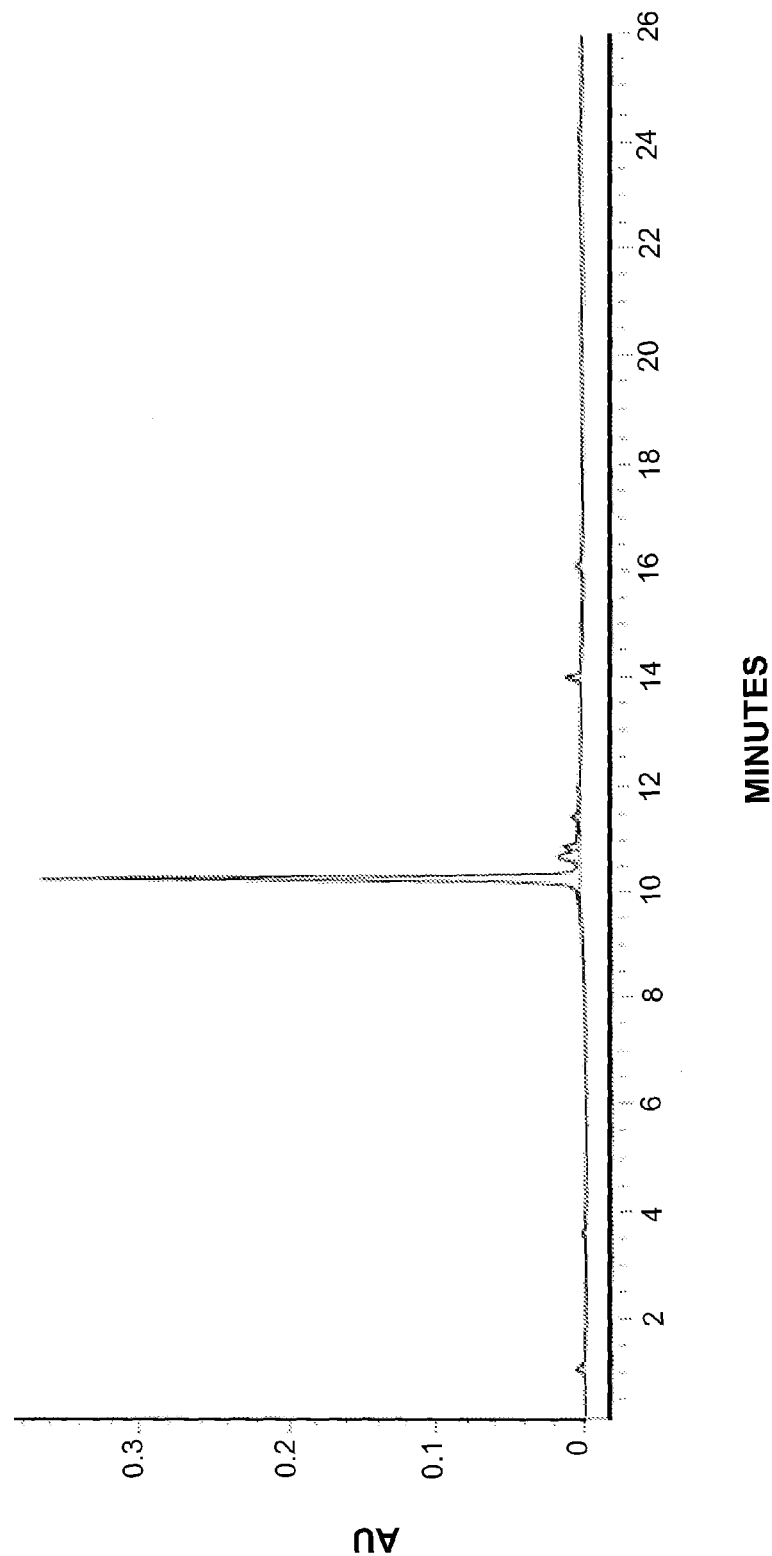
FIG. 3 displays the reversed phase HPLC chromatograms of the oligonucleotide $dT_{10}$, prepared through solid phase synthesis on a support with an acid labile linker (19). Panel A displays the olidonucleotide prepared with PSCp-dT-β-cyanoethyl-amidite (12). Panel B displays the olidonucleotide prepared with CyOX-dT-allyl-amidite (13).
Figure 3B:
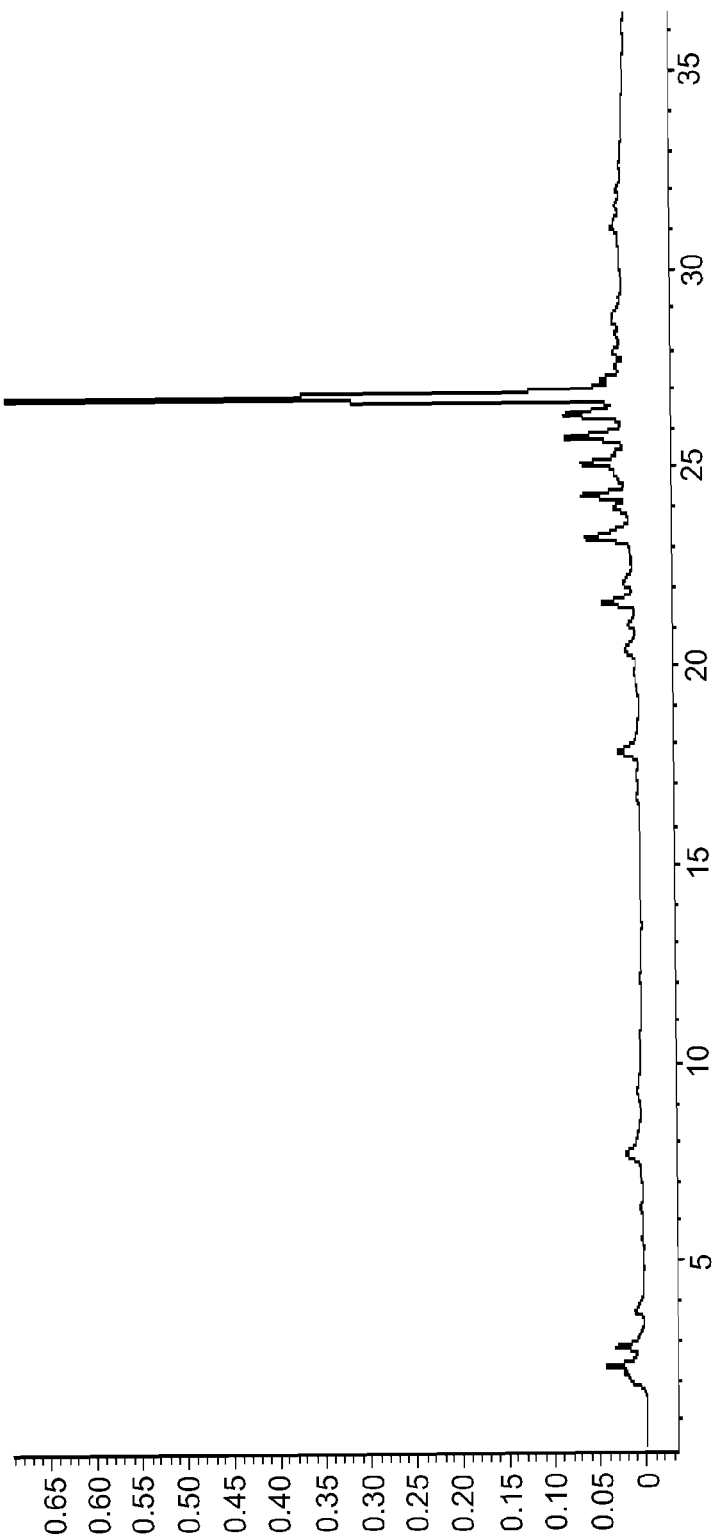

The synthesis of oligonucleotides with 5'-acyl phosphoramidites on support (19) is illustrated in Examples 8 and 9. CyOX-dT-amidite (10) and PSCp-dT-amidite (12) are applied as a 50 mg/ml solution in acetonitrile to prepare the oligonucleotides $dT_{10}$ and $dT_{20}$. The capping step is performed with the non-nucleosidic phosphoramidite (14) as the capping reagent. The oligonucleotide products were obtained in good yield and purity as demonstrated by the anion-exchange and reverse-phase HPLC chromatogram of the oligonucleotide $dT_{10}$ in FIGS. 2 and 3.

triethylamine hydrofluoride complex. The application of support (20) in the synthesis of oligonucleotides with 5'-acyl phosphoramidites is illustrated in Example 10 for the synthesis of poly-dT sequences with CyOX-dT-β-cyanoethyl amidite (10) and in Example 11 for the synthesis of poly-dT sequences with PSNp-dT-β-cyanoethyl amidite (11). In addition to support (20) any support with linkers that are cleaved under neither acidic nor basic conditions can be employed to practice the methods of the present invention.

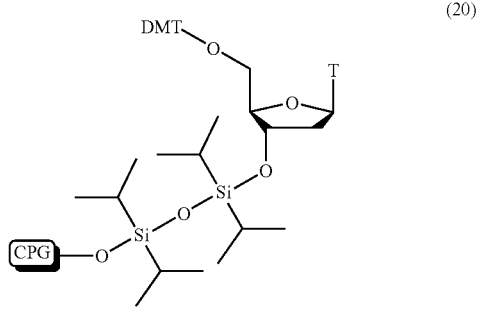

(20)

The synthesis of oligonucleotides with 5'-acyl phosphoramidites can also be performed on supports with linkers that are stable to the basic reagents applied in the front end deprotection step, but that are cleaved under more drastic basic conditions, for instance on solid supports which require extensive treatments with bases at elevated temperatures to cleave the linker to the first nucleoside. If, e.g. the front end deprotection step of the synthesis cycles is performed with solutions of n-butylamine or DEAEA in acetonitrile at room temperature within one minute and the cleavage of the linker is performed in several hours at temperatures above 70° C., then the linkage to such supports remains largely intact during the chain assembly and very little, if any, of the support bound oligonucleotide is cleaved in the deprotection step of the synthesis cycles. An example for a support that requires rather drastic basic conditions to cleave the linkage to the first nucleoside is the commercially available universal support (21). The linker in (21) is cleaved with conc. aqueous ammonia in the presence of lithium chloride at 75° C. for 6 hours and is largely stable to solutions of n-butylamine or DEAEA in acetonitrile at room temperature. The application of support (21) in the synthesis of oligonucleotides with 5'-acyl phosphoramidites is illustrated in Example 12 for the synthesis of poly-dt sequences with CyOX-dT-β-cyanoethyl amidite (10). In addition to support (21) any support with linkers that are cleaved with bases at elevated temperatures with long cleavage times can be employed to practice the methods of the present invention.

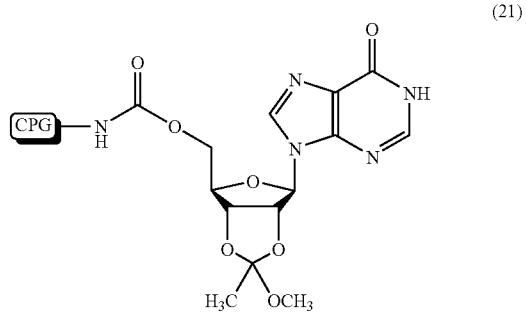

(21)

Another example for the application of support (21) in the synthesis of oligonucleotides with 5'-acyl phosphoramidites is the use of CyOX-dT-allyl phosphoramidite (13) in the synthesis of poly-dt sequences. Respective oligonucleotide syntheses are illustrated in Example 13. The RP-HPLC chromatogram of dT$_{10}$ prepared with amidite (13) is depicted in FIG. 4. The allyl phosphate protective group is not fully compatible with the standard iodine based oxidizing reagent as described by Manoharan et al. (2000) Org. Lett. 2:243-246.

The alternative reagent 0.02 M butanone peroxide in dichloromethane as described by Kataoka et al. (2001) Org. Lett. 3:815-818 is therefore applied in the chain assembly with amidite (13). The allyl phosphate protective group is cleaved with aqueous ammonia or methylamine, see Bergmann et al. (1995) Tetrahedron 25:6971-6976. The removal of the phosphate protective group after the chain assembly with the synthesizer is therefore performed simultaneously with the cleavage of the linker of support (21) with methylamine solution at 75° C. for 6 hours.

n-Butylamine and 2-(N,N-diethylamino)ethylamine are applied as organic bases in the presented examples. The present invention is, however, not limited to these amines as front end deprotection reagents. Other primary amines can be applied with equal success. For instance, the CyOX-group of CyOX-dT (6d) is cleaved in less than 1 minute at room temperature with 10% solutions of 2-methoxyethylamine or isobutylamine in acetonitrile, v/v. Other suitable amines include, but are not limited to n-propylamine, n-pentylamine, n-hexylamine, cyclohexylamine and the like. The cleavage can also be accomplished with mixtures of primary amines. The cleavage of 5'-acyl groups of the present invention is nevertheless not limited to primary amines as cleavage reagents, but can also be performed with secondary amines as cleavage reagents. For instance, the CyOX protective group of CyOX-dT-Si (6d) can be completely cleaved with a solution of the secondary amine N,N'-dimethylethylenediamine (10% in acetonitrile, v/v) within less than 60 seconds at room temperature. Noteworthy, in related series of primary and secondary amines R—NH$_2$ and R$_2$—NH wherein R represents the same alkyl or substituted alkyl group, the cleavage of 5'-acyl groups occurs generally much faster with primary amines than with secondary amines. If, for instance, CyOX-dT-Si (6d) is incubated in solutions of 2-methoxyethylamine or bis(2-methoxyethyl)-amine (10% in acetonitrile, v/v), then the cleavage of the CyOX protective group is complete in less than 60 seconds in case of the solution of the primary amine 2-methoxyethylamine, but is incomplete even after 24 hours incubation time in case of the secondary amine bis(2-methoxyethyl)amine.

In a preferred embodiment of the present invention 2'-protective groups of 5'-acyl ribonucleoside phosphoramidites are protected with acid labile groups. Even more preferred, the respective phosphoramidites are used to synthesize oligonucleotides on solid supports with an acid labile linker and the 2'-protective groups are removed after the chain assembly under conditions which are applied to cleave the acid labile linker. In this method the cleavage of the linker and the removal of the 2'-protective groups are performed simultaneously. For example, 5'-CyOX-2'-(4-methoxytetrahydropyranyl)-uridine phosphoramidite CyOX-rU$_{MTHP}$-β-cyanoethyl amidite (22) can be applied to prepare polyuridine sequences on the solid support (19). After the chain assembly with a synthesizer the respective oligonucleotides are cleaved from the support in, e.g. dilute hydrochloric acid (pH 2) at room temperature or in aqueous buffers of pH 3 at elevated temperature, for instance at 37° C., with concomitant cleavage of the 4-methoxytetrahydro-pyranyl 2'-protective groups.

Noteworthy, the tert.-butyldimethylsilyl group (TBDMS group), which is widely applied as the 2'-protective group in commercially available RNA phosphoramidites, can also be viewed as an acid labile 2'-protective group, because it can be removed from the 2'-position of ribooligonucleotides with diluted aqueous solutions of formic acid or acetic acid, or with a 0.01 M HCl/dioxane mixture, 1/1, v/v, as demonstrated by Kawahara et. al. (1996) J. Am. Chem. Soc. 118:9461-9468. The application of a combination of 5'-acyl- and 2'-TB- DMS protective groups in ribonucleoside phosphoramidites for the synthesis of oligonucleotides is therefore within the scope of the present invention. For example, 5'-CyOX-2'-tert.-butyldimethylsilyl-uridine phosphoramidite CyOX-rU$_T$-$_{BDMS}$-β-cyanoethyl amidite (23) can be applied to prepare polyuridine sequences in the same manner as the 2'-MTHP protected uridine phosphoramidite (22).

the removal of the nucleobase protective groups are performed simultaneously. For example, 5'-CyOX—N6-monomethoxytrityl-deoxyadenosine phosphoramidite CyOX-dA(mmt)-β-cyanoethyl amidite (24) or 5'-PSCP-N6-monomethoxytrityl-deoxyadenosine phosphoramidite PSCP-dA(mmt)-β-cyanoethyl amidite (25) can be applied to prepare polydeoxyadenosine sequences on the solid support (19). After the chain assembly with a synthesizer the respective oligonucleotides are cleaved from the support in, e.g. dilute hydrochloric acid (pH 2) at room temperature or in aqueous buffers of pH 3 at elevated temperature, for instance at 37° C., with concomitant cleavage of the monomethoxytrityl nucleobase protective groups.

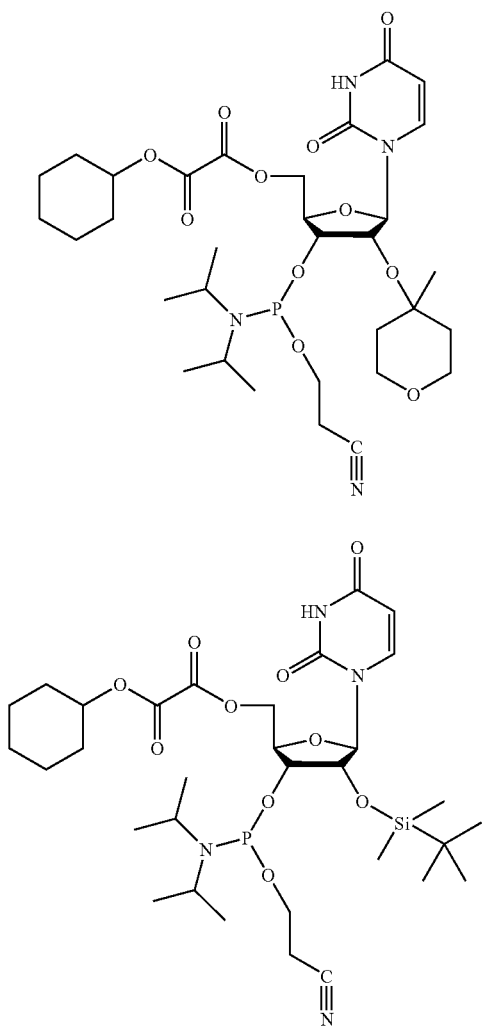

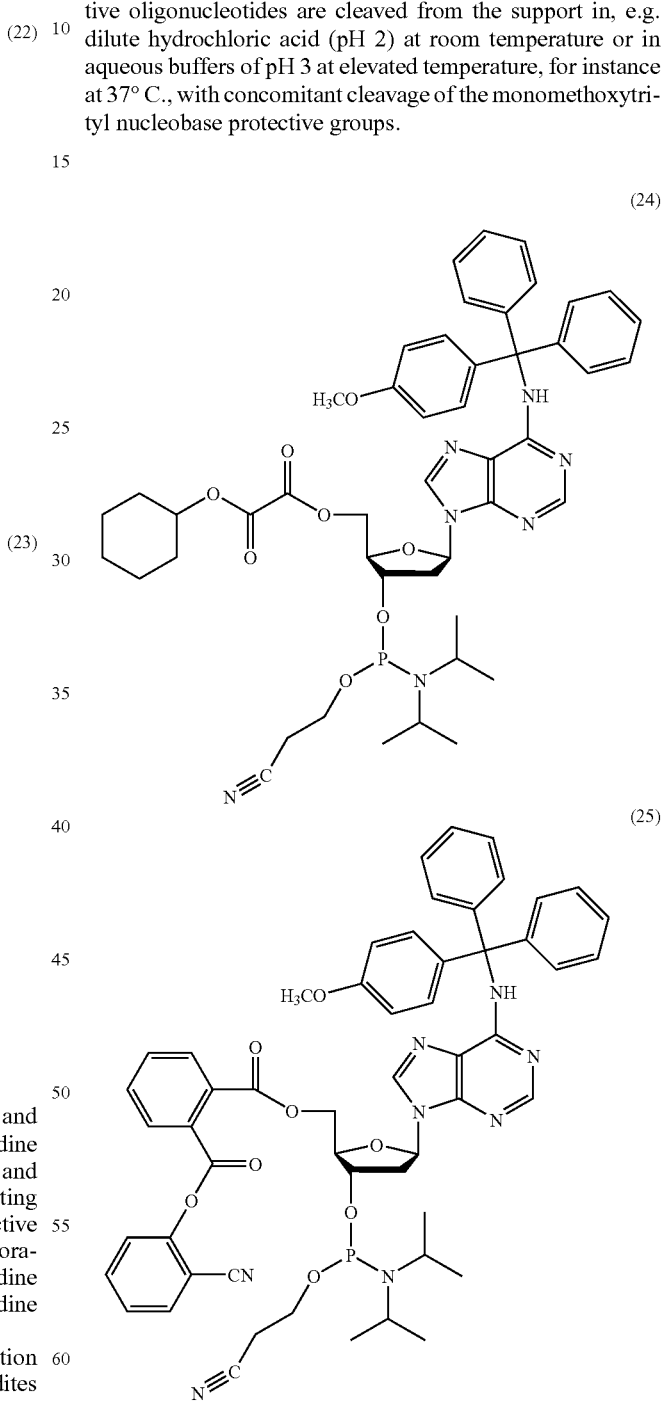

The synthesis of the uridine phosphoramidites (22) and (23) is illustrated in Example 14. The 2'-protected uridine nucleosides 2'-(4-methoxytetrahydropyranyl)-uridine and 2'-tert.-butyldimethylsilyluridine are employed as starting materials. The CyOX-group is introduced via regioselective 5'-acylation followed by the introduction of the 3'-phosphoramidite group in this example. The application of the uridine phosphoramidite (23) in the synthesis of a polyuridine sequence is illustrated in Example 15.

In another preferred embodiment of the present invention the nucleobase protective groups of 5'-acyl phosphoramidites are labile to acidic reagents. Even more preferred, the respective phosphoramidites are used to synthesize oligonucleotides on solid supports with an acid labile linker and the nucleobase protective groups are removed after the chain assembly under conditions which are applied to cleave the acid labile linker. In this method the cleavage of the linker and The synthesis of the deoxyadenine phosphoramidites (24) and (25) is illustrated in Examples 16 and 17. Phosphoramidite (24) is prepared from deoxyadenine in a 3-step reaction sequence involving the monomethoxytritylation of the base moiety via transient protection of the 5'- and 3'-hydroxy groups with trimethylsilyl groups, the regioselective introduction of the CyOX-group on the 5'-position and the introduction of the 3'-phosphoramidite group. Phosphoramidite (25) is prepared employing the protected nucleoside O3'-tert.-Butyldimethylsilyl-N6-(4-tert.-butylphenoxy)acetyl-O5'-dimethoxytrityldeoxyadenosine, DMT-dA(tac)-Si as starting material. The synthesis involves the removal of the 4-tert.-butylphenoxyacetyl base protective group with DEAEA as deacylating reagent, the removal of the 5'-dimethoxytrityl group with trichloroacetic acid, the monomethoxytritylation of the base moiety via transient protection of the 5'-hydroxy group with a trimethylsilyl group, the introduction of a 2-carboxybenzoyl (phthaloyl) group at the 5'-position with phthalic acid anhydride in the presence of DMAP, the removal of the 3'-tert.-butyldimethylsilyl group with pyridine-HF complex, the conversion of the 5'-(2-carboxybenzoyl) group to a 5'-(2-(2-cyanophenoxy-carbonyl)benzoyl) (PSCP) group with 2-cyanophenyltrifluoroacetate, and the introduction of the 3'-phosphoramidite group. The application of amidite (24) in the synthesis of oligonucleotides is illustrated in Example 18.

Another example of a 5'-acyl phosphoramidite with acid labile base protection is the deoxycytidine amidite PSCP-dC(mmt)-amidite (26). The synthesis of phosphoramidite (26) is illustrated in Example 19. Deoxycytidine is applied as starting material. The synthesis involves the bis-silylation of the 5'- and 3'-hydroxy groups with tert.-butyldimethylsilylchloride and imidazole, the selective removal of the 5'-silyl group with aqueous trifluoroacetic acid, the monomethoxytritylation of the base moiety via transient protection of the 5'-hydroxy group with a trimethylsilyl group, the introduction of a 2-carboxybenzoyl(phthaloyl) group at the 5'-position with phthalic acid anhydride in the presence of DMAP, the removal of the 3'-tert.-butyldimethylsilyl group with pyridine-HF complex, the conversion of the 5'-(2-carboxybenzoyl) group to a 5'-(2-(2-cyanophenoxycarbonyl)benzoyl) (PSCP) group with 2-cyanophenyl-trifluoroacetate, and the introduction of the 3'-phosphoramidite group.

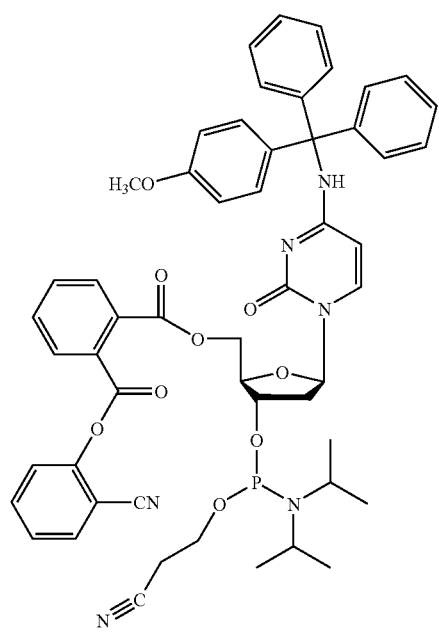

(26)

In a particularly preferred embodiment of the present invention all of the nucleobase protective groups and the 2'-protective groups are labile to acidic reagents and the respective phosphoramidites are used to synthesize oligonucleotides on solid supports with an acid labile linker. Even more preferred, the nucleobase protective groups and the 2'-protective groups are removed after the chain assembly under conditions which are applied to cleave the acid labile linker. Removal of all protective groups and cleavage of the linker occur simultaneously in this method. For instance, a polyriboadenosine sequence can be prepared by employing a 5'-CyOX—N6-monomethoxytrityl-O2'-(4-methoxytetrahydropyranyl)-protected β-cyanoethyl adenosine phosphoramidite, or any RNA sequence can be prepared when a set of suitably protected RNA phosphoramidites, e.g. a set of RNA phosphoramidites consisting of amidites with 5'-PSCP-protection, with 2'-MTHP-protection or 2'-TBDMS-protection, and with acid labile base protection is used in the respective oligoribonucleotide synthesis. After the chain assembly with a synthesizer the respective oligonucleotides are cleaved from the support in, e.g. dilute hydrochloric acid (pH 2) at room temperature or in aqueous buffers of pH 3 at elevated temperature, for instance at 37° C., with concomitant cleavage of the monomethoxytrityl nucleobase protective groups or other acid labile base protective groups, and the 4-methoxytetrahydropyranyl or tert.-butyldimethylsilyl 2'-protective groups. This embodiment of the invention is not limited to monomethoxytrityl nucleobase protective groups and 4-methoxytetrahydropyranyl or tert.-butyldimethylsilyl 2'-protective groups, but can be applied to other acid labile nucleobase protective groups and other acid labile 2'-protective groups known to those skilled in the art and to all combinations thereof.

In this embodiment, guanine nucleobases do not need to be protected or can be protected with protective groups, which are completely or partially removed during the chain assembly process, because unprotected guanine bases are compatible with phosphoramidite mediated oligonucleotide synthesis. In case of partial removal of guanine base protective groups during the chain assembly the cleavage of such groups can be completed after the chain assembly through a treatment with bases such as aqueous ammonia or methylamine solutions as it is performed in the conventional phosphoramidite oligonucleotide synthesis. An example of a 5'-acyl guanine phosphoramidite within the scope of the present invention is PSCP-dG(tac)-amidite (27). The synthesis of phosphoramidite (27) is illustrated in Example 20. N2-(4-tert.-butyl-phenoxy)acetyldesoxyguanosine, dG(tac) is applied as starting material. The synthesis involves the bis-silylation of the 5'- and 3'-hydroxy groups with tert.-butyldimethylsilylchloride and imidazole, the selective removal of the 5'-silyl group with aqueous trichloroacetic acid, the monomethoxytritylation of the base moiety via transient protection of the 5'-hydroxy group with a trimethylsilyl group, the introduction of a 2-carboxybenzoyl(phthaloyl) group at the 5'-position with phthalic acid anhydride in the presence of DMAP, the conversion of the 5'-(2-carboxybenzoyl) group to a 5'-(2-(2-cyanophenoxycarbonyl)benzoyl) (PSCP) group with 2-cyanophenyl-trifluoroacetate, the removal of the 3'-tert.-butyldimethylsilyl group with pyridine-HF complex, and the introduction of the 3'-phosphoramidite group.

The application of the 5'-PSCP-protected DNA phosphoramidites PSCP-dT-amidite (12), PSCP-dA(mmt)-amidite (25), PSCP-dC(mmt)-amidite (26) and PSCP-dG(tac)-amidite (27) in the preparation of a DNA heterosequence oligonucleotide is illustrated in Example 21.

The present invention can also be applied for the synthesis of deoxyribooligo-nucleotides or ribooligonucleotides with modifications in their nucleoside sugar or phosphate groups. For instance, 2'-O-alkyl modified, e.g. 2'-O-methyl modified oligonucleotides, or 2'-fluoro modified oligonucleotides can be prepared through the use of respective 2'-O alkyl or 2'-deoxy-2'-fluoro phosphoramidites with 5'-acyl groups, and phosphorothioate deoxyribonucleosides can be prepared through the use of a thioating reagent in the phosphite oxidation step of the synthesis cycles with 5'-acyl phosphoramidites. The invention is, however, not limited to the above modifications, but can be applied to the preparation of other oligonucleotides modified in their sugar or phosphate groups known to those skilled in the art and reviewed by Micklefield (2001) Current Medicinal Chemistry 8:1157-1179.

In conclusion, the application of 5'-acyl phosphoramidites (2) and (3) in the solid phase synthesis of oligonucleotides with phosphoramidites represents a versatile method for the synthesis of oligonucleotides which overcomes several limitations of the prior art. The cleavage of the front end protective group is irreversible and fast in this method and the by-products, which are primary amides or esters, are unreactive to the oligonucleotide product. Furthermore, the deprotection reagents for the cleavage of the acyl groups are easy to prepare and inexpensive. The application of large volumes of the front end deprotection reagents as in the conventional synthesis with 5'-DMT protected phosphoramidites is not required, which reduces the cost of the synthesis and also reduces the generation of hazardous chemical waste. The methods of the invention improve the quality of the prepared oligonucleotides due to irreversibility of the front end deprotection step in the synthesis cycles, which reduces the formation of deletion sequence side products, due to the avoidance of repeated exposure of the growing oligonucleotide chain on the support to strong acids, which prevents the formation of depurination side products during chain assembly, and due to the avoidance of premature loss of front end protective groups during coupling reactions, which prevents the formation of insertion sequence side products.

EXAMPLES

General Procedures

Analytical HPLC Methods for Synthetic Oligonucleotides

Method A (anion exchange): Dionex DNAPac PA100 column (4×250 mm), eluted with a linear gradient from 20% B to 80% B in 30 min. followed by a linear gradient from 80% B to 100% B in 3 min. with a flow rate of 1.0 ml/min., detection at $\lambda$=260 nm, buffer A 25 mM Tris base/1 mM EDTA, pH 8, buffer B 25 mM Tris base/1 mM EDTA/1 M NaCl, pH 8. Method B (reversed phase): Waters XTerra MS C18 column (2.5 µm, 4.6×50 mm), eluted with a linear gradient from 0% to 67% B in 40 min. with a flow rate of 0.5 ml/min., detection at $\lambda$=260 nm, buffer A 100 mM triethylammonium acetate (TEAA), pH 7 containing 5% acetonitrile, buffer B 100 mM triethylammonium acetate (TEAA), pH 7 containing 30% acetonitrile.

Example 1

Synthesis of 5'-acyl-3'-tert.-butyidimethylsilylthymidines (6a-f)

Synthesis of O3'-tert.-butyidimethylsilyl-O5'-trichloroacetylthymidine, TCA-dT-Si (6a)

O3'-tert.-Butyldimethylsilylthymidine (5) (6 g, 1.0 equiv.) was dissolved in pyridine (50 ml). Trichloroacetyl chloride (1.1 equiv.) was added with cooling (ice bath) and the reaction was continued at ambient temperature for 1 hour. The mixture was concentrated to a syrupy residue by evaporation. The residue was dissolved in dichloromethane (100 ml) and the resulting solution was extracted with water (3 times 100 ml). The organic phase was dried over sodium sulfate and evaporated to a foam. Purification by column chromatography on silica gel gave pure (98.9%) TCA-dT-Si (6a) (5.6 g, 66% yield).

Synthesis of O3'-tert.-butyidimethylsilyl-O5'-ethoxydicarbonylthymidine, EtOX-dT-Si (6b)

O3'-tert.-Butyldimethylsilylthymidine (5) (20 g, 1.0 equiv.) was dissolved in pyridine (100 ml). Commercially available oxalic acid ethyl ester chloride (1.1 equiv.) was added with cooling (ice bath) and the reaction was continued at ambient temperature for 1 hour. Ethanol (4 ml) was added and the reaction mixture was evaporated to a syrupy residue. The residue was dissolved in dichloromethane (150 ml) and the resultant solution was extracted with 5% sodium hydrogencarbonate solution (3 times 150 ml). The organic phase was dried over sodium sulfate and evaporated to a foam. The foam was coevaporated with THF and dissolved in dichloromethane (65 ml). The solution was added to a mixture of hexanes (750 ml) and diethylether (85 ml) with stirring at ambient temperature. The resulting precipitate was collected by filtration. Yield of pure (99.8%) EtOX-dT-Si (6b) (22 g, 86% yield).

Synthesis of Oxalic Acid Benzyl Ester Chloride

Oxalyl chloride (17.8 g, 5 equiv.) was dissolved in dichloromethane (25 ml). Benzyl alcohol (3.0 g, 1 equiv.) was added dropwise as a solution in dichloromethane (10 ml) with stirring at ambient temperature. The mixture was stirred for 1 hour at ambient temperature and concentrated to a viscous residue by evaporation to afford the crude product which was used in subsequent reactions without further purification.

Synthesis of O5'-benzyloxydicarbonyl-O3'-tert.-butyidimethylsilylthymidine, BnOX-dT-Si (6c)

O3'-tert.-Butyldimethylsilylthymidine (5) (5 g, 1.0 equiv.) was dissolved in pyridine (20 ml). Oxalic acid benzyl ester chloride (1.3 equiv.) was added with cooling (ice bath) and the reaction was continued at ambient temperature for 1 hour. Ethanol (0.5 ml) was added and the mixture was evaporated to a syrupy residue. The residue was dissolved in dichloromethane and the resultant solution was extracted with 5% sodium hydrogencarbonate solution (3 times). The organic phase was dried over sodium sulfate and evaporated to a foam. Purification by column chromatography on silica gel gave pure (98.7%) BnOX-dT-Si (6c) (5.9 g, 81% yield).

Synthesis of Oxalic Acid Cycclohexyl Ester Chloride

A precooled solution of oxalyl chloride (316.8 g, 2.5 mol) in dichloromethane (400 ml) was added to a cooled solution (ice bath) of cyclohexanol (50.0 g, 0.5 mol) in dichloromethane (100 ml). The mixture was stirred at 0° C. for 30 min, then allowed to warm to ambient temperature. The reaction was continued overnight. The mixture was concentrated on a rotary evaporator and the residue was purified by fractionated distillation under reduced pressure. The product was collected as the main fraction (68.5 g, 72%). bp 59° C./1.6 mbar; $n_{D20}$ 1.462.

Synthesis of O3'-tert.-butyldimethylsilyl-O5'-cyclo-hexyloxydicarbonylthymidine, CyOX-dT-Si (6d)

O3'-tert.-Butyldimethylsilylthymidine (5) (5 g, 1.0 equiv.) was dissolved in pyridine (20 ml). Oxalic acid cyclohexyl ester chloride (1.3 equiv.) was added with cooling (ice bath) and the reaction was continued at ambient temperature for 30 min. Ethanol (2.5 ml) was added and the mixture was evaporated to a syrupy residue. The residue was dissolved in dichloromethane and the resultant solution was extracted with 5% sodium hydrogencarbonate solution (3 times). The organic phase was dried over sodium sulfate and evaporated to a gum. The gum was treated with hexanes at ambient temperature overnight to provide a white solid which was collected by filtration. Purification by column chromatography on silica gel gave pure (99.9%) CyOX-dT-Si (6d) (5.7 g, 80% yield).

Synthesis of Oxalic Acid Phenyl Ester Chloride

Phenol (5.2 g, 1 equiv.) and oxalyl chloride (23.2 ml, 5 equiv.) were dissolved in dichloromethane (160 ml). The mixture was heated to reflux for 6 hours and concentrated to a viscous residue by evaporation. The residue was coevaporated with THF to afford the crude product which was used in subsequent reactions without further purification.

Synthesis of O3'-tert.-butyldimethylsilyl-O5'-phenoxydicarbonylthymidine, PhOX-dT-Si (6e)

O3'-tert.-Butyldimethylsilylthymidine (5) (5 g, 1.0 equiv.) was dissolved in pyridine (150 ml). Oxalic acid phenyl ester chloride (1.3 equiv.) was added with cooling (ice bath) and the reaction was continued at ambient temperature. The mixture was evaporated to a syrupy residue. The residue was dissolved in dichloromethane and the resultant solution was extracted with 5% sodium hydrogencarbonate solution (3 times). The organic phase was dried over sodium sulfate and evaporated to a foam. Purification by column chromatography on silica gel gave pure (99.3%) PhOX-dT-Si (6e) (5.2 g, 73% yield).

Synthesis of O3'-tert.-butyidimethylsilyl-O5'-(2-(4-nitrophenoxycarbonyl)benzoyl)thymidine, PSNp-dT-Si (6f)

O3'-tert.-Butyldimethylsilylthymidine (5) (5.5 g, 1.0 equiv.) was dissolved in ethylacetate (100 ml). Triethylamine (0.98 equiv.), DMAP (0.25 equiv.) and phthalic acid anhydride (1.2 equiv.) were added and the resulting mixture was heated at 50° C. for 5 hours. The mixture was stirred at ambient temperature overnight. Water (2.5 ml) was added and the reaction mixture was concentrated to a syrupy residue by evaporation. The residue was dissolved in dichloromethane (300 ml) and the solution was extracted with conc. sodium chloride solution, 10% aqueous citric acid solution and water (300 ml each). The solution was dried over sodium sulfate and evaporated to a foam to provide the crude phthalic acid O3'-silyl thymidine ester (96.8% pure by RP-HPLC). The foam was dissolved in pyridine (100 ml). 4-nitrophenyltrifluoroacetate (1.2 equiv.) was added and the resultant reaction mixture was stirred at ambient temperature overnight. The mixture was concentrated to a syrupy residue by evaporation. The residue was dissolved in ethylacetate (300 ml). The solution was extracted with 5% sodium hydrogen carbonate solution (2 times 300 ml) and water (300 ml), dried over sodium sulfate and evaporated to a foam. Purification by column chromatography on silica gel gave pure (99.7%) PSNP-dT-Si (6f) (7.7 g, 80% yield).

Synthesis of O3'-tert.-butyidimethylsilyl-O5'-(2-(2-cyanophenoxycarbonyl)benzoyl)thymidine, PSCp-dT-Si (6g)

O3'-tert.-Butyldimethylsilylthymidine (5) (15 g, 1.0 equiv.) was dissolved in ethylacetate (250 ml). Triethylamine (1.0 equiv.), DMAP (0.25 equiv.) and phthalic acid anhydride (1.2 equiv.) were added. The resulting mixture was heated at 50° C. for 3.5 hours and stirred at ambient temperature overnight. The reaction was quenched by addition of water (8 ml) and the reaction mixture was evaporated to dryness. The residue was dissolved in dichloromethane and extracted with brine (500 ml), a 10% aqueous solution of citric acid (2 times 500 ml) and water (500 ml). The organic phase was evaporated to a foam. The crude product, O3'-tert.-butyldimethylsilyl-O5'-(2-carboxybenzoyl)-thymidine was used in subsequent reactions without further purification. A portion of the crude product (500 mg, 1.0 equiv.) was dried by coevaporation with THF and dissolved in THF (5 ml). DMAP (0.2 equiv.) and N,N'-dicyclohexylcarbodiimide (1.1 equiv.) were added and the resulting yellow suspension was stirred at ambient temperature for 90 minutes. 2-Cyanophenol (1.1 equiv.) was added and the reaction mixture was stirred at ambient temperature for 3 days. Precipitated N,N'-dicyclohexylurea was removed by filtration and the filtrate was evaporated to dryness. Purification by column chromatography on silica gel (dichloromethane/ethanol, gradient elution) afforded pure (98.1%) PSCP-dT-Si (6g) (360 mg, 59% yield). ESI-MS (neg. mode) m/z 585.1 [M−H]⁻.

Example 2

Cleavage of 5'-acyl Groups with Various Aliphatic Amines

A solution of the respective 5'-acyl thymidine derivative (6a-f) (0.1 mmol, 1 ml) in the given solvent was mixed with a reagent cocktail in the same solvent containing the respective amine or amine mixture with or without additives (1 ml) to result in a deprotection reaction mixture with a concentration of 0.05 M for (6a-g). The concentration of amines and additives in the reagent cocktail were doubled with respect to the deblocking mixture to be investigated. Samples (100 µl, each) were drawn after the respective time points, diluted with acetonitrile (900 µl) and subjected to analysis by RP-HPLC. For kinetic experiments (time points 0.5-4 min) the samples (100 µl) were quenched by addition to a 12.2% solution of acetic acid in acetonitrile and cooling of the remaining mixture to 0° C. The samples were analyzed after the addition of acetonitrile (700 µl) by RP-HPLC on a Waters Novapak C18 column (4 µm, 3.9×150 mm), elution with a linear gradient from 40% to 100% A in 15 min at ambient temperature with a flow rate of 1 ml/min, detection at λ=270 nm. ACN was used as solvent A and 250 mM triethylammonium acetate (TEAA), pH 6.5, was used as solvent B. Sample injection: 4 µl. The identity of the product dT-Si (5) formed in the deprotection reactions was confirmed by coinjections with the reference: Rt 3.8 min.

Example 3

Synthesis of CyOX-dT-β-cyanoethyl-amidite (10)

Synthesis of O5'-cyclohexyloxydicarbonylthymidine, CyOX-dT

O3'-tert.-butyldimethylsilyl-O5'-cyclohexyloxydicarbonylthymidine, CyOX-dT-Si (6d) (30.4 g, 59.5 mmol) was dissolved in dichloromethane (350 ml). A solution of hydrogen fluoride in pyridine (65% HF, 16.7 ml, 600 mmol) was added and the mixture was stirred at ambient temperature for 5 hours. The reaction was quenched by the addition of solid calcium carbonate (35.3 g) and stirred for 1 hour. After removal of the solid material by filtration the organic phase was extracted with 5% sodium hydrogencarbonate solution (2 times 500 ml) and water (2 times 500 ml). The organic phase was dried over sodium sulfate and concentrated to a foam by evaporation. The foam was dissolved in dichloromethane (150 ml) and added dropwise to a mixture of hexanes and diethylether (8:2, v/v, 1800 ml). The precipitate was collected by filtration, washed with a small volume of hexanes and dried under vacuum. Further purification by column chromatography on silica gel (acetone/dichloromethane, gradient elution) afforded the product in 98.2% purity by RP-HPLC (9.0 g, 38%). $^1$H NMR (300 MHz, DMSO-d6) δ [ppm]: 11.31 (s, 1H, NH), 7.47 (d, 1H, J=1.2 Hz, H-6), 6.21 (t, 1 H, J=6.3 Hz, H-1'), 5.41 (d, 1H, J=4.2 Hz, OH-3'), 4.84-4.77 (m, 1H, cyclohexyl), 4.42-4.32 (m, 2H, $CH_2$-5'), 4.29-4.22 (m, 1H, H-3'), 4.01 (dt, 1H, J=4.2 Hz, 3.3 Hz, H-4'), 2.23-2.14 (m, 1H, H-2a'), 2.12-2.03 (m, 1H, H-2b'), 1.89-1.77 (m, 2H, cyclohexyl), 1.62-1.59 (m, 2H, cyclohexyl), 1.52-1.15 (m, 6H, cyclohexyl).

Synthesis of O3'-[2-cyanoethoxy(diisopropylamino) phosphanyl]-O5'-cyclohexyloxydicarbonylthymidine, CyOX-dT-amidite (10)

CyOX-dT (15.0 g, 37.8 mmol) and N,N-diisopropylethylamine (14.5 ml, 83.3 mmol) were dissolved in ethyl acetate (350 ml). The solution was cooled (ice bath) and chloro-2-cyanoethoxy(diisopropylamino)phosphane (9.9 g, 41.8 mmol) was added with stirring. The mixture was allowed to warm up to ambient temperature and stirring was continued for 2 hours. The reaction mixture was poured into ethyl acetate (350 ml) and was extracted with 5% sodium hydrogencarbonate solution (2 times 350 ml) and water (350 ml). The organic layer was dried over sodium sulfate and concentrated to a foam by evaporation. The foam was dissolved in dichloromethane (24 ml) and added dropwise and under stirring to hexanes (220 ml). The organic phase was separated from the secreted viscous oil by decantation. The oily product was redissolved in dichloromethane (100 ml) and concentrated to a gum by evaporation. Purification of the residue by column chromatography on silica gel (ethyl acetate/hexanes, gradient elution) afforded the product (10) in 98.8% purity by RP-HPLC (12.5 g, 55%). $^{31}$P NMR (121.5 MHz, CDCl$_3$) δ [ppm]: 149.7, 149.5, purity by P-NMR 100%. ESI-MS (pos. mode) m/z 597 [M+H]$^+$.

Example 4

Synthesis of PSNp-dT-β-cyanoethyl-amidite (11)

Synthesis of O5'-(2-(4-nitrophenoxycarbonyl)benzoyl)thymidine, PSNp-dT

O3'-tert.-butyldimethylsilyl-O5'-(2-(4-nitrophenoxycarbonyl)benzoyl)thymidine, PSNp-dT-Si (6f) (24.4 g, 39 mmol) was dissolved in dichloromethane (300 ml). Hydrogen fluoride in pyridine (65% HF, 12.6 ml, 450 mmol) was added and the mixture was stirred at ambient temperature for 5 hours. The reaction was quenched by the addition of solid calcium carbonate (25.9 g) and stirred for 1 hour. After removal of the solid material by filtration the organic phase was extracted with 5% sodium hydrogencarbonate solution (2 times 500 ml) and water (2 times 500 ml). The organic phase was dried over sodium sulfate and concentrated to a foam by evaporation. The foam was dissolved in dichloromethane (120 ml) and added dropwise to a mixture of hexanes and diethylether (8:2, v/v, 1500 ml). The precipitate was filtered off and washed with a small volume of hexanes. Further purification by column chromatography on silica gel (ethyl acetate/hexanes, gradient elution) afforded the product in 99.8% purity by RP-HPLC (18.4 g, 92%). ESI-MS (pos. mode) m/z 512 [M+H]$^+$.

Synthesis of O3'-[2-cyanoethoxy(diisopropylamino) phosphanyl]-O5'-(2-(4-nitrophenoxycarbonyl)benzoyl)thymidine, PSNp-dT-amidite (11)

PSNP-dT (17.5 g, 34.2 mmol) and N,N-diisopropylethylamine (13.1 ml, 75.2 mmol) were dissolved in ethyl acetate (500 ml). The solution was cooled and chloro-2-cyanoethoxy(diisopropylamino)phosphane (8.9 g, 37.6 mmol) was added with stirring. The mixture was allowed to warm up to ambient temperature and stirring was continued for 3 hours. The reaction mixture was poured into ethyl acetate (1000 ml) and was extracted with 5% sodium hydrogencarbonate solution (2 times 500 ml) and water (500 ml). The organic layer was dried over sodium sulfate and concentrated to dryness by evaporation. Purification by column chromatography on silica gel (ethyl acetate/hexanes, gradient elution) afforded the product (11) in 99.8% purity by RP-HPLC (20.5 g, 84%). $^1$H NMR (300 MHz, CDCl$_3$) δ [ppm]: 8.76-8.32 (m, 1H, NH), 8.31 (d, 2H, J=8.7 Hz, H-3, H-5, 4-nitrophenyl), 7.94-7.72 (m, 2H, phthalic acid), 7.71-7.52 (m, 2H, phthalic acid), 7.46 (d, 2H, J=8.7 Hz, H-2, H-6, 4-nitrophenyl), 7.14, 7.11 (2 s, 2H, 6-H), 6.32-6.25 (m, 1H, H-1'), 4.66-4.39 (m, 3H, H-3', $CH_2$-5'), 4.32-4.18 (m, 1H, H-4'), 3.88-3.41 (m, 4H, POCH$_2$, NCH (CH$_3$)$_2$), 2.64-2.37 (m, 3H, CH$_2$CN, H-2'a), 2.25-2.11 (m, 1H, H-2'b), 1.65 (s, 3H, CH$_3$-5), 1.41-0.99 (m, 12H, NCH (CH$_3$)$_2$). $^{31}$P NMR (121.5 MHz, CDCl$_3$) δ [ppm]: 149.9, 149.7, purity by P-NMR 100%. ESI-MS (pos. mode) m/z 712 [M+H]$^+$.

Example 5

Synthesis of PSCp-dT-β-cyanoethyl-amidite (12)

Synthesis of O5'-(2-(2-cyanophenoxycarbonyl)benzoyl)thymidine, PSCp-dT

O3'-tert.-butyldimethylsilyl-O5'-(2-(2-cyanophenoxycarbonyl)benzoyl)thymidine, PSCp-dT-Si (6g) (100.5 g, 166 mmol) was dissolved in dichloromethane (800 ml). Hydrogen fluoride in pyridine (70% HF, 47.4 g, 1.66 mol) was added and the mixture was stirred at ambient temperature overnight. The reaction was quenched by extraction with 10% aqueous calcium chloride solution (2 times, 600 ml and 400 ml). The organic phase was extracted with 5% aqueous sodium hydrogencarbonate solution (3 times 800 ml), a 10% aqueous solution of citric acid (3 times 800 ml) and brine (800 ml), dried over sodium sulfate, filtered and concentrated to a foam by evaporation. Purification by column chromatography on silica gel (ethylacetate/hexanes, gradient elution) afforded the product in 99.0% purity by RP-HPLC (40 g, 50%). ESI-MS (neg. mode) m/z 489.7 [M−H]$^-$, 980.9 [2M−H]$^-$.

Synthesis of O3'-[2-cyanoethoxy(diisopropylamino) phosphanyl]-O5'-(2-(2-cyanophenoxycarbonyl)benzoyl)thymidine, PSCp-dT-amidite (12)

PSCp-dT (15.0 g, 30.5 mmol) and N,N-diisopropylethylamine (12.2 ml, 67.1 mmol) were dissolved in ethyl acetate (300 ml). The solution was cooled and chloro-2-cyanoethoxy (diisopropylamino)phosphane (15.0 g, 63.4 mmol) was added with stirring. The mixture was allowed to warm up to ambient temperature and stirring was continued for 90 minutes. The reaction mixture was poured into ethyl acetate (500 ml) and was extracted with 5% sodium hydrogencarbonate solution (2 times 400 ml) and brine (400 ml). The organic layer was dried over sodium sulfate and concentrated to dryness by evaporation. The residue was dissolved in dichloromethane (20 ml). The solution was added dropwise to hexanes (250 ml) at ambient temperature with stirring to provide a biphasic mixture with a large upper layer and a small lower layer. The upper layer was decanted and the lower layer was concentrated to a syrupy residue by evaporation. The precipitation in hexanes was repeated two times as described above. Purification by column chromatography on silica gel (ethylacetate/hexanes, gradient elution) afforded the product (12) in 99.4% purity by RP-HPLC (13.0 g, 62%). $^{31}$P NMR (121.5 MHz, CDCl$_3$) δ [ppm]: 149.9, 149.7, purity by P-NMR 98.7%. UV $\lambda_{max}$ 268 nm. ESI-MS (neg. mode) m/z 689.8 [M–H]$^-$.

Example 6

Synthesis of CyOX-dT-allyl-amidite (13)

CyOX-dT (10.8 g, 27 mmol) and N,N-diisopropylethylamine (10.4 ml, 60 mmol) were dissolved in tetrahydrofurane (400 ml). The solution was cooled (ice bath) and allylchloro(diisopropylamino)phosphane (8.3 g, 30 mmol) was added with stirring. The mixture was allowed to warm up to ambient temperature and stirring was continued for 3 hours. The reaction mixture was poured into ethyl acetate (500 ml) and was extracted with 5% sodium hydrogencarbonate solution (2 times 500 ml). The organic layer was dried over sodium sulfate and concentrated to a foam by evaporation. Purification by column chromatography on silica gel (ethyl acetate/hexanes, gradient elution) afforded the product (12) in 97.1% purity by RP-HPLC (10.0 g, 63%). $^1$H NMR (300 MHz, CDCl$_3$) δ [ppm]: 8.61 (bs, 1H, NH), 7.43-7.42 (m, 1H, H-6), 6.45-6.39 (m, 1H, H-1'), 5.98-5.85 (m, 1H, CH$_2$=CH—CH$_2$), 5.30-5.28 (m, 1H, CHH$_t$=CH—CH$_2$), 5.14 (d, 1H, J=10.2 Hz, CHH$_c$=CH—CH$_2$), 4.97-4.88 (m, 1H, CH-cyclohexyl), 4.55-4.41 (m, 3H, H-3', H-4', H-5'a), 4.38-4.27 (m, 1H, H-5'b), 4.21-4.00, 3.67-3.53 (2 m, 4H, CH$_2$=CH—CH$_2$, NCH(CH$_3$)$_2$), 2.54-2.37 (m, 1H, H-2'a), 2.28-2.17 (m, 1H, H-2'b), 1.98-1.85, 1.83-1.69 (2 m, 4H, cyclohexyl), 1.91 (s, 3H, CH$_3$-5), 1.63-1.30 (m, 6H, cyclohexyl), 1.30-1.15 (m, 12H, NCH(CH$_3$)$_2$). $^{31}$P NMR (121.5 MHz, CDCl$_3$) δ [ppm]: 148.7, 149.3, purity by P-NMR 98%.

Example 7

Preparation of Thymidine Loaded CPG with an Acid Labile Linker (19)

Synthesis of 1-(4-nitrophenoxy)carbonyloxy-4-vinylbutane (17)

1,4-Butanediolmonovinylether (16) (15 g, 0.13 mol) and 1,8-diazatricyclo[2.2.2]octane (DABCO, 15.2 g, 0.13 mol) were dissolved in ethylacetate (100 ml). p-nitrophenylchloroformate (25.5 g, 0.13 mol) was dissolved in ethylacetate (100 ml) and gradually added with stirring to the reaction vessel at room temperature. The reaction mixture heated up during the addition and the reaction was continued at ambient temperature for 2 hours. The reaction mixture was extracted with 5% sodium hydrogencarbonate solution (2 times 150 ml) and water (150 ml), dried over sodium sulfate and concentrated to a viscous gum by evaporation. Purification by column chromatography on silica gel (ethyl acetate/hexanes, gradient elution) afforded the product (16) in 98.2% purity by RP-HPLC (18.2 g, 53%). $^1$H-NMR (CDCl$_3$, 300 MHz): δ [ppm]: 8.27 (d, 2H, J=9.25 Hz); 7.37 (d, 2H, J=9.28 Hz); 6.46 (dd, 1H, J=14.17, 6.74 Hz); 4.33 (t, 2H, J=6.23 Hz); 4.18 (dd, 1H, J=14.19, 2.11 Hz); 4.00 (dd, 1H, J=6.77, 2.05 Hz); 3.73 (t, 2H, J=6.08 Hz); 1.94-1.73 (m, 4H).

Synthesis of O5'-cyclohexyloxydicarbonylthymidine-O3'-[(1-(4-nitrophenoxy)carbonyloxy)-4-butyl)-oxyethyl-1] (18)

1-(4-nitrophenoxy)carbonyloxy-4-vinylbutane (17) (1.9 g, 7.1 mmol, 1.2 equiv.) was dissolved in tetrahydrofurane (40 ml). CyOX-dT-amidite (10) (2.2 g, 6.0 mmol, 1.0 equiv.) and camphorsulfonic acid CSA (0.1 g, 0.43 mmol, 0.07 equiv.) were consecutively added and the reaction was continued with stirring at room temperature for 68 hours. The reaction mixture was concentrated by evaporation under vacuum, diluted with ethylacetate (100 ml), extracted with 5% sodium hydrogencarbonate solution (2 times 75 ml), dried over sodium sulfate and concentrated to dryness by evaporation. The residue was purified by column chromatography on silica gel (ethyl acetate/hexanes, gradient elution) to afford the product (18) (0.8 g, 18%). $^1$H-NMR (CDCl$_3$, 300 MHz): δ [ppm]: 8.5 (bs, 1H); 8.28 (d, 2H, J=9.21 Hz); 7.47-7.34 (m, 3H); 6.36 (dd, 1H, J=6.36 Hz); 4.98-4.87 (m, 1H); 4.81-4.74 (m, 1H); 4.57-4.44 (m, 2H); 4.44-4.27 (m, 4H); 4.25 (q, 1H, J=5.96, 2.71 Hz); 3.69-3.52 (m, 1H); 3.52-3.38 (m, 1H); 2.46-2.29 (m, 1H); 2.29-2.11 (m, 1H); 1.98-1.21 (m, 20H).

Preparation of Thymidine Loaded CPG with an Acid Labile Linker (19)

Amino-functionalized controlled pore glass (500 mg) of 50 nm average pore diameter with a C6-spacer (6-aminohexanoic acid spacer) was immersed in a solution of (18) (17.6 mg, 28 μmol) and triethylamine (50 μl) in N,N-dimetylacetamide (4 ml). The mixture was placed on a shaker overnight at room temperature. The CPG was filtered, washed with several portions of N,N-dimetylacetamide and acetonitrile and dried under vacuum. The dried CPG was immersed in a mixture of pyridine (10 ml) and diisopropylethylamine (100 μl) and treated with oxalic acid cycclohexyl ester chloride (100 μl). The mixture was placed on a shaker overnight at room temperature. The CPG was filtered, washed with several portions of pyridine and acetonitrile and dried under vacuum. The dried CPG was immersed in a mixture of pyridine (10 ml) and diisopropylethylamine (100 μl) and treated with 4-tert.-butylphenoxyacetic acid anhydride (200 mg). The mixture was placed on a shaker for 2 hours at room temperature. The CPG was filtered, washed with several portions of pyridine and acetonitrile and dried under vacuum. 30 mg of the dried CPG were filled in a synthesizer column for an ABI Expedite (Model 8909) DNA synthesizer and subjected to a series of reaction steps on the synthesizer which included a front end deprotection step with 10% DEAEA in acetonitrile, a phosphoramidite coupling step with DMT-dT-β-cyanoethlyly amidite and an oxidation step. The CPG was washed with acetonitrile on the synthesizer and dried under vacuum. A photometric loading measurement based on the cleavage of the support bound DMT groups with trichloroacetic acid deblock solution indicated a nucleoside loading of 20 μmol/g.

Example 8

Synthesis of poly-dT-sequences with CyOX-dT-β-cyanoethyl-amidite (10) on a support with an acid labile linker (19)

The oligodeoxynucleotides $dT_{10}$ and $dT_{20}$ were prepared on the solid support (19) (loading 20 μmol/g, 10 mg, 0.2 μmol scale). The synthesis was performed on an ABI Expedite (Model 8909) DNA synthesizer. The standard DNA synthesis protocol according to the manufacturer's recommendations was modified to omit the capping steps and to insert an additional coupling step after the coupling with nucleoside phosphoramidite. The phosphoramidite of the additional coupling step was delivered from amidite port 5 which was charged with a 50 mg/ml solution of the non-nucleosidic phosphoramidite diisopropoxydiisopropylaminophosphane (14). The additional coupling step was performed in the same manner as the coupling step for the nucleoside phosphoramidite. The synthesis was performed in DMT-OFF mode. Commercial synthesis reagents for oxidation and washing steps were employed. A 10% solution of DEAEA in acetonitrile, v/v, was employed for the deblock step. The nucleoside phosphoramidite coupling steps were performed with a 50 mg/ml solution of CyOX-dT-amidite (10) in acetonitrile. A 0.25 M solution of DCI activator in acetonitrile was used as activator for the nucleoside phosphoramidite coupling and for the capping reaction with the non-nucleosidic phosphoramidite (14). After the chain assembly with the synthesizer the oligonucleotides were cleaved from the support through incubation with a 40 mM citrate buffer pH 3 (200 μl) for 24 hours at room temperature. The buffer solution was neutralized with a 0.1 M solution of sodium hydrogen carbonate (130 μl). The supernatant was separated from the CPG and evaporated to dryness in a vacuum centrifuge. The residue was dissolved in water (200 μl) and analyzed by anion-exchange HPLC (method A). The synthesis was performed twice. An average of 14.5 OD units were obtained in the synthesis of the $dT_{10}$ sequence and an average of 27.5 OD units were obtained in the synthesis of the $dT_{20}$ sequence.

Example 9

Synthesis of poly-dT-sequences with PSCp-dT-β-cyanoethyl-amidite (12) on a support with an acid labile linker (19)

The syntheses of the oligodeoxynucleotides $dT_{10}$ and $dT_{20}$ on the solid support (19) and their cleavage from the support were repeated in the same manner as described in Example 8, but the nucleoside phosphoramidite coupling steps were performed with a 50 mg/ml solution of PSCp-dT-amidite (12) in acetonitrile. In addition, the crude oligonucleotides, while still bound to the support, were treated with a solution of 10% diethylamine in acetonitrile for 30 minutes at ambient temperature followed by washing of the support with acetonitrile. The crude oligonucleotide products were analyzed by anion-exchange HPLC (method A) and reversed phase HPLC (method B). The synthesis of the $dT_{10}$-sequence was performed twice and an average of 8.6 OD units were obtained. 20.6 OD units were obtained in the synthesis of the $dT_{20}$ sequence.

Example 10

Synthesis of poly-dT-sequences with CyOX-dT-β-cyanoethyl-amidite (10) on a support with a disiloxyl linker (20)

The oligodeoxynucleotides $dT_{10}$ and $dT_{20}$ were prepared on the solid support (20) (loading 30.6 μmol/g, 33 mg, 1 μmol scale), which was detritylated prior to use by the application of std. trichloroacetic acid deblock solution. The synthesis was performed on an ABI Expedite (Model 8909) DNA synthesizer according to the manufacturer's recommendations for the synthesis of DNA in DMT-OFF mode. Commercial synthesis reagents for oxidation and washing steps were employed. Instead of capping solutions the respective ports were equipped with bottles containing acetonitrile. A 10% solution of DEAEA in acetonitrile, v/v, was employed for the deblock step. The coupling step was performed with a 0.25 M solution of DCl activator in acetonitrile and a 50 mg/ml solution of CyOX-dT-amidite (10) in acetonitrile. After the chain assembly with the synthesizer the oligonucleotides were cleaved from the support through incubation with a mixture of triethylamine trihydrofluoride/1-methyl-2-pyrrolidinone/6 (1:3:2, v/v/v, 300 μL) at ambient temperature for 1 hour. The CPG was separated and washed with water. The combined solutions containing the oligonucleotide were subjected to size exclusion chromatography on NAP10 columns. The product fractions were collected and analyzed by RP-HPLC (method B). The retention times of the products were identical to the retention times of reference oligonucleotides. The identity of the products was further confirmed by ESI-MS analysis (calculated m/z for $dT_{10}$ 2980.0; found 2980.5, calculated m/z for $dT_{20}$ 6022.0; found 6024.6). 41 OD units were obtained in the synthesis of the $dT_{10}$ sequence and 72 OD units were obtained in the synthesis of the $dT_{20}$ sequence.

Example 11

Synthesis of poly-dT-sequences with PSNp-dT-β-cyanoethyl-amidite (11) on a support with a disiloxyl linker (20)

The oligodeoxynucleotides $dT_{10}$ and $dT_{20}$ were prepared on the solid support (20) (loading 30.6 μmol/g, 33 mg, 1 μmol scale), which was detritylated prior to use by the application of std. trichloroacetic acid deblock solution. The synthesis was performed on an ABI Expedite (Model 8909) DNA synthesizer according to the manufacturer's recommendations for the synthesis of DNA in DMT-OFF mode. Commercial synthesis reagents for capping, oxidation and washing steps were employed. A 10% solution of DEAEA in acetonitrile, v/v, was employed for the deblock step. The coupling step was performed with a 0.1 M solution of activator 42 (5-(3,5-Bis(trifluoromethyl)phenyl)-1H-tetrazole) in acetonitrile and a 50 mg/ml solution of PSNP-dT-amidite (11) in acetonitrile. After the chain assembly with the synthesizer the oligonucleotides were cleaved from the support through incubation with a mixture of triethylamine trihydrofluoride/1-methyl-2-pyrrolidinone/6 (1:3:2, v/v/v, 300 μL) at ambient temperature for 1 hour. The CPG was separated and washed with water. The combined solutions containing the oligonucleotide were subjected to size exclusion chromatography with NAP10 columns. The product fractions were collected and concentrated to dryness by evaporation. The oligonucleotides were dissolved in water (2 ml) and analyzed by RP-HPLC (method B). The retention times of the products were identical to the retention times of reference oligonucleotides. The identity of the products was further confirmed by ESI-MS analysis (calculated m/z for $dT_{10}$ 2980.0; found 2980.0, calculated m/z for $dT_{20}$ 6022.0; found 6027.4). 44 OD units were obtained in the synthesis of the $dT_{10}$ sequence and 56 OD units were obtained in the synthesis of the $dT_{20}$ sequence.

Example 12

Synthesis of poly-dT-sequences with CyOX-dT-β-cyanoethyl-amidite (10) on universal support (21)

The syntheses of the oligodeoxynucleotides $dT_{10}$ and $dT_{20}$ were repeated in the same manner as described in Example 10 on the commercial universal CPG support (21) (1 µmol scale, 50 mg/ml solution of CyOX-dT-amidite (10) applied in the phosphoramidite coupling step). Prior to use the support was treated with std. trichloroacetic acid deblock solution in order to open the orthoester protective group. After the chain assembly with the synthesizer cleavage and deprotected was accomplished by incubating the support with a mixture of conc. aqueous ammonia and 0.5 M LiCl (5:1, v/v) for 6 h at 75° C. After separation of the CPG the ammonia solutions were concentrated and the remainder redissolved in water. All samples were analyzed by RP-HPLC (method B). The retention times of the products were identical to the retention times of reference oligonucleotides. The identity of the products was further confirmed by ESI-MS analysis (calculated m/z for $dT_{10}$ 2980.0; found 2979.7, calculated m/z for $dT_{20}$ 6022.0; found 6025.6). 25 OD units were obtained in the synthesis of the $dT_{10}$ sequence and 69 OD units were obtained in the synthesis of the $dT_{20}$ sequence.

Example 13

Synthesis of poly-dT-sequences with CyOX-dT-allyl-amidite (13) on universal support (21)

The oligodeoxynucleotides $dT_{10}$ and $dT_{20}$ were prepared on the commercial universal CPG support (21) (1 µmol scale). The synthesis was performed on an ABI Expedite (Model 8909) DNA synthesizer. The standard DNA synthesis protocol according to the manufacturer's recommendations was modified to omit the capping steps and to insert an additional coupling step after the coupling with nucleoside phosphoramidite. The phosphoramidite of the additional coupling step was delivered from amidite port 5 which was charged with a 50 mg/ml solution of the non-nucleosidic phosphoramidite diisopropoxydiisopropylaminophosphane (14). The additional coupling step was performed in the same manner as the coupling step for the nucleoside phosphoramidite. The synthesis was performed in DMT-OFF mode. A 0.02 M solution of 2-butanone peroxide in dichloromethane was employed for the oxidation step. The washing steps were performed with acetonitrile. A 10% solution of DEAEA in acetonitrile, v/v, was employed for the deblock step. The nucleoside phosphoramidite coupling steps were performed with a 50 mg/ml solution of CyOX-dT-allyl-amidite (13) in acetonitrile. A 0.25 M solution of DCI activator in acetonitrile was used as activator for the nucleoside phosphoramidite coupling and for the capping reaction with the non-nucleosidic phosphoramidite (14). After the chain assembly with the synthesizer cleavage and deprotected was accomplished by incubating the support with 40% aqueous methylamine solution for 6 hours at 75° C. After separation of the CPG the methylamine solutions were concentrated and the remainder redissolved in water. All samples were analyzed by RP-HPLC (method B). The retention times of the products were identical to the retention times of reference oligonucleotides. The synthesis was performed twice. An average of 51.5 OD units were obtained in the synthesis of the $dT_{10}$ sequence and an average of 93.5 OD units were obtained in the synthesis of the $dT_{20}$ sequence.

Example 14

Synthesis of CyOX-rU-β-cyanoethyl-amidites (22) and (23)

Synthesis of O5'-cyclohexyloxydicarbonyl-O2'-(4-methoxytetrahydropyran-4-yl)-uridine, CyOX-$rU_{MTHP}$ N-hydroxy-benzotriazole hydrate (7.0 g, 44.6 mmol) was dried by coevaporation with pyridine (4 times 100 ml) and dissolved in pyridine (150 ml). Oxalic acid cyclohexyl ester chloride (7.4 g, 39.1 mmol) was added dropwise with cooling (ice bath) and the resulting mixture was stirred over night at ambient temperature. The solution was concentrated to approx. 50% volume by evaporation. Acetonitrile (20 ml) was added. O2'-(4-methoxytetrahydropyran-4-yl)-uridine (10 g, 27.9 mmol) was dissolved in pyridine (150 ml) and the solution was cooled on an ice bath. The clear solution of the oxalic acid cyclohexylester derivative prepared above was added dropwise over 4 hours and the resulting reaction mixture was stirred with further cooling for 1 hour. Ethanol (20 ml) was added. The mixture was stirred for 20 minutes and was concentrated to a yellowish oil by evaporation. The oil was dissolved in ethyl acetate (500 ml) and extracted with water (4 times 75 ml). The organic phase was dried with sodium sulfate, filtered and evaporated to dryness. The syrupy residue was purified by multiple prep. HPLC on silica gel (ethanol/dichloromethane, gradient elution) to afforded the product in 99.9% purity by RP-HPLC (2.0 g, 14%). ESI-MS (neg. mode) m/z 511.1 $[M-H]^-$, calc. 511.2.

Synthesis of O3'-[2-cyanoethoxy(diisopropylamino)phosphanyl]-O5'-cyclohexyl-oxydicarbonyl-O2'-(4-methoxytetrahydropyran-4-yl)-uridine, CyOX-$rU_{MTHP}$-amidite (22)

CyOX-$rU_{MTHP}$ (1.85 g, 3.61 mmol) and N,N-diisopropylethylamine (1.26 ml, 7.2 mmol) were dissolved in ethyl acetate (30 ml). The solution was cooled (ice bath) and chloro-2-cyanoethoxy(diisopropylamino)phosphane (0.94 g, 3.9 mmol) was added with stirring. The mixture was allowed to warm up to ambient temperature and stirring was continued for 4 hours. Another portion of chloro-2-cyanoethoxy(diisopropyl-amino)phosphane (0.1 g) was added and the reaction was continued for 1 hour. The reaction mixture was diluted with ethyl acetate (150 ml) and extracted with 5% sodium hydrogencarbonate solution (3 times 30 ml) and brine (30 ml). The organic phase was dried over sodium sulfate, filtered and concentrated to a foam by evaporation. The foamy material was dissolved in a small volume of dichloromethane and the solution was added dropwise to a large excess of ice-cold hexanes. The hexane layer was decanted and the residual oil was purified by prep. HPLC on silica gel (ethyl acetate/hexanes, gradient elution) to afford the product (22) in 97.5% purity by RP-HPLC (1.5 g, 58%). ESI-MS (neg. mode) m/z 710.8 $[M-H]^-$, calc. 711.3, (pos. mode) m/z 712.9 $([M+H]^+$, calc. 713.3).

Synthesis of O2'-tert.-butyldimethylsilyl-O5'-cyclohexyloxydicarbonyl-uridine, CyOX-$rU_{TBDMS}$ N-hydroxy-benzotriazole hydrate (12.1 g, 78.8 mmol) was dried by coevaporation with pyridine (4 times 100 ml) and dissolved in pyridine (230 ml). Acetonitrile (30 ml) was added. Oxalic acid cyclohexyl ester chloride (14.9 g, 78.1 mmol) was added dropwise with cooling (ice bath) and the resulting mixture was stirred over night at ambient temperature. The solution was concentrated to approx. 50% volume by evaporation. O2'-tert.-butyldimethylsilyluridine (20 g, 55.8 mmol) was dissolved in pyridine (230 ml) and the solution was cooled on an ice bath. The clear solution of the oxalic acid cyclohexylester derivative prepared above was added dropwise over 4 hours and the resulting reaction mixture was stirred with further cooling for 30 minutes. Ethanol (30 ml) was added. The mixture was stirred for 20 minutes and was concentrated to a yellowish oil by evaporation. The oil was dissolved in ethyl acetate (800 ml) and extracted with water (4 times 400 ml). The organic phase was dried with sodium sulfate, filtered and evaporated to dryness. The syrupy residue was purified by multiple prep. HPLC on silica gel (ethylacetate/hexanes, gradient elution) to afforded the product in 96% purity by RP-HPLC (4.0 g, 14%). $^1$H NMR (300 MHz, CDCl$_3$) δ [ppm]: 8.58 (bs, 1H, NH), 7.68 (d, 1H, J=8.1 Hz, H-6), 5.86 (d, 1H, J=4.2 Hz, H-1'), 5.69 (d, 1H, J=8.1 Hz, H-5), 4.87-4.76 (m, 1H, cyclohexyl), 4.47-4.34 (m, 2H, CH$_2$-5'), 4.23-4.15 (m, 2H, H2' and H-4'), 4.04-3.96 (m, 1H, H-3'), 2.56 (d, 1H, OH-3'), 1.86-1.15 (m, 10H, cyclohexyl), 0.79 (s, 9H, tert.-butylsilyl), 0.03, 0.00 (2×s, 6H, 2×CH$_3$ silyl).

Synthesis of O2'-tert.-butyldimethylsilyl-O3'-[2-cyanoethoxy(diisopropylamino)-phosphanyl]-O5'-cyclohexyloxydicarbonyl-uridine, CyOX-rU$_{TBDMS}$-amidite (23)

CyOX-rU$_{TBDMS}$ (4.0 g, 7.8 mmol) was dissolved in a mixture of ethylacetate (60 ml) and acetonitrile (20 ml). N,N-diisopropylethylamine (3.0 ml, 17.2 mmol) was added and the solution was cooled on an ice bath. Chloro-2-cyanoethoxy (diisopropyl-amino)phosphane (2.0 g, 8.6 mmol) was added with stirring and the mixture was allowed to warm up to ambient temperature. Stirring was continued for 5 hours at ambient temperature and then the mixture was left overnight in a refrigerator. The reaction mixture was diluted with ethyl acetate (300 ml) and extracted with 5% sodium hydrogencarbonate solution (3 times 60 ml) and brine (60 ml). The organic phase was dried over sodium sulfate, filtered and concentrated to a yellowish foam by evaporation. The foamy material was dissolved in dichloromethane (7 ml) and the solution was added dropwise to hexanes (70 ml). The hexane layer was decanted and the residual oil was purified by prep. HPLC on silica gel (ethyl acetate/hexanes, gradient elution) to afford the product (23) in 94% purity by RP-HPLC (2.4 g, 43%). $^1$H NMR (300 MHz, CDCl$_3$) δ [ppm]: 8.62 (bs, 1H, NH), 7.75 (d, 1H, J=8.1 Hz, H-6), 5.84 (d, 1H, J=4.2 Hz, H-1'), 5.72 (d, 1H, J=8.1 Hz, H-5), 4.90-4.78 (m, 1H, cyclohexyl), 4.51/4.47 (m/m, 1H, H-4'), 4.43-4.37 (m, 2H, CH$_2$-5'), 4.28/4.20 (t/t, 1H, H-2'), 4.14-4.01 (m, 1H, H-3'), 3.88-3.46 (m, 4H, POCH$_2$, NCH(CH$_3$)$_2$), 2.53 (dt, 2H, CH$_2$CN), 1.90-1.79 (m, 2H, cyclohexyl), 1.77-1.66 (m, 2H, cyclohexyl), 1.56-1.15 (m, 6H, cyclohexyl), 1.13-1.01 (m, 12H, NCH(CH$_3$)$_2$), 0.80 (s, 9H, tert.-butylsilyl), 0.05, 0.03, 0.00 (3×s, 6H, 2×CH$_3$ silyl). $^{31}$P NMR (121.5 MHz, CDCl$_3$) δ [ppm]: 150.8, 150.3, purity by P-NMR 99.4%. ESI-MS (neg. mode) m/z 711.3 [M−H]$^-$, calc. 711.3.

Example 15

Synthesis of a poly-rU-sequence with CyOX-rU$_{TBDMS}$-β-cyanoethyl-amidite (23)

The oligonucleotide 5'-rU$_5$dT-3' was prepared on support (19) (0.2 μmol scale). The synthesis was performed on an ABI Expedite (Model 8909) DNA synthesizer in duplicate. The standard RNA synthesis protocol according to the manufacturer's recommendations was modified to omit the capping steps and to insert an additional coupling step after the coupling with nucleoside phosphoramidite. The phosphoramidite of the additional coupling step was delivered from amidite port 5 which was charged with a 50 mg/ml solution of the non-nucleosidic phosphoramidite diisopropoxy-diisopropylaminophosphane (14). The additional coupling step was performed in the same manner as the coupling step for a DNA phosphoramidite as recommended by the manufacturer of the instrument. The synthesis was performed in DMT-OFF mode. Commercial synthesis reagents for oxidation and washing steps were employed. Instead of capping solutions the respective ports were equipped with bottles containing acetonitrile. A 20% solution of 2-methoxyethylamine in acetonitrile, v/v, was employed for the deblock step. The nucleoside phosphoramidite coupling steps were performed with a 50 mg/ml solution of CyOX-rU$_{TBDMS}$-amidite (23) in acetonitrile. A 0.25 M solution of DCI activator in acetonitrile was used as activator for the nucleoside phosphoramidite coupling and for the capping reaction with the non-nucleosidic phosphoramidite (14). After the chain assembly with the synthesizer the crude oligonucleotides, while still bound to the support, were treated with a solution of 10% diethylamine in acetonitrile for 30 minutes at ambient temperature followed by washing of the support with acetonitrile. Cleavage and deprotection was accomplished through incubation with a 40 mM citrate buffer pH 3 (200 μl) for 16 hours at 40° C. The buffer solution was neutralized with a 0.1 M solution of sodium hydrogen carbonate (160 μl). The supernatant was separated from the CPG and evaporated to dryness in a vacuum centrifuge. The residue was treated with a 0.5 M solution of tetra-n-butylammonium fluoride in THF (0.5 ml) overnight at ambient temperature. 2 M TEAA buffer (0.5 ml) and water (0.5 ml) were added and the solution containing the oligonucleotide was subjected to size exclusion chromatography on a NAP10 column. Product fractions were collected and analyzed by RP-HPLC (method B). The product had a purity of 45% by RP-HPLC. The identity of the product was confirmed by ESI-MS analysis: calculated m/z for 5'-rU$_5$dT-3' 1773.1. found 1773.7.

Example 16

Synthesis of CyOX-dA(mmt)-β-cyanoethyl-amidite (24)

Synthesis of N6-monomethoxytrityldeoxyadenosine, dA(mmt)

Deoxyadenosine hydrate dA×H$_2$O (50 g, 186 mmol.) was dried by coevaporation with pyridine and acetonitrile, and suspended in acetonitrile (200 ml). 1,1,1,3,3,3-hexamethyldisilazane (96 ml, 74.9 g, 465 mmol) was added and the resulting suspension was stirred over night at ambient temperature. The reaction mixture was concentrated to dryness by evaporation. The residue was dried by coevaporation with pyridine and dissolved in pyridine (260 ml). The solution was cooled on an ice bath and monomethoxytritylchloride (54.5 g, 177 mmol) was added. The reaction mixture was kept in a refrigerator at appr. 4° C. for 3 days. Additional portions of monomethoxytritylchloride (2 times 13.6 g, 45 mmol) were added successively in 24-hour time intervals while the reaction mixture was stirred at ambient temperature. The reaction mixture was treated with N-methylmorpholine (30 ml), stirred at ambient temperature for 30 minutes and evaporated to dryness. The residue was dissolved in ethylacetate (330 ml) and extracted with water (200 ml), 5% aqueous sodium hydrogencarbonate solution (2 times 200 ml) and brine (200 ml). The organic phase was concentrated to dryness by evaporation. The residue was dissolved in pyridine (100 ml) and water (20 ml), and stirred at 40° C. for 2 days. The solution was concentrated to a foam by evaporation. Purification by column chromatography on silica gel (acetone/dichloromethane, gradient elution) afforded the product in 99.9% purity by RP-HPLC (70 g, 67%). UV $\lambda_{max}$ 272 nm.

Synthesis of O5'-cyclohexyloxydicarbonyl-N6-monomethoxytrityldeoxyadenosine, CyOX-dA(mmt)

N-hydroxy-benzotriazole hydrate (8.3 g, 63 mmol) was dried by coevaporation with pyridine and dissolved in pyridine (600 ml). Oxalic acid cyclohexyl ester chloride (13 g, 69 mmol) was added dropwise with cooling (ice bath) and the resulting mixture was stirred over night at ambient temperature. The slightly orange colored solution was concentrated to a volume of appr. 250 ml by evaporation. Acetonitrile (120 ml) was added. dA(mmt) (30 g, 57.3 mmol) was dissolved in pyridine (1000 ml) and the solution was cooled to –10° C. The clear solution of the oxalic acid cyclohexylester derivative prepared above was added dropwise and the resulting reaction mixture was stirred at –10° C. for 90 minutes. Methanol (100 ml) was added. The mixture was allowed to warm up to ambient temperature with stirring and was concentrated to an oil by evaporation. The oil was dissolved in dichloromethane (500 ml) and extracted with 5% sodium hydrogencarbonate solution (3 times 300 ml). The organic phase was dried with sodium sulfate, filtered and evaporated to a syrupy residue. Purification by column chromatography on silica gel (THF/dichloromethane, gradient elution) afforded the product in 99.1% purity by RP-HPLC (22 g, 57%). UV $\lambda_{max}$ 272 nm. ESI-MS (neg. mode) m/z 676.3 [M–H]$^-$, calc. 676.4.

Synthesis of O3'-[2-cyanoethoxy(diisopropylamino)phosphanyl]-O5'-cyclohexyl-oxydicarbonyl-N6-monomethoxytrityldeoxyadenosine, CyOX-dA(mmt)-amidite (25)

CyOX-dA(mmt) (5.0 g, 7.4 mmol) and N,N-diisopropyl-ethyl-amine (5.9 ml, 16.3 mmol) were dissolved in ethyl acetate (150 ml). The solution was cooled (ice bath) and chloro-2-cyanoethoxy(diisopropylamino)phosphane (2.1 g, 9 mmol) was added with stirring. The mixture was allowed to warm up to ambient temperature and stirring was continued for 90 minutes. The reaction mixture was poured into ethyl acetate (150 ml) and extracted with 5% sodium hydrogencarbonate solution (2 times 200 ml) and water (2 times 100 ml). The organic phase was dried over sodium sulfate, filtered and concentrated to a foam by evaporation. Purification by column chromatography on silica gel (ethylacetate/hexanes, gradient elution) afforded the product in 99.4% purity by RP-HPLC (5.0 g, 77%). $^{31}$P NMR (121 MHz, CDCl$_3$) δ [ppm]: 149.7, 149.6 ppm, purity by P-NMR 98.9%. UV $\lambda_{max}$ 272 nm. ESI-MS (neg. mode) m/z 876.5 [M–H]$^-$, calc. 876.4.

Example 17

Synthesis of PSCp-dA(mmt)-β-cyanoethyl-amidite (24)

Synthesis of O3'-tert.-butyldimethylsilyl-O5'-dimethoxytrityldeoxyadenosine, DMT-dA-Si O3'-tert.-Butyldimethylsilyl-N6-(4-tert.-butylphenoxy)acetyl-O5'-dimethoxytrityl-deoxyadenosine, DMT-dA(tac)-Si (540 g, 0.67 mol) was dissolved in dichloromethane (2.0 ltr.). 2-(N,N-diethylamino)ethylamine (183 g, 1.68 mol) were added and the resulting reaction mixture was stirred at ambient temperature for 120 minutes. The mixture was extracted with a 10% aqueous solution of citric acid (2 times 1 ltr.) and water (1 ltr.). The organic phase was dried over sodium sulfate and concentrated by evaporation to a foam, which was used in subsequent reactions without further purification. Yield 440 g (quant.). Purity by RP-HPLC 91%. UV $\lambda_{max}$ 237 nm, $\lambda_{sh}$ appr. 260 nm.

Synthesis of O3'-tert.-butyidimethylsilyideoxyadenosine, dA-Si

DMT-dA-Si (440 g, 0.66 mol) was dissolved in acetonitrile (2.5 ltr.). A solution of trichloroacetic acid in dichloromethane (580 g trichloroacetic acid in 5.8 ltr. dichloromethane) was added and the resulting orange colored solution was stirred at ambient temperature for 90 minutes. Solid sodium hydrogencarbonate was cautiously added until the evolution of gas ceased. The mixture was extracted with 5% aqueous sodium hydrogencarbonate solution (5 ltr.) and water (5 ltr.). The organic phase was dried over sodium sulfate and concentrated to a syrupy residue by evaporation. The residue was dissolved in dichloromethane (1.5 ltr.) and the product was precipitated from this solution through the addition of hexanes (17 ltr.). The product was collected by filtration and used in subsequent reactions without further purification. Yield 85 g (35%). Purity by RP-HPLC 91%. UV $\lambda_{max}$ 260 nm. $^1$H NMR (300 MHz, DMSO-d$_6$) δ [ppm]: 8.23, 8.01 (2×s, 2×1 H, H-2 and H-8), 7.18 (s, 2H, NH$_2$), 6.21 (t, 1H, H-1'), 5.14 (t, 1H, OH-5'), 4.48 (m, 1H, H-3'), 3.76 (m, 1H, H-4'), 3.52-3.37 (m, 2H, H-5'), 2.81 (m, 1H, H-2'a), 2.15 (m, 1H, H-2'b). ESI-MS (pos. mode) m/z 366.2 [M+H]$^+$.

Synthesis of O3'-tert.-butyldimethylsilyl-N6-monomethoxytrityldeoxyadenosine, dA(mmt)-Si dA-Si (85 g, 233 mmol) was suspended in acetonitrile (500 ml). 1,1,1,3,3,3-Hexamethyldisilazane (60 ml, 291 mmol) was added and the suspension became a slightly cloudy solution. The reaction mixture was stirred at ambient temperature for 4 hours. Precipitation of a white solid occurred. The mixture was evaporated to dryness and coevaporated twice with pyridine. The residue was dissolved in pyridine (500 ml) and monomethoxytritylchloride (108 g, 350 mmol) was added at ambient temperature. The resulting homogeneous solution was stirred for 24 hours at ambient temperature. Additional monomethoxytritylchloride (21.6 g, 70 mmol) was added and the reaction was stirred at 35° C. overnight followed by 3 days at ambient temperature. N-Methyl-morpholine (50 ml) was added and the reaction mixture was concentrated to a syrupy residue by evaporation. The residue was dissolved in ethylacetate (1.0 ltr.) and the resulting solution was extracted with water (500 ml), 5% aqueous sodium hydrogencarbonate solution (2 times 500 ml) and brine (500 ml). The organic phase was dried over sodium sulfate, filtered and concentrated by evaporation to an oil. The oil was dissolved in pyridine (2.0 ltr.). Water (1.0 ltr.) was added and the mixture was stirred at 40° C. for 24 hours followed by evaporation to dryness. Purification by column chromatography on silica gel (ethylacetate/hexanes, gradient elution) afforded the product in 97.3% purity by RP-HPLC (110 g, 68%).

Synthesis of O3'-tert-butyidimethylsilyl-O5'-(2-carboxybenzoyl)-N6-monomethoxy-trityldeoxyadenosine, PS-dA(mmt)-Si dA(mmt)-Si (110 g, 172 mmol) was dissolved in ethylacetate (500 ml). Triethylamine (23.8 ml, 172 mmol), DMAP (5.3 g, 43 mmol) and phthalic acid anhydride (30.7 g, 206 mmol) were added successively with stirring. The homogeneous solution was stirred at 50° C. for 4 hours. The reaction mixture was cooled to ambient temperature and extracted with a 5% aqueous solution of citric acid (500 ml), water (2 times 500 ml) and saturated sodium chloride solution (300 ml). The organic phase was dried over sodium sulfate, filtered, and concentrated by evaporation to a foam, which was used in subsequent reactions without further purification. Yield 145 g (quant.). Purity by RP-HPLC 96%. UV $\lambda_{max}$ 271 nm.

Synthesis of O5'-(2-carboxybenzoyl)-N6-monomethoxytrityldeoxyadenosine, PS-dA(mmt)

PS-dA(mmt)-Si (140 g, 178 mmol) was dissolved in dichloromethane (1.2 ltr.). Pyridine (128 ml) and hydrogen fluoride in pyridine (70% HF, 64 g, appr. 12.5 equiv.) were added and the orange colored mixture was stirred at ambient temperature for 28 hours. The reaction mixture was diluted was dichloromethane (1.0 ltr.) and the reaction was quenched by extraction with 20% aqueous calcium chloride solution (1.0 ltr.). The phases were separated after the addition of isopropanol (300 ml) and the organic phase was extracted with water (2 times 1.0 ltr.). The organic phase was dried over sodium sulfate, filtered, and concentrated by evaporation to a foam, which was used in subsequent reactions without further purification. Yield 112 g (94%). Purity by RP-HPLC 76%.

Synthesis of O5'-(2-(2-cyanophenoxycarbonyl)benzoyl)-N6-monomethoxytrityl-deoxyadenosine, PSCP-dA(mmt)

PS-dA(mmt) (110 g, 164 mmol) was dried by coevaporation with pyridine and dissolved in pyridine (500 ml). N,N-Diisopropylethylamine (46 ml, 271 mmol) was added and the resulting solution was cooled on an ice bath. 2-Cyanophenyl-trifluoroacetate (61.7 g, 287 mmol) was added dropwise over 15 minutes with stirring. The mixture was allowed to warm up to ambient temperature and stirring was continued overnight. A second portion of 2-cyanophenyltrifluoracetate (24 g, 112 mmol) was added without cooling and the reaction mixture was stirred at ambient temperature for 2 hours. The reaction mixture was concentrated to an oil by evaporation. The oil was dissolved in ethylacetate (1.4 ltr.) and the solution was extracted with saturated aqueous sodium hydrogencarbonate solution (2 times 700 ml), a 5% aqueous solution of citric acid (700 ml), water (2 times 700 ml) and brine (500 ml). The organic phase was dried over sodium sulfate, filtered and concentrated to a foam by evaporation. Purification by column chromatography on silica gel (ethylacetate/hexanes, gradient elution) afforded the product in 99.0% purity by RP-HPLC (69 g, 55%).

Synthesis of O3'-[2-cyanoethoxy(diisopropylamino)phosphanyl]-O5'-(2-(2-cyano-phenoxycarbonyl)benzoyl)-N6-monomethoxytrityldeoxyadenosine, PSCp-dA(mmt)-amidite (25)

PSCp-dA(mmt) (15.0 g, 19.4 mmol) and N,N-diisopropylethylamine (7.5 ml, 43 mmol) were dissolved in ethylacetate (220 ml). The solution was cooled on an ice bath and chloro-2-cyanoethoxy(diisopropylamino)phosphane (5.1 g, 21.5 mmol) was added with stirring. The mixture was allowed to warm up to ambient temperature and stirring was continued for 3 hours. The reaction mixture was diluted with ethylacetate (100 ml) and extracted with 5% aqueous sodium hydrogencarbonate solution (2 times 100 ml) and brine (100 ml). The organic phase was dried over sodium sulfate and concentrated to a syrupy residue by evaporation. The residue was dissolved in dichloromethane (20 ml). The solution was added dropwise to hexanes (250 ml) at ambient temperature with stirring to provide a biphasic mixture with a large upper layer and a small lower layer. The upper layer was decanted and the lower layer was concentrated to a syrupy residue by evaporation. The precipitation in hexanes was repeated two times as described above. Purification by column chromatography on silica gel (ethylacetate/hexanes, gradient elution) afforded the product in 98.6% purity by RP-HPLC (12.5 g, 66%). $^{31}$P NMR (121.5 MHz, CDCl$_3$) δ [ppm]: 149.56, 149.67, purity by P-NMR 99.9%. UV $\lambda_{max}$ 273 nm. ESI-MS (pos. mode) m/z 973.2 [M+H]$^+$.

Example 18

Synthesis of poly-dA-sequences with CyOX-dA-β-cyanoethyl-amidite (24)

The oligodeoxynucleotides 5'-dA$_9$dT-3' was prepared on solid support (19) (0.2 µmol scale). The synthesis was performed on an ABI Expedite (Model 8909) DNA synthesizer. The standard DNA synthesis protocol according to the manufacturer's recommendations was modified with respect to the capping step as described in Example 8. The synthesis was performed in DMT-OFF mode. Commercial synthesis reagents for oxidation and washing steps were employed. Either a 10% solution of 2-methoxy-ethylamine in acetonitrile, v/v, or a 10% solution of N,N'-dimethylethylamine in acetonitrile, v/v, was employed for the deblock step. The nucleoside phosphoramidite coupling steps were performed with a 50 mg/ml solution of CyOX-dA(mmt)-amidite (24) in acetonitrile. A 0.25 M solution of DCI activator in acetonitrile was used as activator for the nucleoside phosphoramidite coupling and for the capping reaction with the non-nucleosidic phosphoramidite (14). After the chain assembly with the synthesizer the crude oligonucleotides, while still bound to the support, were treated with a solution of 10% diethylamine in acetonitrile for 30 minutes at ambient temperature followed by washing of the support with acetonitrile. Cleavage and deprotection was accomplished through incubation with a 40 mM citrate buffer pH 3 (200 µl) for 16 hours at 40° C. The buffer solution was neutralized with a 0.1 M solution of sodium hydrogen carbonate (160 µl). The supernatant was separated from the CPG and evaporated to dryness in a vacuum centrifuge. The residue was dissolved in water (200 µl) and analyzed by anion-exchange HPLC (method A). The retention time of the product was identical to the retention time of a reference oligonucleotide for both syntheses. The product obtained with 20% 2-methoxyethylamin as deblocking reagent had a purity of 48% by AX-HPLC and the product obtained with 10% N,N'-dimethylethylamine as deblocking reagent had purity of 23% by AX-HPLC. The identity of the product was further confirmed by ESI-MS analysis (calculated m/z for 5'-dA$_9$dT-3' 3061.1. found 3063.4 for the product prepared with 2-methoxyethylamine as deblocking reagent and 3063.5 for the product prepared with N,N'-dimethylethylamine as deblocking reagent.

Example 19

Synthesis of PSCp-dC(mmt)-β-cyanoethyl-amidite (26)

Synthesis of O5',O3'-bis(tert.-butyldimethylsilyl)-deoxycytidine, Si-dC-Si

Deoxycytidine hydrochloride, dC×HCl (500 g, 1.90 mol) was dissolved in DMF (1.5 ltr.) at ambient temperature. Triethylamine (260 ml, 1.9 mol), a solution of tert-butyldimethylsilylchloride (860 g, 5.7 mol) in THF (1.7 ltr.), and imidazole (460 g, 6.8 mol) were added successively to the stirred solution. The resulting heterogeneous mixture was temporarily cooled on an ice bath and then stirred at ambient temperature overnight. Ethanol (500 ml) was added and stirring was continued for 15 min. The reaction mixture was filtered and the residue on the filter was washed with THF (2 ltr.). The filtrates were combined and evaporated to dryness under vacuum to give a crystalline mass. Ethylacetate (1 ltr.), diethylether (2 ltr.) and water were added and the mixture was shaken until all solids were dissolved. The organic phase was washed with a 5% aqueous solution of citric acid (2 times 1 ltr.), water (1 ltr.) and acetonitrile (500 ml), dried over sodium sulfate, filtered and evaporated to a foam. Yield 897 g (quant.). Purity by RP-HPLC 97.8%. UV $\lambda_{max}$ 274 nm.

Synthesis of O3'-tert.-butyldimethylsilyldeoxycytidine, dC-Si

Si-dC-Si (865 g, 1.90 mol) was dissolved in THF (3.5 ltr.). The solution was cooled on an ice-bath and a mixture of trifluoroacetic acid and water (1/1, v/v, 1160 ml) was added slowly. The reaction mixture was stirred with continued cooling for 3.5 hours and cautiously treated with saturated aqueous sodium hydrogencarbonate solution (2 ltr.). The mixture was diluted with ethylacetate (10 ltr.) and the organic phase was washed with 5% aqueous sodium hydrogencarbonate solution (2 ltr.) and water (2 ltr.), dried over sodium sulfate, filtered and concentrated to dryness by evaporation. The residue was triturated with tert.-butylmethylether (1 ltr.). Solid material was filtered off, washed with additional tert.-butylmethylether (1 ltr.) on the filter and dried under vacuum. Yield 215 g (33%). Purity by RP-HPLC 99.6%. $^1$H NMR (300 MHz, DMSO-$d_6$) δ [ppm]: 7.69 (d, 1H, J=7.5 Hz, H-6), 7.08 (s, 2H, NH$_2$), 6.08 (t, 1H, J=6.3 Hz, H-1'), 5.65 (d, 1H, J=7.5 Hz, H-5), 4.95 (t, 1H, J=6.8 Hz, OH-5'), 4.31 (m, 1H, H-3'), 3.68 (m, 1H, H-4'), 3.51-3.41 (m, 2H, CH$_2$-5'), 2.05-1.89 (m, 2H, H-2'), 0.80 (s, 9H, tert.-butylsilyl), 0.00 (s, 6H, CH$_3$ silyl).

Synthesis of O3'-tert.-butyldimethylsilyl-N4-monomethoxytrityldeoxycytidine, dC(mmt)-Si dC-Si (230 g, 0.67 mol) was dried by coevaporation with pyridine and dissolved in pyridine (1.0 ltr.). 1,1,1,3,3,3-Hexamethyldisilazane (155 ml, 0.74 mol) was added and the resulting solution was stirred at ambient temperature overnight. The solution was evaporated to dryness and coevaporated with toluene. The residue was dissolved in dichloromethane (1.5 ltr.). Triethylamine (188 ml, 1.34 mol), DMAP (3.3 g, 27 mmol) and monomethoxytritylchloride (400 g, 1.27 mol) were added successively with stirring at ambient temperature. The resulting homogeneous solution was stirred for 24 hours. Additional triethylamine (24 ml, 0.17 mol) and monomethoxytritylchloride (50 g, 0.16 mol) were added and the reaction was stirred at 35° C. overnight. A mixture of pyridine and water (1 ltr., 1/1, v/v) was added and stirring of the resulting biphasic mixture was continued at ambient temperature for 2 hours. The phases were separated. The aqueous phase was extracted with dichloromethane (500 ml). The combined organic phases were washed with water (500 ml) and evaporated to an oil. The oil was dissolved in THF (3.5 ltr.). A 10% aqueous solution of citric acid (720 ml) was added and the resulting mixture was stirred at ambient temperature for 90 minutes. The reaction mixture was diluted with ethylacetate (5.5 ltr.) and extracted with 5% aqueous sodium hydrogencarbonate solution (2 times 3 ltr.). The organic phase was dried over sodium sulfate, filtered and concentrated to a foam by evaporation. Purification by column chromatography on silica gel (ethylacetate/hexanes, gradient elution) afforded the product in 99.6% purity by RP-HPLC (119 g). A second fraction with 91% purity by RP-HPLC was additionally obtained (50 g). Yield overall 169 g (41%). $^1$H NMR (300 MHz, DMSO-$d_6$) δ [ppm]: 8.36 (s, 1H, NH), 7.62 (d, 1H, J=7.2 Hz, H-6), 7.19-7.08 (m, 13H, H$_{Ar}$ and NH), 6.78 (d, 2H, J=8.1 Hz, H$_{Ar}$), 6.20 (d, 1H, J=6.9 Hz, H-5), 5.98 (m, 1H, H-1'), 4.93 (s, 1H, OH-5'), 4.29 (m, 1H, H-3'), 3.66 (m, 4H, OCH$_3$ and H-4'), 3.45 (m, 2H, CH$_2$-5'), 1.93 (m, 2H, H-2'), 0.80 (s, 9H, tert.-butylsilyl), 0.00 (s, 6H, CH$_3$ silyl). ESI-MS (neg. mode) m/z 611.9 [M−H]$^-$.

Synthesis of O3'-tert.-butyldimethylsilyl-O5'-(2-carboxybenzoyl)-N4-monomethoxy-trityldeoxycytidine, PS-dC(mmt)-Si dC(mmt)-Si (42 g, 68.5 mmol) was dissolved in ethylacetate (420 ml). Triethylamine (9.6 ml, 68.5 mmol), DMAP (2.1 g, 17.1 mmol) and phthalic acid anhydride (12.2 g, 82.2 mmol) were added successively with stirring. The homogeneous solution was stirred at 50° C. for 4 hours. The reaction mixture was cooled to ambient temperature and extracted with a 5% aqueous solution of citric acid (500 ml), water (1.5 ltr.) and saturated sodium chloride solution. The organic phase was dried over sodium sulfate, filtered, and concentrated by evaporation to a foam, which was used in subsequent reactions without further purification. Yield 58 g (quant.). Purity by RP-HPLC 95%. UV $\lambda_{max}$ 279 nm.

Synthesis of O5'-(2-carboxybenzoyl)-N4-monomethoxytrityldeoxycytidine, PS-dC(mmt)

PS-dC(mmt)-Si (78 g, 102 mmol) was dissolved in dichloromethane (780 ml). Pyridine (66 ml) and hydrogen fluoride in pyridine (70% HF, 47 ml, appr. 18 equiv.) were added and the orange colored mixture was stirred at ambient temperature overnight. The reaction was quenched by the addition of 20% aqueous calcium chloride solution (750 ml) and vigorously stirred for 15 minutes. The phases were separated and the organic phase was extracted with 20% aqueous calcium chloride solution (300 ml) and water (2 times 300 ml), dried over sodium sulfate, filtered and concentrated by evaporation to a pink colored foam, which was used in subsequent reactions without further purification. Yield 56 g (88%). Purity by RP-HPLC 92%. ESI-MS (neg. mode) m/z 645.9 [M−H]$^-$.

Synthesis of O5'-(2-(2-cyanophenoxycarbonyl)benzoyl)-N4-monomethoxytrityl-deoxycytidine, PSCp-dC(mmt)

PS-dC(mmt) (55 g, 85 mmol) was dried by coevaporation with pyridine and dissolved in pyridine (350 ml). N,N-Diisopropylethylamine (30 ml, 170 mmol) and 2-cyanophenyltrifluoroacetate (36.6 g, 170 mmol) were added and the resulting solution was stirred at ambient temperature overnight. The reaction mixture was concentrated to an oil by evaporation. The oil was dissolved in ethylacetate (1000 ml) and the solution was extracted with 5% aqueous sodium hydrogencarbonate solution (2 times 500 ml), a 10% aqueous solution of citric acid (500 ml) and water (500 ml). The organic phase was dried over sodium sulfate, filtered and evaporated to dryness. Purification by column chromatography on silica gel (ethylacetate/hexanes, gradient elution) afforded the product in 99.7% purity by RP-HPLC (49 g, 77%). $^1$H NMR (300 MHz, DMSO-$d_6$) δ [ppm]: 8.40 (s, 1H, NH), 8.01-7.79 (m, 6H, $H_{Ar}$), 7.59-7.45 (m, 3H, H-6 and $H_{Ar}$), 7.28-7.11 (m, 13H, $H_{Ar}$ and NH), 6.82 (d, 2H, J=8.4 Hz, $H_{Ar}$), 6.16 (d, 1H, J=7.5 Hz, H-5), 6.06 (t, 1H, H-1'), 5.39 (d, 1H, J=4.5 Hz, OH-3'), 4.47-4.35 (m, 2H, H-5'), 4.21 (m, 1H, H-3'), 3.98 (m, 1H, H-4'), 3.70 (s, 3H, $OCH_3$), 2.12-1.94 (m, 2H, H-2'). ESI-MS (neg. mode) m/z 746.9 [M−H]⁻.

Synthesis of O3'-[2-cyanoethoxy(diisopropylamino) phosphanyl]-O5'-(2-(2-cyano-phenoxycarbonyl)benzoyl)-N4-monomethoxytrityldeoxycytidine, PSCp-dC(mmt)-amidite (26)

PSCp-dC(mmt) (15.0 g, 20.0 mmol) and N,N-diisopropylethylamine (7.7 ml, 44 mmol) were dissolved in ethylacetate (220 ml). The solution was cooled on an ice bath and chloro-2-cyanoethoxy(diisopropylamino)phosphane (5.2 g, 22 mmol) was added with stirring. The mixture was allowed to warm up to ambient temperature and stirring was continued for 60 minutes. The reaction mixture was diluted with ethylacetate (100 ml) and extracted with 5% aqueous sodium hydrogencarbonate solution (2 times 200 ml) and brine (200 ml). The organic phase was dried over sodium sulfate and concentrated to a syrupy residue by evaporation. The residue was dissolved in dichloromethane (19 ml). The solution was added dropwise to hexanes (190 ml) at ambient temperature with stirring to provide a biphasic mixture with a large upper layer and a small lower layer. The upper layer was decanted and the lower layer was concentrated to a syrupy residue by evaporation. Purification by column chromatography on silica gel (ethylacetate/hexanes, gradient elution) afforded the product in 96.2% purity by RP-HPLC (6.3 g, 33%). $^{31}$P NMR (121.5 MHz, $CDCl_3$) δ [ppm]: 149.69, 149.73, purity by P-NMR 97.8%. UV $\lambda_{max}$ 278 nm. ESI-MS (neg. mode) m/z 947.1 [M−H]⁻.

Example 20

Synthesis of PSCp-dG(tac)-β-cyanoethyl-amidite (27)

Synthesis of O3',O5'-bis-tert.-butyldimethylsilyl-N2-(4-tert.-butylphenoxy)acetyl-deoxyguanosine, Si-dG(tac)-Si N2-(4-tert.-butylphenoxy)acetyldesoxyguanosine, dG(tac) (52.1 g, 114 mmol) was dissolved in DMF (100 ml). Tert.-butyldimethylsilyl chloride (68.7 g, 456 mmol) was added as a solution in tetrahydrofurane (300 ml), followed by imidazole (54.3 g, 800 mmol). The mixture was stirred overnight at ambient temperature. Another portion of tert.-butyldimethylsilyl chloride (4 g, 28 mmol) was added and stirring was continued for 90 minutes. The reaction was quenched by addition of ethanol (50 ml). Precipitated salts were filtered off and washed with a small amount of tetrahydrofurane. The filtrate was concentrated to an oil by evaporation. The oil was dissolved in 1000 ml of ethyl acetate and the resulting solution was extracted with a 5% aqueous solution of citric acid (2 times 200 ml), water (2 times 200 ml) and brine (200 ml). The organic phase was dried over sodium sulfate, filtered, and evaporated to a slightly yellow foam, which was used in subsequent reactions without further purification. Yield 80 g (quant.). Purity by RP-HPLC 94.5%. $^1$H-NMR (300 MHz, DMSO-$d_6$), δ [ppm]: 11.75 (s, 2H, 2×NH), 8.18 (s, 1H, H-8), 7.27 (d, 2H, $H_{Ar}$(tac), J=9.0 Hz), 6.85 (d, 2H, $H_{Ar}$(tac), J=9.0 Hz), 6.18 (t, 1H, J=6.7 Hz, H-1'), 4.79 (s, 2H, $CH_2$ (tac)), 4.53-4.45 (m, 1H, H-3'), 3.86-3.79 (m, 1H, H-4'), 3.73-3.58 (m, 2H, $CH_2$-5'), 2.76-2.64 (m, 1H, H-2'a), 2.29 (ddd, 1H, J1=13.2 Hz, J2=6.0 Hz, J3=3.6 Hz, H-2'b), 1.22 (s, 9H, tert.-butyl (tac)), 0.86, 0.83 (2×s, 2×9H, 2×tert.-butylsilyl), 0.08, 0.01 (2×s, 12H, 4×$CH_3$ silyl).

Synthesis of O3'-tert.-butyldimethylsilyl-N2-(4-tert.-butylphenoxy)acetyl-deoxyguanosine, dG(tac)-Si Si-dG(tac)-Si (80.0 g, 117 mmol) was dissolved in tetrahydrofurane (600 ml) and cooled in an ice bath. 1.5 M aqueous trichloroacetic acid (156 ml, 234 mmol) was added with stirring and the reaction was continued under cooling for 7 hours. The mixture was diluted with ethyl acetate (1000 ml) and extracted with 5% aqueous sodium hydrogencarbonate solution (4 times 200 ml), water (250 ml) and brine (250 ml). The organic phase was dried over sodium sulfate, filtered and evaporated to a yellow foam, which was used in subsequent reactions without further purification. Yield 80 g (quant.). Purity by RP-HPLC 91.9%. $^1$H-NMR (300 MHz, DMSO-$d_6$), δ [ppm]: 11.67 (s, 2H, 2×NH), 8.16 (s, 1H, H-8), 7.20 (d, 2H, $H_{Ar}$(tac), J=8.7 Hz), 6.78 (d, 2H, $H_{Ar}$(tac), J=9.0 Hz), 6.18 (dd, 1H, H-1', J1=7.8 Hz, J2=6.0 Hz), 4.90 (t, 1H, 5'OH, J=5.4 Hz), 4.72 (s, 2H, $CH_2$ (tac)), 4.46-4.40 (m, 1H, H-3'), 3.77-3.70 (m, 1H, H-4'), 3.50-3.35 (m, 2H, $CH_2$-5'), 2.64-2.53 (m, 1H, H-2'a), 2.17 (ddd, 1H, H-2'b, J1=12.9 Hz, J2=6.0 Hz, J3=3.0 Hz), 1.14 (s, 9H, tert.-butyl (tac)), 0.78 (s, 9H, tert.-butylsilyl), 0.00 (s, 6H, 2×$CH_3$ silyl). ESI-MS (neg. mode) m/z 1142.5 [2M−H]⁻, 570.0 [M−H]⁻, (pos. mode) m/z 1143.7 [2M+H]⁺, 572.2 [M+H]⁺.

Synthesis of O3'-tert.-butyldimethylsilyl-N2-(4-tert.-butylphenoxy)acetyl-O5'-(2-carboxybenzoyl)-deoxyguanosine, PS-dG(tac)-Si dG(tac)-Si (80.0 g, 140 mmol) was dissolved in ethylacetate (600 ml). Triethylamine (19.1 ml, 137 mmol), DMAP (1.71 g, 14 mmol) and phthalic acid anhydride (24.9 g, 168 mmol) were added successively and the homogeneous reaction mixture was stirred overnight at ambient temperature. The mixture was diluted with ethyl acetate (1000 ml) and extracted with a 5% aqueous solution of citric acid (3 times 150 ml), water (150 ml) and brine (150 ml). The organic phase was dried over sodium sulfate, filtered and evaporated to about half volume when the product started to precipitate. After cooling on ice for 1 hour the suspension was filtered to isolate the product as colorless solid (56.2 g). The mother liquor yielded a second crop of product upon concentration and cooling (21.3 g). Yield overall 77.5 g (77%). Purity by RP-HPLC 92.0%. $^1$H-NMR (300 MHz, DMSO-$d_6$), δ [ppm]: 13.33 (bs, 1H, COOH), 11.83, 11.75 (2×s, 2H, 2×NH), 8.24 (s, 1H, H-8), 7.81-7.89 (m, 1H, $H_{Ar}$(pht)), 7.73-7.62 (m, 2H, $H_{Ar}$(pht), 7.35 (d, 2H, $H_{Ar}$(tac), J=8.7 Hz), 6.93 (d, 2H, $H_{Ar}$(tac), J=9.0 Hz), 6.29 (t, 1H, H-1', J=6.9 Hz), 4.87 (s, 2H, $CH_2$ (tac)), 4.71-4.63 (m, 1H, H-3'), 4.48 (dd, 1H, $CH_2$-5'a, J1=11.6 Hz, J2=5.6 Hz), 4.38 (dd, 1H, $CH_2$-5'b, J1=11.7 Hz, J2=5.7 Hz), 4.20-4.13 (m, 1H, H-3'), 2.90-2.76 (m, 1H, H-2'a), 2.39 (ddd, 1H, H-2'b, J1=13.2 Hz, J2=6.0 Hz, J3=3.3 Hz), 1.29 (s, 9H, tert.-butyl (tac)), 0.92 (s, 9H, tert.-butylsilyl), 0.14, 0.13 (2×s, 6H, 2×$CH_3$ silyl). ESI-MS (neg. mode) m/z 718.2 [M−H]⁻, (pos. mode) m/z 869.4 [M+TEAH]⁺, 720.3 [M+H]⁺.

Synthesis of O3'-tert.-butyldimethylsilyl-N2-(4-tert.-butylphenoxy)acetyl-O5'-(2-(2-cyanophenoxycarbonyl)benzoyl)-deoxyguanosine, PSCp-dG(tac)-Si PS-dG(tac)-Si (84.0 g, 117 mmol) was dried by coevaporation with pyridine and dissolved in pyridine (250 ml). 2-cyanophenoltrifluoroacetate (50.3 g, 234 mmol) was added with stirring. The reaction mixture was stirred at ambient temperature overnight. The solvent was removed under reduced pressure and the residue dissolved in ethyl acetate (1500 ml). The solution was extracted with a 5% aqueous solution of citric acid (2 times 250 ml), 5% aqueous sodium hydrogencarbonate solution (2 times 250 ml) and brine (250 ml). The organic phase was dried over sodium sulfate, filtered and concentrated to a foam by evaporation. Purification by column chromatography on silica gel (ethyl acetate/hexanes, gradient elution) afforded the product in 99.0% purity by RP-HPLC as off-white foam (57.0 g). A second fraction with 96.9% purity by RP-HPLC was additionally obtained (18.5 g). Yield overall 75.5 g (79%). $^1$H-NMR (300 MHz, DMSO-d$_6$), δ [ppm]: 11.71, 11.62 (2×s, 2H, 2×NH), 8.17 (s, 1H, H-8), 7.99-7.89 (m, 2H, H$_{Ar}$), 7.85-7.72 (m, 4H, H$_{Ar}$), 7.53-7.43 (m, 2H, H$_{Ar}$), 7.25 (d, 2H, H$_{Ar}$(tac), J=9.0 Hz), 6.83 (d, 2H, H$_{Ar}$(tac), J=8.7 Hz), 6.19 (t, 1H, H-1', J=6.9 Hz), 4.76 (s, 2H, CH$_2$ (tac)), 4.62-4.55 (m, 1H, H-3'), 4.47 (dd, 1H, CH$_2$-5'a, J1=12.0 Hz, J2=5.1 Hz), 4.39 (dd, 1H, CH$_2$-5'b, J1=11.7 Hz, J2=6.0 Hz), 4.11-4.02 (m, 1H, H-3'), 2.80-2.68 (m, 1H, H-2'a), 2.36-2.25 (m, 1H, H-2'b), 1.19 (s, 9H, tert.-butyl (tac)), 0.79 (s, 9H, tert.-butylsilyl), 0.01, 0.00 (2×s, 6H, 2×CH$_3$ silyl). ESI-MS (neg. mode) m/z 819.1 [M–H]$^-$, (pos. mode) m/z 821.2 [M+H]$^+$.

Synthesis of N2-(4-tert.-butylphenoxy)acetyl-O5'-(2-(2-cyanophenoxycarbonyl)-benzoyl)-deoxyguanosine, PSCp-dG(tac)

PSCp-dG(tac)-Si (71.4 g, 87.0 mmol) was dissolved in acetonitrile (500 ml). Hydrogen fluoride in pyridine (70% HF, 23 ml) was added with stirring. The reaction was continued at ambient temperature overnight. The mixture was diluted with ethylacetate (800 ml) and treated with saturated calcium chloride solution (250 ml) under vigorous stirring. After 15 minutes the phases were separated and the organic phase extracted with saturated calcium chloride solution (300 ml), 5% aqueous sodium hydrogencarbonate solution (2 times 250 ml), a 5% aqueous solution of citric acid (2 times 250 ml), and brine (250 ml). The organic phase was dried over sodium sulfate, filtered and evaporated under reduced pressure. The solid residue was triturated with acetone and isolated by filtration. Purification by column chromatography on silica gel (dichloromethane/ethanol, gradient elution) afforded the product in 99.3% purity by RP-HPLC (40.0 g) as off-white foam. A second fraction with 96% purity by RP-HPLC was additionally obtained (9.5 g). Yield overall 49.5 g (81%). ESI-MS (neg. mode) m/z 704.9 [M–H]$^-$, (pos. mode) m/z 707.1 [M+H]$^+$.

Synthesis of N2-(4-tert.-butylphenoxy)acetyl-O3'-[2-cyanoethoxy(diisopropyl-amino)phosphanyl]-O5'-(2-(2-cyanophenoxycarbonyl)benzoyl)-deoxyguanosine, PSCp-dG(tac)-Amidite (27)

PSCp-dG(tac) (15.0 g, 21.2 mmol) was dissolved in dichloromethane (200 ml). N,N-Diisopropylethylamine (6.58 g, 50.9 mmol) was added and the solution was cooled in an ice bath. Chloro-2-cyanoethoxy(diisopropylamino)phosphane (6.05 g, 25.4 mmol) was added and the mixture stirred for 30 minutes at 0° C. The ice bath was removed and the reaction continued at ambient temperature for 24 hours. Additional N,N-Diisopropylethylamine (3.3 g, 25.4 mmol) and chloro-2-cyanoethoxy(diisopropyl-amino)phosphane (3.0 g, 12.7 mmol) were added successively and the reaction was continued overnight. The reaction mixture was diluted with dichloromethane (500 ml) and washed with cold 5% aqueous sodium hydrogencarbonate solution (3 times 100 ml) and brine (100 ml). The organic phase was dried over sodium sulfate, filtered and evaporated to an oil under reduced pressure. The oil was dissolved in dichloromethane (20 ml) and added dropwise to cooled hexane (400 ml). The supernatant was decanted and the residue was further purified by column chromatography on silica gel (ethyl acetate/hexane, gradient elution) to afford the product in 97.8% purity by RP-HPLC as colorless foam. Yield 8.2 g (43%). $^{31}$P-NMR (121.5 MHz, CDCl$_3$) δ [ppm]: 149.9, 149.6, purity by P-NMR 92.8%. $^1$H-NMR (300 MHz, CDCl$_3$), δ [ppm]: 8.01-7.93 (m, 1H, H$_{Ar}$), 7.76 (d, 1H, J=6.6 Hz, H$_{Ar}$), 7.72-7.54 (m, 5H, H$_{Ar}$), 7.46 (d, 1H, J=8.4 Hz, H$_{Ar}$), 7.36-7.24 (m, 3H, H$_{Ar}$), 6.88 (d, 2H, J=8.4 Hz, H$_{Ar}$(tac)), 6.22 (dt, 1H, J1=6.4 Hz, J2=1.8 Hz, H-1'), 4.84-4.70 (m, 1H, H-3'), 4.68-4.52 (m, 4H, H-4', H-5'a and CH$_2$ (tac)), 4.46-4.35 (m, 1H, H-5'b), 3.87-3.40 (m, 4H, POCH$_2$ and 2×NCH(CH$_3$)$_2$), 2.89-2.48 (m, 4H, CH$_2$CN and H-2'), 1.26 (s, 9H, tert.-butyl (tac)), 1.18-1.10 (m, 12H, CH$_3$ (2×NCH(CH$_3$)$_2$)). ESI-MS (neg. mode) m/z 905.0 [M–H]$^-$, (pos. mode) m/z 907.1 [M+H]$^+$.

Example 21

Synthesis of the oligonucleotide 5'-d(AGTCAGTCT)-3' with 5'-PSCp-protected amidites The oligodeoxynucleotide 5'-d(AGTCAGTCT)-3' was prepared on solid support (19) (0.2 µmol scale). The synthesis was performed on an ABI Expedite (Model 8909) DNA synthesizer. The standard DNA synthesis protocol according to the manufacturer's recommendations was modified with respect to the capping step as described in Example 8. The synthesis was performed in DMT-OFF mode. Commercial synthesis reagents for oxidation and washing steps were employed. A 10% solution of DEAEA in acetonitrile, v/v, was employed for the deblock step. The nucleoside phosphoramidite coupling steps were performed with 50 mg/ml solutions of PSCp-dT-amidite (12), PSCp-dA(mmt)-amidite (25), PSCp-dC(mmt)-amidite (26) and PSCp-dG(tac)-amidite (27) in acetonitrile. A 0.25 M solution of DCI activator in acetonitrile was used as activator for the nucleoside phosphoramidite coupling and for the capping reaction with the non-nucleosidic phosphoramidite (14). After the chain assembly with the synthesizer the crude oligonucleotides, while still bound to the support, were treated with a solution of 10% diethylamine in acetonitrile for 30 minutes at ambient temperature followed by washing of the support with acetonitrile. Cleavage and deprotection was accomplished through incubation with a 40 mM citrate buffer pH 3 (300 µl) for 16 hours at ambient temperature. The buffer solution was neutralized with a 0.1 M solution of sodium hydrogen carbonate (200 µl). The supernatant was separated from the CPG and evaporated to dryness in a vacuum centrifuge. The residue was dissolved in water (150 µl) and analyzed by anion-exchange HPLC (method A). The retention time of the product was identical to the retention time of a reference oligonucleotide. The identity of the product was further confirmed by ESI-MS analysis (calculated m/z for 5'-d(AGTCAGTCT)-3' 2713.8. found 1355.5 [M–2H]$^{2-}$, 903.2 [M–3H]$^{3-}$, 677.0 [M–4H]$^{4-}$, 541.4 [M–5H]$^{5-}$.

It is intended that each of the patents, applications, printed publications, and other published documents cited in this disclosure or referred to in this disclosure be herein incorporated by reference in their entirety.

Those skilled in the art will appreciate that numerous changes and modifications may be made to the preferred embodiments of the present invention and that such changes and modifications may be made without departing from the spirit of the invention. It is therefore intended that the appended claims cover all such equivalent variations as fall within the spirit and scope of the invention.

Notably, throughout this application various citations are provided. Each citation is specifically incorporated herein by reference in its entirety.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A method for the solid phase synthesis of oligonucleotides, wherein each synthesis cycle of the method comprises:
   a) cleaving an acyl front end protective group from a nucleoside immobilized on a solid support to liberate a hydroxyl group on the nucleoside, the acyl front end protective group comprising either an electron withdrawing group or a group capable of neighboring group participation in close proximity to its carbonyl group such that the acyl group is cleavable in ten minutes or less at room temperature by a primary amine, a secondary amine, or a mixture thereof; and
   b) coupling an acyl protected nucleoside phosphoramidite with the hydroxyl group of the nucleoside immobilized on the solid support.

2. The method of claim 1, wherein the acyl protective group is selected from the group consisting of an oxalyl monoester group, an ortho-phenoxycarbonyl benzoyl group, and a cyclohexyloxydicarbonyl group.

3. The method of claim 2, wherein the ortho-phenoxycarbonyl benzoyl group is selected from the group consisting of a 2-(4-nitrophenoxy)carbonyl benzoyl group and a 2-(2-cyanophenoxy)carbonyl benzoyl group.

4. The method of claim 1, wherein the acyl protective group is attached to the 5'-hydroxyl function of the nucleoside.

5. The method of claim 1, wherein the acyl protective group is attached to the 3'-hydroxyl function of the nucleoside.

6. The method of claim 1, wherein the cleaving reagent comprises a primary amine.

7. The method of claim 6, wherein the primary amine is selected from the group consisting of n-butylamine, n-hexylamine, 2-methoxyethylamine, and 2-(N,N-diethylamino) ethylamine.

8. The method of claim 1, wherein the cleavage of the front end protective group occurs in 1 minute or less at room temperature.

9. The method of claim 1, wherein the first nucleoside of the oligonucleotide to be synthesized is attached to the solid support via an acid-labile linker.

10. The method of claim 1, wherein the base moiety of the nucleoside phosphoramidite is either unprotected or protected with an acid-labile nucleobase protective group.

11. The method of claim 10, wherein, after synthesis of the oligonucleotide, the nucleobase protective groups of the oligonucleotide are removed with an acidic reagent.

12. The method of claim 11, wherein the acidic reagent is aqueous.

13. The method of claim 12, wherein the aqueous acidic reagent has a pH in the range of pH 2 to pH 4.

14. The method of claim 1, wherein the nucleoside phosphoramidite is a ribonucleoside and the 2'-hydroxyl function of the ribonucleoside is protected with an acid-labile 2'-protective group.

15. A nucleoside phosphoramidite comprising an acyl front end protective group and a phosphoramidite group, wherein the acyl front end protective group comprises either an electron withdrawing group or a group capable of neighboring group participation in close proximity to its carbonyl group such that the acyl group is cleavable with a primary amine, a secondary amine, or a mixture thereof in 10 minutes or less at room temperature.

16. The nucleoside phosphoramidite of claim 15, wherein the acyl front end protective group is an oxalyl monoester group.

17. The nucleoside phosphoramidite of claim 15, wherein the acyl front end protective group is an ortho-phenoxycarbonyl benzoyl group.

18. The nucleoside phosphoramidite of claim 17, wherein the ortho-phenoxycarbonyl benzoyl group is selected from the group consisting of a 2-(4-nitrophenoxy)carbonyl benzoyl group and a 2-(2-cyanophenoxy)carbonyl benzoyl group.

19. The nucleoside phosphoramidite of claim 15, wherein the acyl front end protective group is a cyclohexyloxydicarbonyl group.

20. The nucleoside phosphoramidite of claim 15, wherein the phosphoramidite group comprises a β-cyanoethyl phosphate protective group.

21. The nucleoside phosphoramidite of claim 15, wherein the base moiety of the nucleoside phosphoramidite is protected with an acid-labile nucleobase protective group.

22. The nucleoside phosphoramidite of claim 15, wherein the nucleoside is a ribonucleoside and the 2'-hydroxyl function of the ribonucleoside is protected with an acid-labile 2'-protective group.

23. The nucleoside phosphoramidite of claim 22, wherein the acid-labile 2'-protective group a 4-methoxytetrahydropyranyl group.

* * * * *